US007105534B2

(12) United States Patent
Beatch et al.

(10) Patent No.: US 7,105,534 B2
(45) Date of Patent: Sep. 12, 2006

(54) IMIDAZO[1,2-α]PYRIDINE ETHER COMPOUNDS AS ION CHANNEL MODULATORS

(75) Inventors: Gregory N. Beatch, Vancouver (CA); Yuzhong Liu, Vancouver (CA); Bertrand M. C. Plouvier, Vancouver (CA)

(73) Assignee: Cardiome Pharma Corp., Vancouver (CA)

( * ) Notice: Subject to any disclaimer, the term of this patent is extended or adjusted under 35 U.S.C. 154(b) by 0 days.

(21) Appl. No.: 10/297,988

(22) PCT Filed: Jun. 12, 2001

(86) PCT No.: PCT/CA01/00868

§ 371 (c)(1),
(2), (4) Date: Jun. 27, 2003

(87) PCT Pub. No.: WO01/96335

PCT Pub. Date: Dec. 20, 2001

(65) Prior Publication Data

US 2004/0048885 A1 Mar. 11, 2004

(30) Foreign Application Priority Data

Jun. 12, 2000 (CA) .................................... 2311483

(51) Int. Cl.
*A61K 31/437* (2006.01)

(52) U.S. Cl. ...................................................... 514/300

(58) Field of Classification Search ................. 514/300
See application file for complete search history.

(56) References Cited

U.S. PATENT DOCUMENTS

| | | | | |
|---|---|---|---|---|
| 4,450,164 | A | 5/1984 | Bristol et al. | 424/256 |
| 4,725,601 | A | 2/1988 | Ueda et al. | 514/300 |

FOREIGN PATENT DOCUMENTS

| | | |
|---|---|---|
| EP | 0 033 094 B1 | 10/1984 |
| EP | 0 261 912 | 3/1988 |
| EP | 0 204 285 B1 | 1/1992 |
| EP | 0 596 406 | 5/1994 |

OTHER PUBLICATIONS

Sanfilippo et al., J. Med. Chem., (1988), 31(11), 2221-7.*

Asano, S., et al., "The C1-Channel in Hog Gastic Vesicles Is Part of the Function of H,K-ATPase", *J. Biol. Chem.*, vol. 252, No. 27, 1987 pp. 13263-13268.

Rizzi, C., et al., "Characterization of FR 172357, a new non-peptide bradykinihn B2 receptor antagonist, in human, pig and rabbit preparations", *Eur. J. Pharmacol*, vol. 386, No. 1, 1999, pp. 25-31.

* cited by examiner

*Primary Examiner*—Phyllis G. Spivack
(74) *Attorney, Agent, or Firm*—Seed IP Law Group PLLC

(57) ABSTRACT

Methods of using imidazo[1,2-α]pyridine ether compounds for modulating ion channel activity in a warm-blooded animal are disclosed.

29 Claims, 1 Drawing Sheet

IMIDAZO[1,2-α]PYRIDINE ETHER COMPOUNDS AS ION CHANNEL MODULATORS

FIELD OF THE INVENTION

The present invention is generally directed toward imidazo[1,2-α]pyridine ether compounds, pharmaceutical compositions and kits containing the imidazo[1,2-α]pyridine ether compounds, and therapeutic uses thereof.

BACKGROUND OF THE INVENTION

Ion channels are ubiquitous membrane proteins in the cells of warm-blooded animals such as mammals. Their critical physiological roles include control of the electrical potential across the membrane, mediation of ionic and fluid balance, facilitation of neuromuscular and neuronal transmission, rapid transmembrane signal transduction, and regulation of secretion and contractility.

For example, cardiac ion channels are proteins that reside in the cell membrane and control the electrical activity of cardiac tissue. In response to external stimuli, such as changes in potential across the cell membrane, these ion channels can form a pore through the cell membrane, and allow movement of specific ions into or out of the cell. The integrated behavior of thousands of ion channels in a single cell results in an ionic current, and the integrated behavior of many of these ionic currents makes up the characteristic cardiac action potential.

Arrhythmia is a variation from the normal rhythm of the heart beat and generally represents the end product of abnormal ion-channel structure, number or function. Both atrial (including supraventricular) arrhythmias and ventricular arrhythmias are known. The major cause of fatalities due to cardiac arrhythmias is the subtype of ventricular arrhythmias known as ventricular fibrillation (VF). Conservative estimates indicate that, in the U.S. alone, each year over one million Americans will have a new or recurrent coronary attack. About 650,000 of these will be first heart attacks and 450,000 will be recurrent attacks. About one-third of the people experiencing these attacks will die of them. At least 250,000 people a year die of coronary heart disease within 1 hour of the onset of symptoms and before they reach a hospital. These are sudden deaths caused by cardiac arrest, usually resulting from ventricular fibrillation.

Atrial fibrillation (AF) is the most common arrhythmia seen in clinical practice and is a cause of morbidity in many individuals (Pritchett E. L., *N. Engl. J. Med.* 327(14):1031 Oct. 1, 1992, discussion 1031–2; Kannel and Wolf, *Am. Heart J.* 123(1):264–7 January 1992). I prevalence is likely to increase as the population ages and it is estimated that 3–5% of patients over the age of 60 years have AF (Kannel W. B., Abbot R. D., Savage D. D., McNamara P. M., *N. Engl. J. Med.* 306(17):1018–22, 1982; Wolf P. A., Abbot R. D., Kannel W. B. *Stroke.* 22(8):983–8, 1991). While atrial flutter and AF are rarely fatal, they can impair cardiac function. In addition to being a major cause of stroke, AF usually progresses to ventricular fibrillation if left untreated. (Hinton R. C., Kistler J. P., Fallon J. T., Friedlich A. L., Fisher C. M., *American Journal of Cardiology* 40(4):509–13, 1977; Wolf P. A., Abbot R. D., Kannel W. B., *Archives of Internal Medicine* 147(9):1561–4, 1987; Wolf P. A., Abbot R. D., Kannel W. B. *Stroke.* 22(8):983–8, 1991; Cabin H. S., Clubb K. S., Hall C., Perlmutter R. A., Feinstein A. R., *American Journal of Cardiology* 65(16):1112–6, 1990).

Antiarrhythmic agents have been developed to prevent or alleviate cardiac arrhythmia. For example, Class I antiarrhythmic compounds have been used to treat atrial/supraventricular arrhythmias and ventricular arrhythmias. Treatment of ventricular arrhythmia is very important since such an arrhythmia can be fatal. Serious ventricular arrhythmias (ventricular tachycardia/flutter and ventricular fibrillation) occur most often in the presence of myocardial ischemia and/or infarction. Ventricular fibrillation often occurs in the setting of acute myocardial ischemia, before infarction fully develops. At present, there is no satisfactory pharmacotherapy for the treatment and/or prevention of ventricular fibrillation during acute ischemia. In fact, many Class I antiarrhythmic compounds may actually increase mortality in patients who have had a myocardial infarction.

Class Ia, Ic and III antiarrhythmic drugs have been used to convert recent onset AF to sinus rhythm and prevent recurrence of the arrhythmia (Fuch and Podrid, 1992; Nattel S., Hadjis T., Talajic M., *Drugs* 48(3):345–71, 1994). However, drug therapy is often limited by adverse effects, including the possibility of increased mortality, and inadequate efficacy (Feld G. K., *Circulation.* 83(6):2248–50, 1990; Coplen S. E., Antman E. M., Berlin J. A., Hewitt P., Chalmers T. C., *Circulation* 1991; 83(2):714 and *Circulation* 82(4):1106–16, 1990; Flaker G. C., Blackshear J. L., McBride R., Kronmal R. A., Halperin J. L., Hart R. G., *Journal of the American College of Cardiology* 20(3): 527–32, 1992; CAST, *N. Engl. J. Med.* 321:406, 1989; Nattel S., *Cardiovascular Research.* 37(3):567–77, 1998). Conversion rates for Class I antiarrhythmics range between 50–90% (Nattel S., Hadjis T., Talajic M., *Drugs* 48(3): 345–71, 1994; Steinbeck G., Remp T., Hoffmann E., *Journal of Cardiovascular Electrophysiology.* 9(8 Suppl):S104–8, 1998). Class III antiarrhythmics appear to be more effective for terminating atrial flutter than for AF and are generally regarded as less effective than Class I drugs for terminating of AF (Nattel S., Hadjis T., Talajic M., *Drugs.* 48(3):345–71, 1994; Capucci A., Aschieri D., Villani G. Q., *Drugs & Aging* 13(1):51–70, 1998). Examples of such drugs include ibutilide, dofetilide and sotalol. Conversion rates for these drugs range between 30–50% for recent onset AF (Capucci A., Aschieri D., Villani G. Q., *Drugs & Aging* 13(1):51–70, 1998), and they are also associated with a risk of the induction of Torsades de Pointes ventricular tachyarrhythmias. For ibutilide, the risk of ventricular proarrhythmia is estimated at ~4.4%, with ~1.7% of patients requiring cardioversion for refractory ventricular arrhythmias (Kowey P. R., VanderLugt J. T., Luderer J. R., *American Journal of Cardiology* 78(8A):46–52, 1996). Such events are particularly tragic in the case of AF as this arrhythmia is rarely fatal in and of itself.

Therefore, there is a need in the art to identify new antiarrhythmic treatments, for both atrial/supraventricular arrhythmia and ventricular arrhythmia. The present invention fulfills this need, and further provides other related advantages.

Substituted imidazo[1,2-α]pyridines are known in the art. Some of these are reported to have antiulcerative activity (e.g. U.S. Pat. No. 4,725,601; EP-B-0204285; U.S. Pat. No. 4,450,164; EP-B-0033094; and Kaminski J. J. et al., J. Med. Chem. 30:2031–2046, 1987).

SUMMARY OF THE INVENTION

In one embodiment, the present invention provides a method for modulating ion channel activity in a warm-blooded animal comprising administering to a warm-blooded animal in need thereof, an effective amount of a compound of formula (I), or a pharmaceutically acceptable salt, ester, amide, complex, chelate, solvate, stereoisomer, stereoisomeric mixture, geometric isomer, crystalline or amorphous form, metabolite, metabolic precursor or prodrug thereof:

(I)

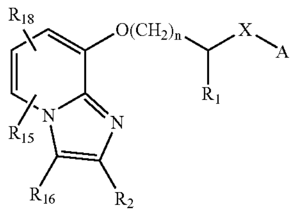

wherein, independently at each occurrence, n is selected from 0, 1, 2 and 3;

X is selected from a direct bond, —C($R_3$)═CH—, and —C($R_4$,$R_5$)—Y—;

Y is selected from a direct bond, O, S, and $C_1$–$C_4$alkylene;

$R_2$, $R_{15}$, $R_{16}$ and $R_{18}$ are independently selected from bromine, chlorine, fluorine, carboxy, hydrogen, hydroxy, hydroxymethyl, methanesulfonamido, nitro, sulfamyl, cyano, $CHF_2$, $CH_2F$, $CF_3$, $C_2$–$C_7$alkanoyloxy, $C_1$–$C_6$alkyl, $C_3$–$C_8$cycloalkyl, aryl, benzyl, $C_1$–$C_6$alkoxy, $C_2$–$C_7$alkoxycarbonyl, $C_1$–$C_6$thioalkyl, $CH_2N(R_{13},R_{14})$ and $N(R_{13},R_{14})$ where $R_{13}$ and $R_{14}$ are independently selected from hydrogen, acetyl, methanesulfonyl, and $C_1$–$C_6$alkyl, or $R_2$ and $R_{16}$, when taken together with the carbon to which they are attached, may form a $C_4$–$C_7$cycloalkyl;

$R_3$ is selected from hydrogen, $C_1$–$C_6$alkyl, $C_3$–$C_8$cycloalkyl, aryl, and benzyl;

$R_1$, $R_4$ and $R_5$ are independently selected from hydrogen, $C_1$–$C_6$alkyl, aryl and benzyl, or $R_4$ and $R_5$, when taken together with the carbon to which they are attached, may form a spiro $C_3$–$C_5$cycloalkyl;

A is selected from $C_5$–$C_{12}$alkyl, a $C_3$–$C_{13}$carbocyclic ring, and ring systems selected from formulae (II), (III), (IV), (V), (VI) and (VII):

(II)

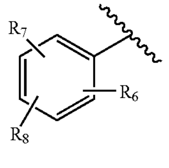

where $R_6$, $R_7$ and $R_8$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, cyano, aryl and $N(R_{13},R_{14})$ where $R_{13}$ and $R_{14}$ are independently selected from hydrogen, acetyl, methanesulfonyl, and $C_1$–$C_6$alkyl;

(III)

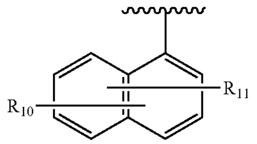

and (IV)

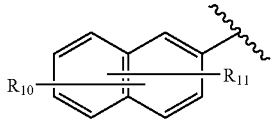

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, cyano, aryl and $N(R_{13},R_{14})$ where $R_{13}$ and $R_{14}$ are independently selected from hydrogen, acetyl, methanesulfonyl, and $C_1$–$C_6$alkyl;

(V)

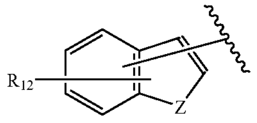

where $R_{12}$ is selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, cyano, aryl and $N(R_{13},R_{14})$ where $R_{13}$ and $R_{14}$ are independently selected from hydrogen, acetyl, methanesulfonyl, and $C_1$–$C_6$alkyl; and Z is selected from CH, $CH_2$, O, N and S, where Z may be directly bonded to "X" as shown in formula (I) when Z is CH or N, or Z may be directly bonded to $R_9$ when Z is N, and $R_9$ is selected from hydrogen, $C_1$–$C_6$alkyl, $C_3$–$C_8$cycloalkyl, aryl and benzyl; with the proviso that when X is a direct bond and R1 is hydrogen then R6, R7 and R8 cannot all be hydrogen;

(VI)

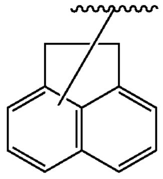

(VII)

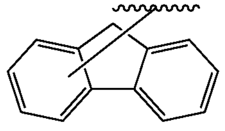

.

In another embodiment, the present invention provides a method for modulating ion channel activity in an in vitro setting comprising administering in vitro an effective amount of a compound of formula (I) as defined above or a pharmaceutically acceptable salt, ester, amide, complex, chelate, solvate, stereoisomer, stereoisomeric mixture, geometric isomer, crystalline or amorphous form, metabolite, metabolic precursor or prodrug thereof.

In another embodiment, the present invention provides a compound of formula (I) as defined above or a pharmaceutically acceptable salt, ester, amide, complex, chelate, solvate, stereoisomer, stereoisomeric mixture, geometric isomer, crystalline or amorphous form, metabolite, metabolic precursor or prodrug thereof, wherein X is —$C(R_4,R_5)$—Y—, and $R_4$ and $R_5$, when taken together with the carbon to which they are attached form a spiro $C_3$–$C_5$cycloalkyl.

In another embodiment, the present invention provides a compound of formula (I) as defined above or a pharmaceutically acceptable salt, ester, amide, complex, chelate, solvate, stereoisomer, stereoisomeric mixture, geometric isomer, crystalline or amorphous form, metabolite, metabolic precursor or prodrug thereof, wherein A is selected from formula (V),and Z is N or S.

In other embodiments, the present invention provides a composition or medicament that includes a compound according to formula (I), wherein X is —$C(R_4,R_5)$—Y—, and $R_4$ and $R_5$, when taken together with the carbon to which they are attached form a spiro $C_3$–$C_5$cycloalkyl; in combination with a pharmaceutically acceptable carrier, diluent or excipient, and further provides a method for the manufacture of a composition or medicament that contains one or more such compounds.

In other embodiments, the present invention provides a composition or medicament that includes a compound according to formula (I), wherein A is selected from formula (V), and Z is N or S; in combination with a pharmaceutically acceptable carrier, diluent or excipient, and further provides a method for the manufacture of a composition or medicament that contains one or more such compounds.

In another embodiment, the present invention provides a compound of formula (I) or composition containing a compound of formula (I), for use in methods for either modulating ion channel activity in a warm-blooded animal or for modulating ion channel activity in vitro. Some of the ion channels to which the compounds, compositions and methods of the present invention have modulating effect are various potassium and sodium channels. These potassium and sodium ion channels may be voltage-activated (also known as voltage-gated) or ligand-activated (also known as ligand-gated), and may be present in cardiac and/or neuronal systems. More specifically, some of the cardiac and/or neuronal potassium ion channels are responsible for one or more early repolarising currents comprise of ionic currents which activate rapidly after depolarisation of membrane voltage and which effect repolarisation of the cells. The early repolarising currents comprise the transient outward potassium current ($I_{to}$) and/or the ultrarapid delayed rectifier current ($I_{Kur}$), and include at least one of the Kv4.2, Kv4.3, Kv2.1, Kv1.4 and Kv1.5 currents. Other potassium ion channels may include the HERG channels. Furthermore, the voltage-activated sodium ion channels comprise the $Na_v1$, $Na_v2$ or $Na_v3$ series and may be present in cardiac, neuronal, skeletal muscle, central nervous and/or peripheral nervous systems.

In other embodiments, the present invention provides pharmaceutical compositions that contain at least one compound of formula (I), with the provisos that X is —$C(R_4,R_5)$—Y—, and $R_4$ and $R_5$, when taken together with the carbon to which they are attached form a spiro $C_3$–$C_5$cycloalkyl; or A is selected from formula (V), and Z is N or S; in an amount effective to treat a disease or condition in a warm-blooded animal suffering from or having the disease or condition, and/or prevent a disease or condition in a warm-blooded animal that would otherwise occur, and further contains at least one pharmaceutically acceptable carrier, diluent or excipient.

The invention further provides for methods of treating a disease or condition in a warm-blooded animal suffering from or having the disease or condition, and/or preventing a disease or condition from arising in a warm-blooded animal, wherein a therapeutically effective amount of a compound of formula (I), or a composition containing a compound of formula (I) is administered to a warm-blooded animal in need thereof. Some of the diseases and conditions to which the compounds, compositions and methods of the present invention have applicability are as follows: arrhythmia including atrial/supraventricular arrhythmia and ventricular arrhythmia, atrial fibrillation, ventricular fibrillation, atrial flutter, ventricular flutter, diseases of the central nervous system, convulsion, cardiovascular diseases (e.g. diseases caused by elevated blood cholesterol or triglyceride levels), cerebral or myocardial ischemias, hypertension, long-QT syndrome, stroke, migraine, ophthalmic diseases, diabetes mellitus, myopathies, Becker's myotonia, myasthenia gravis, paramyotonia congentia, malignant hyperthermia, hyperkalemic periodic paralysis, Thomsen's myotonia, autoimmune disorders, graft rejection in organ transplantation or bone marrow transplantation, heart failure, hypotension, Alzheimer's disease, dementia or other mental disorder, alopecia, sexual dysfunction, impotence, demyelinating diseases, multiple sclerosis, amyotrophic lateral sclerosis, epileptic spasms, depression, anxiety, schizophrenia, Parkinson's disease, respiratory disorders, cystic fibrosis, asthma, cough, inflammation, arthritis, allergies, urinary incontinence, irritable bowel syndrome, and gastrointestinal disorders such as gastrointestinal inflammation and ulcer.

In another embodiment, the present invention provides a pharmaceutical composition containing an amount of a compound of formula (I), with the provisos that X is —$C(R_4,R_5)$—Y—, and $R_4$ and $R_5$, when taken together with the carbon to which they are attached form a spiro $C_3$–$C_5$cycloalkyl; or A is selected from formula (V), and Z is N or S; effective to produce analgesia or local anesthesia in a warm-blooded animal in need thereof, and a pharmaceutically acceptable carrier, diluent, or excipient. The invention further provides a method for producing analgesia or local anesthesia in a warm-blooded animal, which includes administering to a warm-blooded animal in need thereof an effective amount of a compound of formula (I) or a pharmaceutical composition containing a compound of formula (I). These compositions and methods may be used to relieve or forestall the sensation of pain in a warm-blooded animal.

In another embodiment, the present invention provides a pharmaceutical composition containing an amount of a compound of formula (I), with the provisos that X is —$C(R_4,R_5)$—Y—, and $R_4$ and $R_5$, when taken together with the carbon to which they are attached form a spiro $C_3$–$C_5$cycloalkyl; or A is selected from formula (V), and Z is N or S; effective to enhance the libido in a warm-blooded animal in need thereof, and a pharmaceutically acceptable carrier, diluent, or excipient. The invention further provides a method for enhancing libido in a warm-blooded animal which includes administering to a warm-blooded animal in need thereof an effective amount of a compound of formula (I) or a pharmaceutical composition containing a compound of formula (I). These compositions and methods may be used, for example, to treat a sexual dysfunction, e.g., impotence in males, and/or to enhance the sexual desire of a patient without a sexual dysfunction. As another example, the therapeutically effective amount may be administered to a bull (or other breeding stock), to promote increased semen ejaculation, where the ejaculated semen is collected and stored for use as it is needed to impregnate female cows in promotion of a breeding program.

These and other embodiments of the present invention will become evident upon reference to the following drawings and detailed description.

DETAILED DESCRIPTION OF THE INVENTION

Figure 1:
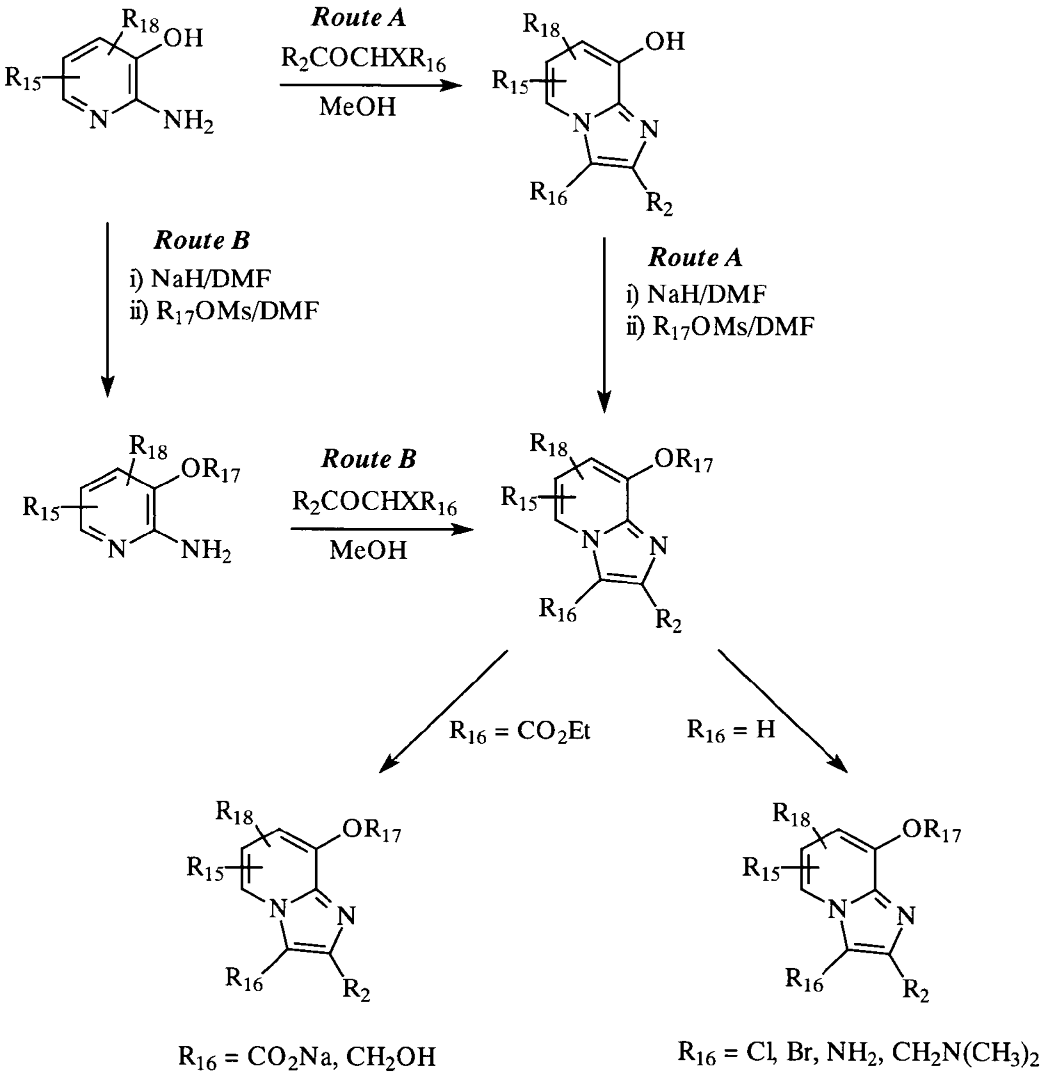
FIG. 1 illustrates the general reaction scheme that may be used for preparing an imidazo[1,2-α]pyridine compound of the present invention.

As noted above, the present invention is directed to imidazo[1,2-α]pyridine ether compounds, compositions containing the imidazo[1,2-α]pyridine ether compounds, and various uses for the compound and compositions. Such uses include modulation/blockade of ion channels in vitro or in vivo, the treatment or prevention of arrhythmias, the production of analgesia, and other uses as described herein. An understanding of the present invention may be aided by reference to the following definitions and explanation of conventions used herein.

Definitions and Conventions

In the formulae depicted herein, a bond to a substituent and/or a bond that links a molecular fragment to the remainder of a compound may be shown as intersecting one or more bonds in a ring structure. This indicates that the bond may be attached to any one of the atoms that constitutes the ring structure, so long as a hydrogen atom could otherwise be present at that atom. Where no particular substituent(s) is identified for a particular position in a structure, then hydrogen(s) is present at that position. For example, compounds of the invention containing the A—X—CH($R_1$)— group where A equals formula (II)

(II)

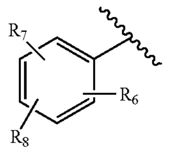

are intended to encompass compounds having the group (B):

(B)

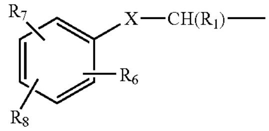

where the group (B) is intended to encompass groups wherein any ring atom that could otherwise be substituted with hydrogen, may instead be substituted with either $R_6$, $R_7$ or $R_8$, with the proviso that each of $R_6$, $R_7$ and $R_8$ appears once and only once on the ring. Ring atoms that are not substituted with any of $R_6$, $R_7$ or $R_8$ are substituted with hydrogen. In those instances where the invention specifies that a non-aromatic ring is substituted with more than one R group, and those R groups are shown connected to the non-aromatic ring with bonds that bisect ring bonds, then the R groups may be present at different atoms of the ring, or on the same atom of the ring, so long as that atom could otherwise be substituted with a hydrogen atom.

Likewise, where the invention specifies compounds containing the A—X—CH($R_1$)— group where A equals the aryl group (V)

(V)

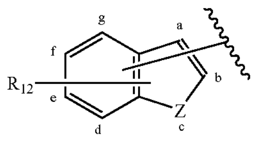

the invention is intended to encompass compounds wherein —X—CH($R_1$)— is joined through X to the aryl group (V) at any atom which forms the aryl group (V) so long as that atom of group (V) could otherwise be substituted with a hydrogen atom. Thus, there are seven positions (identified with the letters "a" through "g") in structure (V) where the —X—CH($R_1$)— group could be attached, and it is attached at one of those seven positions. The $R_{12}$ group would occupy one and only one of the remaining six positions, and hydrogen atoms would be present in each of the five remaining positions. It is to be understood that when Z represents a divalent atom, e.g., oxygen or sulfur, then Z cannot be directly bonded to —X—CH($R_1$)—.

When the invention specifies the location of an asymmetric divalent radical, then that divalent radical may be positioned in any possible manner that provides a stable chemical structure. For example, for compounds containing the A-X—CH($R_1$)— group where X is C($R_4$,$R_5$)—Y—, the invention provides compounds having both the A-C($R_4$, $R_5$)—Y—CH($R_1$)— and A-Y—C($R_4$,$R_5$)—CH($R_1$)— groups.

The compounds of the present invention may contain one or more asymmetric carbon atoms and thus may exist as enantiomers and diastereomers. Unless otherwise noted, the present invention includes all enantiomeric and diastereomeric forms of the imidazo[1,2-α]pyridine ether compounds of the invention. Pure stereoisomers, mixtures of enantiomers and/or diastereomers, and mixtures of different compounds of the invention are included within the present invention. Thus, compounds of the present invention may occur as racemates, racemic mixtures and as individual diastereomers, or enantiomers with all isomeric forms being included in the present invention. A racemate or racemic mixture does not imply a 50:50 mixture of stereoisomers.

The phrase "independently at each occurrence" is intended to mean (i) when any variable occurs more than one time in a compound of the invention, the definition of that variable at each occurrence is independent of its definition at every other occurrence; and (ii) the identity of any one of two different variables (e.g., $R_1$ within the set $R_1$ and $R_2$) is selected without regard to the identity of the other member of the set. However, combinations of substituents and/or variables are permissible only if such combinations result in stable compounds.

In accordance with the present invention and as used herein, the following terms are defined to have following meanings, unless explicitly stated otherwise:

"Acid addition salts" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Acyl" refers to branched or unbranched hydrocarbon fragments terminated by a carbonyl —(C═O)— group containing the specified number of carbon atoms. Examples include acetyl [$CH_3C$(═O)—, a $C_2$acyl] and propionyl [$CH_3CH_2C$(═O)—, a $C_3$acyl].

"Alkanoyloxy" refers to an ester substituent wherein the non-carbonyl oxygen is the point of attachment to the molecule. Examples include propanoyloxy [($CH_3CH_2C$(═O)—O—, a $C_3$alkanoyloxy] and ethanoyloxy [$CH_3C$(═O)—O—, a $C_2$alkanoyloxy].

"Alkoxy" refers to an O-atom substituted by an alkyl group, for example, methoxy [—$OCH_3$, a $C_1$alkoxy].

"Alkoxyalkyl" refers to a alkylene group substituted with an alkoxy group. For example, methoxyethyl [$CH_3OCH_2CH_2$—] and ethoxymethyl ($CH_3CH_2OCH_2$—] are both $C_3$alkoxyalkyl groups.

"Alkoxycarbonyl" refers to an ester substituent wherein the carbonyl carbon is the point of attachment to the molecule. Examples include ethoxycarbonyl [$CH_3CH_2OC$(═O)—, a $C_3$alkoxycarbonyl] and methoxycarbonyl [$CH_3OC$(═O)—, a $C_2$alkoxycarbonyl].

"Alkyl" refers to a branched or unbranched hydrocarbon fragment containing the specified number of carbon atoms and having one point of attachment. Examples include n-propyl (a $C_3$alkyl), iso-propyl (also a $C_3$alkyl), and t-butyl (a $C_4$alkyl).

"Alkylene" refers to a divalent radical which is a branched or unbranched hydrocarbon fragment containing the specified number of carbon atoms, and having two points of attachment. An example is propylene [—$CH_2CH_2CH_2$—, a $C_3$alkylene].

"Alkylcarboxy" refers to a branched or unbranched hydrocarbon fragment terminated by a carboxylic acid group [—COOH]. Examples include carboxymethyl [HOOC—$CH_2$—, a $C_2$alkylcarboxy] and carboxyethyl [HOOC—$CH_2CH_2$—, a $C_3$alkylcarboxy].

"Aryl" refers to aromatic groups which have at least one ring having a conjugated pi electron system and includes carbocyclic aryl, and biaryl groups, all of which may be optionally substituted. Phenyl and naphthyl groups are preferred carbocyclic aryl groups.

"Aralkyl" refers to an alkylene group wherein one of the points of attachment is to an aryl group. An example of an aralkyl group is the benzyl group [$C_6H_5CH_2$—, a $C_7$aralkyl group].

"Cycloalkyl" refers to a ring, which may be saturated or unsaturated and monocyclic, bicyclic, or tricyclic formed entirely from carbon atoms. An example of a cycloalkyl group is the cyclopentenyl group ($C_5H_7$—), which is a five carbon ($C_5$) unsaturated cycloalkyl group.

"Carbocyclic" refers to a ring which may be either an aryl ring or a cycloalkyl ring, both as defined above.

"Carbocyclic aryl" refers to aromatic groups wherein the atoms which form the aromatic ring are carbon atoms. Carbocyclic aryl groups include monocyclic carbocyclic aryl groups such as phenyl, and bicyclic carbocyclic aryl groups such as naphthyl, all of which may be optionally substituted.

"Heteroatom" refers to a non-carbon atom, where boron, nitrogen, oxyg7en, sulfur and phosphorus are preferred heteroatoms, with nitrogen, oxygen and sulfur being particularly preferred heteroatoms in the compounds of the present invention.

"Heteroaryl" refers to aryl groups having from 1 to 9 carbon atoms and the remainder of the atoms are heteroatoms, and includes those heterocyclic systems described in "Handbook of Chemistry and Physics," 49th edition, 1968, R. C. Weast, editor; The Chemical Rubber Co., Cleveland, Ohio. See particularly Section C, Rules for Naming Organic Compounds, B. Fundamental Heterocyclic Systems. Suitable heteroaryls include furanyl, thienyl, pyridyl, pyrrolyl, pyrimidyl, pyrazinyl, imidazolyl, and the like.

"Hydroxyalkyl" refers to a branched or unbranched hydrocarbon fragment bearing an hydroxy (—OH) group. Examples include hydroxymethyl (—$CH_2OH$, a $C_1$hydroxyalkyl) and 1-hydroxyethyl (—$CHOHCH_3$, a $C_2$hydroxyalkyl).

"Thioalkyl" refers to a sulfur atom substituted by an alkyl group, for example thiomethyl ($CH_3S$—, a $C_1$thioalkyl).

"Modulating" in connection with the activity of an ion channel means that the activity of the ion channel may be either increased or decreased in response to administration of a compound or composition or method of the present invention. Thus, the ion channel may be activated, so as to transport more ions, or may be blocked, so that fewer or no ions are transported by the channel.

"Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

"Pharmaceutically acceptable salt" refers to salts of the compounds of the present invention derived from the combination of such compounds and an organic or inorganic acid (acid addition salts) or an organic or inorganic base (base addition salts). The compounds of the present invention may be used in either the free base or salt forms, with both forms being considered as being within the scope of the present invention.

The "therapeutically effective amount" of a compound of the present invention will depend on the route of administration, the type of warm-blooded animal being treated, and the physical characteristics of the specific warm-blooded animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which those skilled in the medical arts will recognize.

Compositions described herein as "containing a compound of formula (I)" encompass compositions that contain more than one compound of formula (I).

Compounds of the Present Invention

Compounds of the present invention are imidazo[b 1,2-α]pyridines which may be represented by formula (I):

(I)

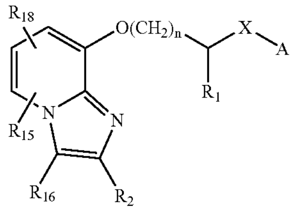

wherein, independently at each occurrence, n is selected from 0, 1, 2 and 3;

X is selected from a direct bond, —C($R_3$)═CH—, and —C($R_4$,$R_5$)—Y—;

Y is selected from a direct bond, O, S, and $C_1$–$C_4$alkylene;

$R_2$, $R_{15}$, $R_{16}$ and $R_{18}$ are independently selected from bromine, chlorine, fluorine, carboxy, hydrogen, hydroxy, hydroxymethyl, methanesulfonamido, nitro, sulfamyl, cyano, $CHF_2$, $CH_2F$, $CF_3$, $C_2$–$C_7$alkanoyloxy, $C_1$–$C_6$alkyl, $C_3$–$C_8$cycloalkyl, aryl, benzyl, $C_1$–$C_6$alkoxy, $C_2$–$C_7$alkoxycarbonyl, $C_1$–$C_6$thioalkyl, $CH_2N(R_{13},R_{14})$ and $N(R_{13},R_{14})$ where $R_{13}$ and $R_{14}$ are independently selected from hydrogen, acetyl, methanesulfonyl, and $C_1$–$C_6$alkyl, or $R_2$ and $R_{16}$, when taken together with the carbon to which they are attached, may form a $C_4$–$C_7$cycloalkyl;

$R_3$ is selected from hydrogen, $C_1$–$C_6$alkyl, $C_3$–$C_8$cycloalkyl, aryl, and benzyl;

$R_1$, $R_4$ and $R_5$ are independently selected from hydrogen, $C_1$–$C_6$alkyl, aryl and benzyl, or $R_4$ and $R_5$, when taken together with the carbon to which they are attached, may form a spiro $C_3$–$C_5$cycloalkyl;

A is selected from $C_5$–$C_{12}$alkyl, a $C_3$–$C_{13}$carbocyclic ring, and ring systems selected from formulae (II), (III), (IV), (V), (VI) and (VII):

(II)

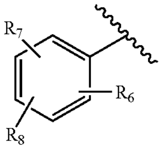

where $R_6$, $R_7$ and $R_8$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, cyano, aryl and $N(R_{13},R_{14})$ where $R_{13}$ and $R_{14}$ are independently selected from hydrogen, acetyl, methanesulfonyl, and $C_1$–$C_6$alkyl;

(III)

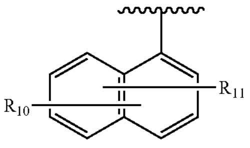

and

-continued (IV)

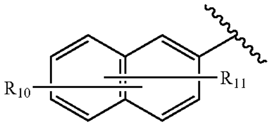

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, cyano, aryl and $N(R_{13},R_{14})$ where $R_{13}$ and $R_{14}$ are independently selected from hydrogen, acetyl, methanesulfonyl, and $C_1$–$C_6$alkyl;

(V)

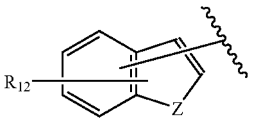

where $R_{12}$ is selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, cyano, aryl and $N(R_{13},R_{14})$ where $R_{13}$ and $R_{14}$ are independently selected from hydrogen, acetyl, methanesulfonyl, and $C_1$–$C_6$alkyl; and Z is selected from CH, $CH_2$, O, N and S, where Z may be directly bonded to "X" as shown in formula (I) when Z is CH or N, or Z may be directly bonded to $R_9$ when Z is N, and $R_9$ is selected from hydrogen, $C_1$–$C_6$alkyl, $C_3$–$C_8$cycloalkyl, aryl and benzyl; with the proviso that when X is a direct bond and R1 is hydrogen then R6, R7 and R8 cannot all be hydrogen;

(VI)

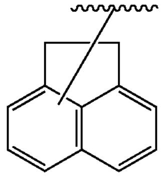

(VII)

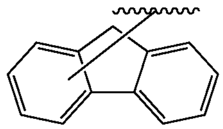

.

Compounds of formula (I) are imidazo[1,2-α]pyridine ethers. More specifically, these imidazo[1,2-α]pyridine ethers may contain various substituents ($R_2$, $R_{15}$, $R_{16}$ and $R_{18}$) on the imidazo[1,2-α]pyridine ring system and an ether side chain. The ether side chain of the compounds of the present invention is attached at position C8 of the imidazo[1,2-α]pyridine moiety and is linked by one or more methylene groups ($CH_2$) (n=1, 2 or 3) or directly (n=0) to the remaining part (—$CHR_1$—X-A) of the chain.

Depending upon the identity of X, the ether side chain, —CH($R_1$)—X-A, in formula (I) may take several forms. For example, a compound of formula (I) may have X as a —$C(R_4,R_5)$—Y— group, where Y may be any of a direct bond, an oxygen atom (O), a sulfur atom (S) or a $C_1$–$C_4$alkylene group. $R_4$ and $R_5$ are independently selected from hydrogen, $C_1$–$C_6$alkyl, aryl and benzyl, or $R_4$ and $R_5$, when taken together with the carbon to which they are attached, may form a spiro $C_3$–$C_5$cycloalkyl. Thus, compounds of the invention include compounds of formula (I) where $R_4$ and $R_5$ are hydrogen and Y is a direct bond, such that X may be $CH_2$.

Alternatively, X may be an alkenylene moiety, e.g., a cis-or trans-alkenylene moiety, $C(R_3)$═CH, where $R_3$ may be any of hydrogen, $C_1$–$C_6$alkyl, $C_3$–$C_8$cycloalkyl, aryl or benzyl. For compounds of formula (I) where X is an alkenylene moiety, X is preferably a trans-alkenylene moiety.

Ether side chain component A is generally a hydrophobic moiety. Typically, a hydrophobic moiety is comprised of non-polar chemical groups such as hydrocarbons or hydrocarbons substituted with halogens or ethers or heterocyclic groups containing nitrogen, oxygen, or sulfur ring atoms. Suitable hydrocarbons are $C_5$–$C_{12}$alkyl and $C_3$–$C_{13}$carbocyclic rings. Particularly preferred cyclic hydrocarbons include selected optionally substituted aromatic groups such as those represented by formulae (II), (III), (IV) and (V).

A suitable "A" group within the compounds of the present invention is an optionally substituted phenyl ring represented by formula (II):

(II)

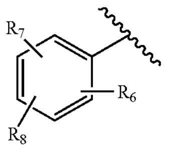

where $R_6$, $R_7$ and $R_8$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, cyano, aryl and $N(R_{13},R_{14})$ where $R_{13}$ and $R_{14}$ are independently selected from hydrogen, acetyl, methanesulfonyl, and $C_1$–$C_6$alkyl.

Other suitable "A" groups in compounds of the present invention are optionally substituted 1-naphthyl groups as represented by formula (III):

(III)

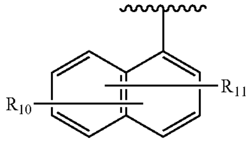

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, cyano, aryl and $N(R_{13},R_{14})$ where $R_{13}$ and $R_{14}$ are independently selected from hydrogen, acetyl, methanesulfonyl, and $C_1$–$C_6$alkyl.

Other suitable "A" groups in compounds of the present invention are optionally substituted 2-naphthyl group as represented by formula (IV):

(IV)

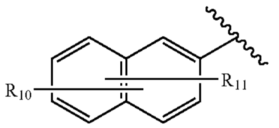

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, cyano, aryl and $N(R_{13},R_{14})$ where $R_{13}$ and $R_{14}$ are independently selected from hydrogen, acetyl, methanesulfonyl, and $C_1$–$C_6$alkyl, as defined above.

Other suitable "A" groups in compounds of the present invention are optionally substituted aromatic groups represented by formula (V):

(V)

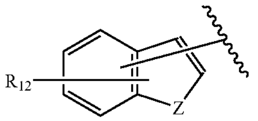

where $R_{12}$ is selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, cyano, aryl and $N(R_{13},R_{14})$ where $R_{13}$ and $R_{14}$ are independently selected from hydrogen, acetyl, methanesulfonyl, and $C_1$–$C_6$alkyl; and Z is selected from CH, $CH_2$, O, N and S, where Z may be directly bonded to "X" as shown in formula (I) when Z is CH or N, or Z may be directly bonded to $R_9$ when Z is N, and $R_9$ is selected from hydrogen, $C_1$–$C_6$alkyl, $C_3$–$C_8$cycloalkyl, aryl and benzyl.

The aryl groups represented by formula (V) are derivatives of indene, indole, benzofuran, and thianaphthene when Z is methylene, nitrogen, oxygen, and sulfur, respectively. Preferred heterocyclic groups of formula (V) include indole where Z is NH, benzofuran where Z is O, and thianaphthene where Z is S.

Another suitable "A" group in compounds of the present invention is the acenaphthyl group. Still another suitable "A" group in compounds of the present invention is the fluorenyl group.

In another preferred embodiment, the invention provides a compound of formula (I) wherein independently at each occurrence, n is 2, and all other variables are as defined above for compounds of formula (I).

In another preferred embodiment, the invention provides a compound of formula (I) wherein X is —$C(R_4,R_5)$—Y—, and $R_4$ and $R_5$, when taken together with the carbon to which they are attached form a spiro $C_3$–$C_5$cycloalkyl; and all other variables are as defined above for compounds of formula (I).

In yet another preferred embodiment, the invention provides a compound of formula (I) wherein X is —$C(R_4,R_5)$—

Y—, and $R_4$ and $R_5$, when taken together with the carbon to which they are attached form a spiro $C_3$–$C_5$cycloalkyl, and Y is a direct bond; and all other variables are as defined above for compounds of formula (I).

In yet another preferred embodiment, the invention provides a compound of formula (I) wherein X is —C($R_4$,$R_5$)—Y—, and $R_4$ and $R_5$, when taken together with the carbon to which they are attached form a spiro $C_3$cycloalkyl, and Y is a direct bond; and all other variables are as defined above for compounds of formula (I).

In another preferred embodiment, the invention provides a compound of formula (I) wherein A is selected from formula (V), and Z is N or S; and all other variables are as defined above for compounds of formula (I).

In yet another preferred embodiment, the invention provides a compound of formula (I) wherein X is a direct bond or —C($R_4$,$R_5$)—Y—, and A is represented by formula (V), and Z is N or S; and all other variables are as defined above for compounds of formula (I).

Outline of Method of Preparation of Compounds of the Invention

The imidazo[1,2-α]pyridine ether compounds of the present invention may contain various substituents ($R_2$, $R_{15}$, $R_{16}$ and $R_{18}$) on the imidazo[1,2-α]pyridine ring system and an ether side chain at position C8 as shown in formula (I). The present invention provides synthetic methodology whereby these compounds may be prepared. Compounds of the present invention may be prepared in analogy with known synthetic methodology (see, e.g., Bristol, James Arthur et al., EU Parent 0 068 378). For those having skill in the art, it is understood that for certain substrates containing other reactive functional groups, appropriate protective groups are employed in the synthesis. Suitable protective groups are set forth in, for example, Greene, "Protective Groups in Organic Chemistry", John Wiley & Sons, New York N.Y. (1991).

FIG. 1 outlines the reaction scheme for two synthetic routes A and B that may be used for the preparation of a compound in the present invention. The preparation of a compound of the invention may be achieved by following a three-step procedure.

In the first step of Route B (FIG. 1), the hydroxyl group of 2-amino-3-hydroxypyridine is converted into an alkoxide salt (i). Conversion of an alcohol to an alkoxide (also known as an alcoholate) using strong base is a general reaction, and may work for a wide variety of hydroxyl-containing compounds. The alkoxide is reacted with an activated alcohol (ii).

The activated alcohol (ii) is prepared according to procedures well known in the art. An "activated form" as used herein means that the hydroxyl group is converted into a good leaving group. The leaving group illustrated in FIG. 1 is a mesylate group (-OMs), which is a preferred leaving group. The hydroxyl group may also be converted into other leaving groups according to procedures well known in the art. In a typical reaction, the alcohol compound is treated with methanesulfonyl chloride (MsCl) in the presence of a base, such as triethylamine. The reaction is satisfactorily conducted at 0° C. An excess of the methanesulfonyl chloride, relative to the alcohol, is typically preferred to maximally convert the alcohol into the activated form. Such substrate alcohols are either commercially available or may be obtained by procedures in the art or adapted therefrom, where suitable procedures may be identified through the Chemicals Abstracts and Indices therefor, as developed and published by the American Chemical Society.

In the second step of Route B (FIG. 1), the alcoholate (i) is reacted with the activated alcohol (ii). Thus, generally stated, compounds of the present invention may be prepared by reacting an activated form of the selected alcohol (1 mol) with an alcoholate (1 mol) prepared by treatment of 2-amino-3-hydroxypyridine (1 mol) with, for example, sodium hydride (1.1 mol). The second alcohol (1 mol) may be activated by treatment with methanesulfonyl chloride (1.2 mol) and triethylamine (1.2 mol) to give the corresponding mesylate. The mesylate is added quickly to the alcoholate, in a suitable solvent such as anhydrous dimethylformamide (DMF) and the resultant reaction mixture is heated at 75° C. for 5 h. When the reaction has proceeded to substantial completion, the desired product is recovered from the reaction mixture by conventional organic chemistry techniques, and if necessary, can be purified by chromatography techniques.

In a third step, the substituted imidazo[1,2-α]pyridine is prepared by condensation of the above substituted 2-aminopyridine with α-halo carbonyl intermediates (see, e.g., Blewitt, H. L. in "Special Topics in Heterocyclic Chemistry"; Weissberger, A., Taylor, E. C., Eds.; Wiley: New York, 1977; p 117). When the reaction has proceeded to substantial completion, the desired product is recovered from the reaction mixture by conventional organic chemistry techniques. Removal of unreacted substituted 2-aminopyridine may be facilitated by its acetylation (acetic anhydride in pyridine) before separation from the desired substituted imidazo[1,2-α]pyridine product.

Alternatively, synthetic route A (FIG. 1) can be used to access compounds of the present invention. Route A is advantageous for structural variation in $R_{17}$ while $R_2$, $R_{15}$, $R_{16}$ and $R_{18}$ substitutions are maintained within a given series of analogues.

Once the imidazo[1,2-α]pyridine core has been assembled either via route A or B, further substitution at $R_{16}$ is possible. When $R_{16}$=H, the labile hydrogen can be substituted by a halogen, an amino group or an N,N-dimethylaminomethyl group (via a Mannich reaction). When $R_{16}$=$CO_2$Et, saponification and reduction can lead to the corresponding carboxylate and alcohol respectively.

The reaction sequence described above (FIG. 1) generates the imidazo[1,2-α]pyridine ether as the free base. The free base may be converted, if desired, to the monohydrochloride salt by known methodologies, or alternatively, if desired, to other acid addition salts by reaction with inorganic or organic acids. Acid addition salts can also be prepared metathetically by reaction of one acid addition salt with an acid that is stronger than that giving rise to the initial salt.

It is recognized that there may be one or more chiral centers in the compounds used within the scope of the present invention and thus such compounds will exist as various stereoisomeric forms. Applicants intend to include all the various stereoisomers within the scope of the invention. Though the compounds may be prepared as racemates and can conveniently be used as such, individual enantiomers also can be isolated or preferentially synthesized by known techniques if desired. Such racemates and individual enantiomers and mixtures thereof are intended to be included within the scope of the present invention. Pure enantiomeric forms if produced may be isolated by preparative chiral HPLC. The free base may be converted if desired, to the monohydrochloride salt by known methodologies, or alternatively, if desired, to other acid addition salts by reaction with other inorganic or organic acids. Acid addition salts can also be prepared metathetically by reacting one acid addition salt with an acid that is stronger than that of the anion of the initial salt.

The present invention also encompasses the pharmaceutically acceptable salts, esters, amides, complexes, chelates, solvates, crystalline or amorphous forms, metabolites, metabolic precursors or prodrugs of the compounds of formulae (I). Pharmaceutically acceptable esters and amides can be prepared by reacting, respectively, a hydroxy or amino functional group with a pharmaceutically acceptable organic acid, such as identified below. A prodrug is a drug which has been chemically modified and may be biologically inactive at its site of action, but which is degraded or modified by one or more enzymatic or other in vivo processes to the parent bioactive form. Generally, a prodrug has a different pharmakokinetic profile than the parent drug such that, for example, it is more easily absorbed across the mucosal epithelium, it has better salt formation or solubility and/or it has better systemic stability (e.g., an increased plasma half-life).

Those skilled in the art recognize that chemical modifications of a parent drug to yield a prodrug include: (1) terminal ester or amide derivatives which are susceptible to being cleaved by esterases or lipases; (2) terminal peptides which may be recognized by specific or nonspecific proteases; or (3) a derivative that causes the prodrug to accumulate at a site of action through membrane selection, and combinations of the above techniques. Conventional procedures for the selection and preparation of prodrug derivatives are described in H. Bundgaard, Design of Prodrugs, (1985). Those skilled in the art are well-versed in the preparation of prodrugs and are well-aware of its meaning.

The synthetic procedures described herein, especially when taken with the general knowledge in the art, provide sufficient guidance to those of ordinary skill in the art to perform the synthesis, isolation, and purification of the compounds of the present invention.

Compositions and Modes of Administration

In another embodiment, the present invention provides compositions which include an imidazo[1,2-α]pyridine compound as described above in admixture or otherwise in association with one or more inert carriers, excipients and diluents, as well as optional ingredients if desired. These compositions are useful as, for example, assay standards, convenient means of making bulk shipments, or pharmaceutical compositions. An assayable amount of a compound of the invention is an amount which is readily measurable by standard assay procedures and techniques as are well known and appreciated by those skilled in the art. Assayable amounts of a compound of the invention will generally vary from about 0.001 wt % to about 75 wt % of the entire weight of the composition. Inert carriers include any material which does not degrade or otherwise covalently react with a compound of the invention. Examples of suitable inert carriers are water; aqueous buffers, such as those which are generally useful in High Performance Liquid Chromatography (HPLC) analysis; organic solvents such as acetonitrile, ethyl acetate, hexane and the like (which are suitable for use in in vitro diagnostics or assays, but typically are not suitable for administration to a warm-blooded animal); and pharmaceutically acceptable carriers, such as physiological saline.

Thus, the present invention provides a pharmaceutical or veterinary composition (hereinafter, simply referred to as a pharmaceutical composition) containing an imidazo[1,2-α] pyridine compound as described above, in admixture with a pharmaceutically acceptable carrier, excipient or diluent. The invention further provides a pharmaceutical composition containing an effective amount of an imidazo[1,2-α] pyridine compound as described above, in association with a pharmaceutically acceptable carrier.

The pharmaceutical compositions of the present invention may be in any form which allows for the composition to be administered to a patient. For example, the composition may be in the form of a solid, liquid or gas (aerosol). Typical routes of administration include, without limitation, oral, topical, parenteral, sublingual, rectal, vaginal, and intranasal. The term parenteral as used herein includes subcutaneous injections, intravenous, intramuscular, epidural, intrasternal injection or infusion techniques. Pharmaceutical composition of the invention are formulated so as to allow the active ingredients contained therein to be bioavailable upon administration of the composition to a patient. Compositions that will be administered to a patient take the form of one or more dosage units, where for example, a tablet, capsule or cachet may be a single dosage unit, and a container of imidazo[1,2-α]pyridine compound in aerosol form may hold a plurality of dosage units.

Materials used in preparing the pharmaceutical compositions should be pharmaceutically pure and non-toxic in the amounts used. The inventive compositions may include one or more compounds (active ingredients) known for a particularly desirable effect. For instance, epinephrine may be combined with an imidazo[1,2-α]pyridine ether compound of the invention, to provide a composition useful to induce local anesthesia. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration and the composition employed.

In general, the pharmaceutical composition includes an imidazo[1,2-α]pyridine compound as described herein, in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, cachet, chewing gum, wafer, lozenges, or the like form. Such a solid composition will typically contain one or more inert diluents or edible carriers. In addition, one or more of the following adjuvants may be present: binders such as syrups, acacia, sorbitol, polyvinylpyrrolidone, carboxymethylcellulose, ethyl cellulose, microcrystalline cellulose, gum tragacanth or gelatin, and mixtures thereof; excipients such as starch, lactose or dextrins, disintegrating agents such as alginic acid, sodium alginate, Primogel, corn starch and the like; lubricants such as magnesium stearate or Sterotex; fillers such as lactose, mannitols, starch, calcium phosphate, sorbitol, methylcellulose, and mixtures thereof; lubricants such as magnesium stearate, high molecular weight polymers such as polyethylene glycol, high molecular weight fatty acids such as stearic acid, silica, wetting agents such as sodium lauryl sulfate, glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol or a fatty oil.

The composition may be in the form of a liquid, e.g., an elixir, syrup, solution, aqueous or oily emulsion or suspension, or even dry powders which may be reconstituted with water and/or other liquid media prior to use. The liquid may be for oral administration or for delivery by injection, as two examples. When intended for oral administration, preferred compositions contain, in addition to the present compounds, one or more of a sweetening agent, thickening agent, preservative (e.g., alkyl p-hydoxybenzoate), dye/colorant and flavor enhancer (flavorant). In a composition intended to be administered by injection, one or more of a surfactant, preservative (e.g., alkyl p-hydroxybenzoate), wetting agent, dispersing agent, suspending agent (e.g., sorbitol, glucose, or other sugar syrups), buffer, stabilizer and isotonic agent may be included. The emulsifying agent may be selected from lecithin or sorbitol monooleate.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid compositions intended for either parenteral or oral administration should contain an amount of the inventive compound such that a suitable dosage will be obtained. Typically, this amount is at least 0.01% of a compound of the invention in the composition. When intended for oral administration, this amount may be varied to be between 0.1 and about 70% of the weight of the composition. Preferred oral compositions contain between about 4% and about 50% of the active imidazo[1,2-α]pyridine compound. Preferred compositions and preparations according to the present invention are prepared so that a parenteral dosage unit contains between 0.01 to 10% by weight of active compound.

The pharmaceutical composition may be intended for topical administration, in which case the carrier may suitably comprise a solution, emulsion, ointment, cream or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the inventive compound of from about 0.1 to about 25% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol. Low-melting waxes are preferred for the preparation of a suppository, where mixtures of fatty acid glycerides and/or cocoa butter are suitable waxes. The waxes may be melted, and the imidazo[1,2-α]pyridine compound is dispersed homogeneously therein by stirring. The molten homogeneous mixture is then poured into convenient sized molds, allowed to cool and thereby solidify.

The composition may include various materials which modify the physical form of a solid or liquid dosage unit. For example, the composition may include materials that form a coating shell around the active ingredients. The materials which form the coating shell are typically inert, and may be selected from, for example, sugar, shellac, and other enteric coating agents. Alternatively, the active ingredients may be encased in a gelatin capsule or cachet.

The composition in solid or liquid form may include an agent which binds to the imidazo[1,2-α]pyridine compound and thereby assists in the delivery of the active components. Suitable agents which may act in this capacity include a monoclonal or polyclonal antibody, a protein or a liposome.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in methods for either modulating ion channel activity in a warm-blooded animal or for modulating ion channel activity in vitro, or used in the treatment or prevention of arrhythmia including atrial/supraventricular arrhythmia and ventricular arrhythmia, atrial fibrillation, ventricular fibrillation, atrial flutter, ventricular flutter, diseases of the central nervous system, convulsion, cardiovascular diseases (e.g. diseases caused by elevated blood cholesterol or triglyceride levels), cerebral or myocardial ischemias, hypertension, long-QT syndrome, stroke, migraine, ophthalmic diseases, diabetes mellitus, myopathies, Becker's myotonia, myasthenia gravis, paramyotonia congentia, malignant hyperthermia, hyperkalemic periodic paralysis, Thomsen's myotonia, autoimmune disorders, graft rejection in organ transplantation or bone marrow transplantation, heart failure, hypotension, Alzheimer's disease, dementia and other mental disorders, alopecia, sexual dysfunction, impotence, demyelinating diseases, multiple sclerosis, amyotrophic lateral sclerosis, epileptic spasms, depression, anxiety, schizophrenia, Parkinson's disease, respiratory disorders, cystic fibrosis, asthma, cough, inflammation, arthritis, allergies, urinary incontinence, irritable bowel syndrome, and gastrointestinal disorders such as gastrointestinal inflammation and ulcer. Other agents known to cause libido enhancement, analgesia or local anesthesia may be combined with compounds of the present invention.

The pharmaceutical compositions may be prepared by methodology well known in the pharmaceutical art. The imidazo[1,2-α]pyridine compounds of the invention may be in the form of a solvate in a pharmaceutically acceptable solvent such as water or physiological saline. Alternatively, the compounds may be in the form of the free base or in the form of a pharmaceutically acceptable salt such as the hydrochloride, sulfate, phosphate, citrate, fumarate, methanesulfonate, acetate, tartrate, maleate, lactate, mandelate, salicylate, succinate and other salts known in the art. The appropriate salt would be chosen to enhance bioavailability and/or stability of the compound for the appropriate mode of employment (e.g., oral or parenteral routes of administration).

A composition intended to be administered by injection can be prepared by combining an imidazo[1,2-α]pyridine compound with water, and preferably buffering agents, so as to form a solution. The water is preferably sterile pyrogen-free water. A surfactant may be added to facilitate the formation of a homogeneous solution or suspension. Surfactants are compounds that non-covalently interact with the imidazo[1,2-α]pyridine compound so as to facilitate dissolution or homogeneous suspension of the imidazo[1,2-α]pyridine compound in the aqueous delivery system. Surfactants are desirably present in aqueous compositions of the invention because the imidazo[1,2-α]pyridine compounds of the present invention are typically hydrophobic. Other carriers for injection include, without limitation, sterile peroxide-free ethyl oleate, dehydrated alcohols, propylene glycol, as well as mixtures thereof.

Suitable pharmaceutical adjuvants for the injecting solutions include stabilizing agents, solubilizing agents, buffers, and viscosity regulators. Examples of these adjuvants include ethanol, ethylenediaminetetraacetic acid (EDTA), tartrate buffers, citrate buffers, and high molecular weight polyethylene oxide viscosity regulators. These pharmaceutical formulations may be injected intramuscularly, epidurally, intraperitoneally, or intravenously.

Pharmacological Aspects

As noted above, the present invention provides for utilizing the compounds described above in in vitro and in vivo methods. In one embodiment, ion channels, such as cardiac potassium channels, are blocked in vitro or in vivo.

Ion channels are ubiquitous membrane proteins in the cells of warm-blooded animals such as mammals. Their critical physiological roles include control of the electrical potential across the membrane, mediation of ionic and fluid balance, facilitation of neuromuscular and neuronal transmission, rapid transmembrane signal transduction, and regulation of secretion and contractility.

Accordingly, compounds that are capable of modulating the activity or function of the appropriate ion channels will be useful in treating and/or preventing a variety of diseases or disorders caused by defective or inadequate function of the ion channels. The compounds of the invention are found to have significant activity in modulating various ion channel activity both in vivo and in vitro.

In one aspect, the present invention provides a compound of formula (I) or composition containing a compound of formula (I), for use in methods for either modulating ion channel activity in a warm-blooded animal or for modulating ion channel activity in vitro. Some of the ion channels to which the compounds, compositions and methods of the present invention have modulating effect are various potassium and sodium channels. These potassium and sodium ion channels may be voltage-activated (also known as voltage-gated) or ligand-activated (also known as ligand-gated), and may be present in cardiac and/or neuronal systems.

In another aspect, the present invention provides a compound of formula (I) or composition containing a compound of formula (I), for use in methods for either modulating activity of ion channel(s) in a warm-blooded animal or for modulating activity of ion channel(s) in vitro, wherein said ion channel(s) correspond to some of the cardiac and/or neuronal ion channels that are responsible for one or more early repolarising currents comprising those which activate rapidly after membrane depolarisation and which effect repolarisation of the cells.

In another aspect of the present invention, the above-mentioned early repolarising currents comprise the transient outward potassium current ($I_{to}$ for cardiac or $I_A$ for neuronal) and/or the ultrarapid delayed rectifier current ($I_{Kur}$); and include at least one of the Kv4.2, Kv4.3, Kv2.1, Kv1.3, Kv1.4 and Kv1.5 currents.

In another aspect, the present invention provides a compound of formula (I) or composition containing a compound of formula (I), for use in methods for either modulating activity of ion channel(s) in a warm-blooded animal or for modulating activity of ion channel(s) in vitro, wherein said ion channel(s) correspond to either the cardiac or neuronal ion channel(s) that are responsible for Kv1.5 currents.

In yet another aspect, the present invention provides a compound of formula (I) or composition containing a compound of formula (I), for use in methods for either modulating activity of ion channel(s) in a warm-blooded animal or for modulating activity of ion channel(s) in vitro, wherein said ion channel(s) correspond to the potassium channel encoded by the human ether-a-go-go related gene (HERG).

Furthermore, the voltage-activated sodium ion channels comprise the $Na_v1$, $Na_v2$ or $Na_v3$ series and may be present in cardiac, neuronal, skeletal muscle, central nervous and/or peripheral nervous systems.

As noted earlier, modulating the activity of an ion channel as used above may imply but does not limit to blocking or inhibiting the conductance of the current through the ion channel.

Thus, the present invention provides for methods of treating a disease or condition in a warm-blooded animal suffering from or having the disease or condition, and/or preventing a disease or condition from arising in a warm-blooded animal, wherein a therapeutically effective amount of a compound of formula (I), or a composition containing a compound of formula (I) is administered to a warm-blooded animal in need thereof. Some of the diseases and conditions to which the compounds, compositions and methods of the present invention may be applied are as follows: arrhythmia including atrial/supraventricular arrhythmia and ventricular arrhythmia, atrial fibrillation, ventricular fibrillation, atrial flutter, ventricular flutter, diseases of the central nervous system, convulsion, cardiovascular diseases (e.g. diseases caused by elevated blood cholesterol or triglyceride levels), cerebral or myocardial ischemias, hypertension, long-QT syndrome, stroke, migraine, ophthalmic diseases, diabetes mellitus, myopathies, Becker's myotonia, myasthenia gravis, paramyotonia congentia, malignant hyperthermia, hyperkalemic periodic paralysis, Thomsen's myotonia, autoimmune disorders, graft rejection in organ transplantation or bone marrow transplantation, heart failure, hypotension, Alzheimer's disease, dementia and other mental disorder, alopecia, sexual dysfunction, impotence, demyelinating diseases, multiple sclerosis, amyotrophic lateral sclerosis, epileptic spasms, depression, anxiety, schizophrenia, Parkinson's disease, respiratory disorders, cystic fibrosis, asthma, cough, inflammation, arthritis, allergies, urinary incontinence, irritable bowel syndrome, and gastrointestinal disorders such as gastrointestinal inflammation and ulcer.

Furthermore, the present invention provides a method for producing analgesia or local anesthesia in a warm-blooded animal which includes administering to a warm-blooded animal in need thereof an effective amount of a compound of formula (I) or a pharmaceutical composition containing a compound of formula (I). These methods may be used to relieve or forestall the sensation of pain in a warm-blooded animal.

The invention further provides a method for enhancing libido in a warm-blooded animal which includes administering to a warm-blooded animal in need thereof an effective amount of a compound of formula (I) or a pharmaceutical composition containing a compound of formula (I). These compositions and methods may be used, for example, to treat a sexual dysfunction, e.g., impotence in males, and/or to enhance the sexual desire of a patient without a sexual dysfunction. As another example, the therapeutically effective amount may be administered to a bull (or other breeding stock), to promote increased semen ejaculation, where the ejaculated semen is collected and stored for use as it is needed to impregnate female cows in promotion of a breeding program.

Furthermore, the present invention provides a method in an in vitro setting, wherein a preparation that contains ion channels is contacted with an effective amount of an imidazo[1,2-α]pyridine ether compound of the invention. Suitable preparations containing cardiac sodium channels include cells isolated from cardiac tissue as well as cultured cell lines. The step of contacting includes, for example, incubation of ion channels with a compound under conditions and for a time sufficient to permit modulation of the activity of the channels by the compound.

In another embodiment, the compounds described above are provided for treating arrhythmia. As used herein, "treating arrhythmia" refers to both therapy for arrhythmia and for the prevention of arrhythmias occurring in a heart that is susceptible to arrhythmia. An effective amount of a composition of the present invention is used to treat arrhythmia in a warm-blooded animal, such as a human. Methods of administering effective amounts of antiarrhythmic agents are well known in the art and include the administration of an oral or parenteral dosage form. Such dosage forms include, but are not limited to, parenteral dosage form. Such dosage forms include, but are not limited to, parenteral solutions, tablets, capsules, sustained release implants, and transdermal delivery systems. Generally, oral or intravenous administration is preferred. The dosage amount and frequency are selected to create an effective level of the agent without harmful effects. It will generally range from a dosage of from about 0.01 to about 100 mg/kg/day, and typically from about 0.1 to 10 mg/kg where administered orally or intravenously for antiarrhythmic effect.

Administration of compositions of the present invention may be carried out in combination with the administration of other agents. For example, it may be desired to administer an opioid antagonist, such as naloxone, if a compound exhibits opioid activity where such activity may not be desired. The naloxone may antagonize opioid activity of the administered compound without adverse interference with the antiarrhythmic activity. As another example, an imidazo[1,2-α]pyridine ether compound of the invention may be co-administered with epinephrine in order to induce local anesthesia.

In order to assess whether a compound has a desired pharmacological activity with the present invention, it is subjected to a series of tests. The precise test to employ will depend on the physiological response of interest. The published literature contains numerous protocols for testing the efficacy of a potential therapeutic agent, and these protocols may be employed with the present compounds and compositions.

For example, in connection with treatment or prevention of arrhythmia, a series of four tests may be conducted. In the first of these tests, a compound of the present invention is given as increasing (doubling with each dose) intravenous infusion every 5 minutes to a conscious rat. The effects of the compound on blood pressure, heart rate and the ECG are measured continuously. Increasing doses are given until a severe adverse event occurs. The drug related adverse event is identified as being of respiratory, central nervous system or cardiovascular system origin. This test gives an indication as to whether the compound is modulating the activity of sodium channels and/or potassium channels, and in addition gives information about acute toxicity. The indices of sodium channel blockade are increasing P-R interval and QRS widening of the ECG. Potassium channel blockade results in Q-T interval prolongation of the ECG.

A second test involves administration of a compound as an infusion to pentobarbital anesthetized rats in which the left ventricle is subjected to electrical square wave stimulation performed according to a preset protocol described in further detail below. This protocol includes the determination of thresholds for induction of extrasystoles and ventricular fibrillation. In addition, effects on electrical refractoriness are assessed by a single extra beat technique. In addition effects on blood pressure, heart rate and the ECG are recorded. In this test, sodium channel blockers produce the ECG changes expected from the first test. In addition, sodium channel blockers also raise the thresholds for induction of extrasystoles and ventricular fibrillation. Potassium channel blockade is revealed by increasing refractoriness and widening of the Q-T intervals of the ECG.

A third test involves exposing isolated rat hearts to increasing concentrations of a compound. Ventricular pressures, heart rate, conduction velocity and ECG are recorded in the isolated heart in the presence of varying concentrations of the compound. The test provides evidence for direct toxic effects on the myocardium. Additionally, selectivity, potency and efficacy of action of a compound can be ascertained under conditions simulating ischemia. Concentrations found to be effective in this test are expected to be efficacious in the electrophysiological studies.

A fourth test is estimation of the antiarrhythmic activity of a compound against the arrhythmias induced by coronary artery occlusion in anaesthetized rats. It is expected that a good antiarrhythmic compound will have antiarrhythmic activity at doses which have minimal effects on either the ECG, blood pressure or heart rate under normal conditions.

All of the foregoing tests are performed using rat tissue. In order to ensure that a compound is not having effects which are only specific to rat tissue, further experiments are performed in dogs and primates. In order to assess possible sodium channel and potassium channel blocking action in vivo in dogs, a compound is tested for effects on the ECG, ventricular epicardial conduction velocity and responses to electrical stimulation. An anesthetized dog is subjected to an open chest procedure to expose the left ventricular epicardium. After the pericardium is removed from the heart a recording/stimulation electrode is sewn onto the epicardial surface of the left ventricle. Using this array, and suitable stimulation protocols, conduction velocity across the epicardium as well as responsiveness to electrical stimulation can be assessed. This information coupled with measurements of the ECG allows one to assess whether sodium and/or potassium channel blockade occurs. As in the first test in rats, a compound is given as a series of increasing bolus doses. At the same time possible toxic effects of a compound on the dog's cardiovascular system is assessed.

The effects of a compound on the ECG and responses to electrical stimulation are also assessed in intact, anesthetized monkeys (*Macaca fascicularis*). In this preparation, a blood pressure cannula and ECG electrodes are suitably placed in an anesthetized monkey. In addition, a stimulating electrode is placed onto the right atria and/or ventricle, together with monophasic action potential electrode. As in the tests described above, ECG and electrical stimulation response to a compound reveal the possible presence of sodium and/or potassium channel blockade. The monophasic action potential also reveals whether a compound widens the action potential, an action expected of a potassium channel blocker.

As another example, in connection with the mitigation or prevention of the sensation of pain, the following test may be performed. To determine the effects of a compound of the present invention on an animal's response to a sharp pain sensation, the effects of a slight prick from a 7.5 g weighted syringe fitted with a 23G needle as applied to the shaved back of a guinea pig (*Cavia porcellus*) is assessed following subcutaneous administration of sufficient (50 μl, 10 mg/ml) solution in saline to raise a visible bleb on the skin. Each test is performed on the central area of the bleb and also on its periphery to check for diffusion of the test solution from the point of administration. If the test animal produces a flinch in response to the stimulus, this demonstrates the absence of blockade of pain sensation. Testing may be carried out at intervals for up to 8 hours or more post-administration. The sites of bleb formation are examined after 24 hours to check for skin abnormalities consequent to local administration of test substances or of the vehicle used for preparation of the test solutions.

Other Compositions

The present invention also provides kits that contain a pharmaceutical composition which includes one or more compounds of the above formulae. The kit also includes instructions for the use of the pharmaceutical composition for modulating the activity of ion channels, for the treatment of arrhythmia or for the production of analgesia and/or local anesthesia, and for the other utilities disclosed herein. Preferably, a commercial package will contain one or more unit doses of the pharmaceutical composition. For example, such a unit dose may be an amount sufficient for the preparation of an intravenous injection. It will be evident to those of ordinary skill in the art that compounds which are light and/or air sensitive may require special packaging and/or formulation. For example, packaging may be used which is opaque to light, and/or sealed from contact with ambient air, and/or formulated with suitable coatings or excipients.

The following examples are offered by way of illustration and not by way of limitation. In the Examples, and unless otherwise specified, starting materials were obtained from well-known commercial supply houses, e.g., Aldrich Chemical Company (Milwaukee, Wis.), and were of standard grade and purity. "Ether" and "ethyl ether" each refers to diethyl ether; "h" refers to hours; "min" refers to minutes; "GC" refers to gas chromatography; "v/v" refers to volume per volume; and ratios are weight ratios unless otherwise indicated.

EXAMPLES

Example 1

8-[3-(2,4-Dichlorophenyl)Propoxy]-2-Methylimidazo [1,2-α]Pyridine Monohydrochloride

Compound 1

Route B:

1) To a cold (0° C.) solution of 3-(2,4-dichlorophenyl)-1-propanol (4.3 g, 20 mmol) and triethylamine (3.4 mL, 24 mmol) in dichloromethane (80 mL) was added dropwise neat methanesulfonyl chloride (1.9 mL, 24 mmol) under argon. The resultant mixture was stirred at 0° C. for 1 h and then at ambient temperature for 1.5 h. The reaction mixture was then diluted with dichloromethane (40 mL) and washed with water (2×60 mL). The organic layer was dried over anhydrous sodium sulfate and concentrated in vacuo to yield the desired mesylate, which was used in the next step without further purification.

2) To sodium hydride (0.6 g, 80% oil dispersion) and 2-amino-3-hydroxypyridine (2.25 g, 20 mmol) was added anhydrous dimethylformamide (90 mL) and the resultant mixture was stirred at ambient temperature for 1 h under argon.

3) To the alkoxide (step 2) was quickly added a solution of the mesylate (step 1) in anhydrous dimethylformamide (15 mL) and the resultant mixture was heated at 75° C. for 2.5 h. The cooled reaction mixture was poured into ice water (300 mL) and extracted with ethyl acetate (3×150 mL). The organic extracts were combined, back-washed with brine (4×100 mL), dried over anhydrous sodium sulfate and concentrated in vacuo to yield the crude desired product. Purification by dry column (600 mL funnel, silica gel 10–40μ, Sigma cat. S-6628) with a mixture of ethyl acetate-hexanes (1:2 v/v, containing 0.5% v/v isopropylamine) yielded 4.77 g (80% yield) of 2-amino-3-[3-(2,4-dichlorophenyl)propoxy]pyridine ($R_f$=0.34 in ethyl acetate-hexanes, 2:1 v/v, containing 0.5% v/v isopropylamine).

A mixture of 2-amino-3-[3-(2,4-dichlorophenyl)propoxy]pyridine (4.73 g, 15.9 mmol, step 3), chloroacetone (5.1 mL, 64.0 mmol) and molecular sieves (6.0 g, type 4 Å, beads, 8–12 mesh) in anhydrous methanol (150 mL) was refluxed for 20 h. The molecular sieves were filtered off and the filtrate was concentrated in vacuo to yield the crude title compound. The residual oil was triturated in ethanol and the solvent was evaporated in vacuo to yield a yellow solid. Recrystallization in a mixture of ethanol-diethyl ether (20:80, v/v, 100 mL) provided a first crop (3.25 g, 55% yield). Concentration in vacuo of the mother liquor and subsequent recrystallization in a mixture of ethanol-diethyl ether (14:86, v/v, 60 mL) yielded a second crop (0.64 g, 11% yield). 191° C.<mp<193° C.; $^1$H-NMR (400 MHz, $CDCl_3$) δ 11.10 (br s, 1H, $^+$NH), 8.30 (d, 1H, Ar), 7.90 (s, 1H, Ar), 7.50 (d, 1H, Ar), 7.20 (s, 1H, Ar), 7.05 (m, 2H, Ar), 6.90 (d, 1H, Ar), 4.15 (t, 2H, $CH_2O$), 3.15 (t, 2H, $CH_2Ar$), 2.65 (s, 3H, $CH_3$), 2.20 (m, 2H, $CH_2$); $^{13}$C-NMR (75 MHz, $CDCl_3$, APT) δ 144.61 (+), 137.42 (+), 134.71 (+), 134.27 (+), 133.07 (+), 132.35 (–), 132.06 (+), 128.70 (–), 127.00 (–), 119.65 (–), 116.79 (–), 112.36 (–), 108.47 (–), 68.75 (+), 29.13 (+), 28.39 (+), 10.63 (–); LRMS-FAB m/z: $MH^+$ 335 (100%); HRMS-FAB (m/z): $[M+H]^+$ calcd for $C_{17}H_{17}N_2OCl_2$: 335.07179. found: 335.07262; Anal. calcd for $C_{17}H_{16}N_2OCl_2$.HCl: C, 54.93; H, 4.61; N, 7.54%. found: C, 54.41; H, 4.55; N, 7.37%.

Example 2

2-Methyl-8-[3-Phenylpropoxy]imidazo[1,2-α]Pyridine Monohydrochloride

Compound 2

Route B:

1) To sodium hydride (0.79 mg, 80% oil dispersion) and 2-amino-3-hydroxypyridine (3.30 g, 10 mmol) was added anhydrous dimethylformamide (90 mL) and the resultant mixture was stirred at ambient temperature for 30 min under argon.

2) To the alkoxide (step 1) was added 1-bromo-3-phenylpropane (4.0 mL, 33.0 mmol) and the resultant mixture was stirred at room temperature for 20 h. The reaction mixture was poured into water (400 mL) and extracted with ethyl acetate (3×150 mL). The organic extracts were combined, back-washed with brine (200 mL), dried over anhydrous sodium sulfate and concentrated in vacuo to yield 6.47 g of the crude desired product (94% yield). $R_f$=0.31 (ethyl acetate-hexanes, 1:2 v/v, containing 0.5% v/v isopropylamine).

3) A mixture of 2-amino-3-(3-phenylpropoxy)pyridine (6.42 g, 28.0 mmol, step 2), chloroacetone (2.9 mL, 36.0 mmol) in anhydrous methanol (100 mL) was refluxed for 24 h. The solvent was concentrated in vacuo and the residue was partitioned between ethyl acetate (100 mL) and saturated aq sodium bicarbonate (150 mL). The aqueous layer was extracted thrice more with ethyl acetate (3×100 mL), and the organic extracts were combined, dried over anhydrous sodium sulfate and concentrated in vacuo to yield the crude title compound. The unreacted 2-amino-3-(3-phenylpropoxy)pyridine was acetylated by reflux with acetic anhydride (0.7 mL) in anhydrous pyridine (25 mL) for one h. The pyridine was evaporated in vacuo, the residue was taken up with 1M aq HCl (100 mL) and the resultant acidic aqueous solution was extracted with diethyl ether (100 mL). The aqueous layer was adjusted to pH 5.3 and extracted with diethyl ether (100 mL) and the ether layer was dried over anhydrous sodium sulfate. After filtrative removal of the drying agent, the filtrate was treated with ethereal hydrogen chloride to provide the title compound as a hygroscopic product. $^1$H-NMR (400 MHz, $CDCl_3$) δ 15.50 (br s, 1H, $^+$NH), 8.45 (d, 1H, Ar), 8.00 (s, 1H, Ar), 7.20–6.90 (m, 6H, Ar), 6.80 (d, 1H, Ar), 4.05 (t, 2H, $CH_2O$), 2.90 (t, 2H, $CH_2Ar$), 2.50 (s, 3H, $CH_3$), 2.10 (m, 2H, $CH_2$); $^{13}$C-NMR (75 MHz, $CDCl_3$, APT) δ 144.26 (+), 140.89 (+), 134.06 (+), 132.79 (+), 128.32 (−), 127.94 (−), 125.53 (−), 119.97 (−), 116.65 (−), 112.61 (−), 108.54 (−), 68.64 (+), 31.45 (+), 30.02 (+), 10.44 (−); LRMS-EI m/z: $M^+$ 266 (11.94%), HRMS-EI (m/z): $[M]^+$ calcd for $C_{17}H_{18}N_2O$: 266.14191. found: 266.14133 (23.30%).

Example 3

8-[3-(3,4-Dimethoxyphenyl)Propoxy]-2-Methylimidazo[1,2-α]Pyridine Monohydrochlorde Compound 3

Route B:

1) To a cold (0° C.) solution of 3-(3,4-dimethoxyphenyl)-1-propanol (1.98 g, 10 mmol) and triethylamine (1.7 mL, 12 mmol) in dichloromethane (40 mL) was added dropwise neat methanesulfonyl chloride (0.95 mL, 12 mmol) under argon. The resultant mixture was stirred at 0° C. for 1 h and then at ambient temperature overnight. The reaction mixture was then diluted with dichloromethane (40 mL) and washed with water (2×40 mL). The organic layer was dried over anhydrous sodium sulfate and concentrated in vacuo to yield the desired mesylate, which was used in the next step without further purification.

2) To sodium hydride (0.3 g, 10 mmol, 80% oil dispersion) and 2-amino-3-hydroxypyridine (1.12 g, 10 mmol) was added anhydrous dimethylformamide (45 mL) and the resultant mixture was stirred at ambient temperature for 1 h under argon.

3) To the alkoxide (step 2) was quickly added a solution of the mesylate (step 1) in anhydrous dimethylformamide (20 mL) and the resultant mixture was heated at 75° C. for 3 h. The cooled reaction mixture was poured into ice water (100 mL) and extracted with ethyl acetate (2×150 mL). The organic extracts were combined, back-washed with brine (5×100 mL), dried over anhydrous sodium sulfate and concentrated in vacuo to yield the crude desired product as a light brown solid. The crude product was triturated in diethyl ether (20 mL), and the resultant solid was collected, rinsed with diethyl ether and dried in vacuo to yield 2.30 g (80% yield) of 2-amino-3-[3-(3,4-dimethoxyphenyl)propoxy]pyridine.

A mixture of 2-amino-3-[3-(3,4-dimethoxyphenyl)propoxy]pyridine (2.15 g, 7.46 mmol, step 3), chloroacetone (2.56 mL, 30.5 mmol) and molecular sieves (6.0 g, type 4 Å, beads, 8–12 mesh) in anhydrous methanol (100 mL) was refluxed for 4 days. The molecular sieves were filtered off and the filtrate was concentrated in vacuo to yield the crude title compound. The residual oil was treated with 1M aq HCl (100 mL) and extracted with diethyl ether (2×100 mL). The aqueous layer was adjusted to pH 14 with 40% aq NaOH and extracted with diethyl ether (3×100 mL). The ether extracts (pH 14) were combined, back-washed with water (2×100 mL), dried over anhydrous sodium sulfate and concentrated in vacuo to provide the free base of the title compound. The free base was then dissolved in dichloromethane-diethyl ether (1:5, v/v, 120 mL) and treated with ethereal hydrogen chloride. After the solvent was evaporated in vacuo, the residue was triturated in diethyl ether (150 mL) to give the title compound as a pale yellow powder (1.08 g, 30% yield). $^{13}$C-NMR (100 MHz, $CDCl_3$, APT) δ 148.88, 147.16, 144.70, 134.56, 133.98, 133.19, 120.32, 119.80, 116.67, 112.63, 112.52, 111.44, 108.63, 69.08, 55.98, 55.88, 31.29, 30.49, 10.48; LRMS-FAB m/z: $MH^+$ 327 (100%); HRMS-FAB (m/z): $[M+H]^+$ calcd for $C_{19}H_{23}O_3N_2$: 327.17087. found: 327.17068.

Example 4

8-[3-(2,4-Dichlorophenyl)Propoxy]-2-Ethylimidazo[1,2-α]Pyridine Monohydrochloride Compound 4

Route B:

A mixture of 2-amino-3-[3-(2,4-dichlorophenyl)propoxy]pyridine (1.5 g, 5.05 mmol, see example 1), 1-bromo-2-butanone (3.39 g, 20.2 mmol) and molecular sieves (4.0 g, type 4 Å, beads, 8–12 mesh) in anhydrous methanol (80 mL) was refluxed for 16 h. The molecular sieves were filtered off and the filtrate was concentrated in vacuo. The residual oil was dissolved in 1M aq HCl (100 mL) and extracted with diethyl ether (3×100 mL). The aqueous layer was adjusted to pH 14 with 40% aq sodium hydroxide and then extracted with diethyl ether (2×150 mL). The diethyl ether extracts (pH 14) were combined, washed with saturated aq sodium bicarbonate (100 mL) and water (100 mL), dried over anhydrous sodium sulfate and concentrated in vacuo to yield the free base of the title compound. The free base was dissolved in diethyl ether (60 mL) and treated with ethereal hydrogen chloride to give the title compound as a powder (1.03 g, 53% yield). $^{1}$H-NMR (400 MHz, $CD_3OD$) δ 15.96 (s, 1H, $^{+}$NH), 8.30 (d, 1H, Ar), 7.84 (s, 1H, Ar), 7.52 (d, 1H, Ar), 7.19 (d, 1H, Ar), 7.12–6.96 (m, 2H, Ar), 6.87 (d, 1H, Ar), 4.13 (t, 2H, $CH_2O$), 3.12 (t, 2H, $CH_2Ar$), 3.05 (q, 2H, $CH_2CH_3$), 2.19 (m, 2H, $CH_2$), 1.35 (t, 3H, $CH_3$); $^{13}$C-NMR (100 MHz, $CD_3OD$, APT) δ 144.79 (+), 140.91 (+), 137.49 (+), 134.29 (+), 133.24 (+), 132.42 (−), 132.06 (+), 128.71 (−), 127.01 (−), 119.75 (−), 116.80 (−), 111.32 (−), 108.50 (−), 68.86 (+), 29.15 (+), 28.42 (+), 18.68 (+), 12.74 (−); LRMS-FAB m/z: $MH^+$ 349 (100%); HRMS-FAB (m/z): $[M+H]^+$ calcd for $C_{18}H_{19}ON_2Cl_2$: 349.08744. found: 349.08769; Anal. calcd for $C_{18}H_{18}N_2OCl_2$.HCl: C, 56.05; H, 4.96; N, 7.26%, found: C, 55.95; H, 4.94; N, 6.90%.

Example 5

8-[3-(2,4-Dichlorophenyl)Propoxy]-2-Phenylimidazo[1,2-α]Pyridine Monohydrochloride

Compound 5

Route B:

A mixture of 2-amino-3-[3-(2,4-dichlorophenyl)propoxy]pyridine (1.5 g, 5.05 mmol, see example 1), 2-chloroacetophenone (2.4 mL, 20.2 mmol), potassium iodide (16.8 mg, 0.1 mmol) and molecular sieves (4.0 g, type 4 Å, beads, 8–12 mesh) in anhydrous methanol (80 mL) was refluxed for 3.5 days. The molecular sieves were filtered off and the filtrate was concentrated in vacuo. The residual oil was treated with 1M aq HCl solution (40 mL) to give the crude product as a yellow solid. The solid was treated with saturated aq $NaHCO_3$ (100 mL) and the resultant mixture was extracted with ethyl acetate (2×100 mL). The organic extracts were combined, washed with water, dried over anhydrous sodium sulfate and concentrated in vacuo to give the title compound as a free base. After purification by dry column (150 mL funnel, silica gel 10–40μ, Sigma cat. S-6628) eluted with a mixture of ethyl acetate-hexanes (1:1 v/v, containing 0.5% v/v isopropylamine), the free base was dissolved in diethyl ether (60 mL) and treated with ethereal hydrogen chloride to give the title compound as a powder (1.26 g, 58% yield). $^{1}$H-NMR (400 MHz, $CDCl_3$) δ 8.55 (s, 1H, Ar), 8.40 (s, 1H, Ar), 7.92 (s, 1H, Ar), 7.91 (s, 1H, Ar), 7.56 (m, 3H, Ar), 7.38 (m, 4H, Ar), 7.24 (s, 1H, Ar), 4.42 (s, 2H, $CH_2O$), 3.29 (s, 2H, $CH_2Ar$), 2.30 (s, 2H, $CH_2$); $^{13}$C-NMR (100 MHz, $CDCl_3$, APT) δ 145.82 (+), 138.86 (+), 138.02 (+), 136.06 (+), 135.71 (+), 133.69 (+), 132.99 (−), 131.79 (−), 130.58 (−), 130.09(−), 128.46 (-), 128.15 (−), 127.48 (+), 122.11 (−), 119.31 (−), 113.58 (−), 112.43 (−), 70.69 (+), 30.21 (+), 29.54 (+); LRMS-FAB m/z: $MH^+$ 397 (100%); HRMS-FAB (mz/z): $[M+H]^+$ calcd for $C_{22}H_{19}ON_2Cl_2$: 397.08744. found: 397.08716. Anal. calcd for $C_{22}H_{18}N_2OCl_2$.HCl: C, 60.92; H, 4.42; N, 6.46%. found: C, 59.16; H, 4.50; N, 6.02%.

Example 6

8-[3-(2,6-Dichlorophenyl)Propoxy]-2-Methylimidazo[1,2-α]Pyridine Monohydrochloride

Compound 6

Route B:

1) To a cold (0° C.) solution of 3-(2,6-dichlorophenyl)-1-propanol (1.64 g, 8 mmol) and triethylamine (1.35 mL, 9.6 mmol) in dichloromethane (40 mL) was added dropwise neat methanesulfonyl chloride (0.76 mL, 9.6 mmol) under argon. The resultant mixture was stirred at 0° C. for 30 min and then at ambient temperature for 2 h. The reaction mixture was then diluted with dichloromethane (20 mL) and washed with water (2×30 mL). The organic layer was dried over anhydrous sodium sulfate and concentrated in vacuo to yield the desired mesylate, which was used in the next step without further purification.

2) To sodium hydride (0.24 g, 8 mmol, 80% oil dispersion) and 2-amino-3-hydroxypyridine (0.90 g, 8 mmol) was added anhydrous dimethylformamide (40 mL) and the resultant mixture was stirred at ambient temperature for 1 h under argon.

3) To the alkoxide (step 2) was quickly added a solution of the mesylate (step 1) in anhydrous dimethylformamide (25 mL) and the resultant mixture was heated at 75° C. for 3 h. The cooled reaction mixture was poured into ice water (150 mL) and extracted with ethyl acetate (150 mL, 100 mL). The organic extracts were combined, back-washed with brine (4×150 mL), dried over anhydrous sodium sulfate, and filtered through a charcoal bed (0.5 cm thick, 8.5 cm of diameter). The charcoal was washed with toluene (350 mL) and the filtrate was concentrated in vacuo to yield 1.9 g (80% yield) of 2-amino-3-[3-(2,6-dichlorophenyl)propoxy]pyridine as greenish yellow crystals ($R_f$=0.5 in ethyl acetate-hexanes, 2:1 v/v, containing 1% v/v isopropylamine).

A mixture of 2-amino-3-[3-(2,6-dichlorophenyl)propoxy]pyridine (1.4 g, 4.7 mmol, step 3), chloroacetone (1.6 mL, 18.8 mmol) and molecular sieves (5.0 g, type 4 Å, beads, 8–12 mesh) in anhydrous methanol (80 mL) was refluxed for 3 days. The molecular sieves were filtered off and the filtrate was concentrated in vacuo to yield the crude title compound as an oil. The residual oil was dissolved in water (120 mL) and the resultant solution was adjusted to pH 14 with 40% aq sodium hydroxide and extracted with diethyl ether (2×120 mL). The diethyl ether extracts were combined, dried over anhydrous sodium sulfate and concentrated in vacuo to yield the crude free base of the title compound. After purification by dry column (150 mL funnel, silica gel 10–40μ, Sigma cat. S-6628) eluted with mixtures of ethyl acetate-hexanes (1:5–1:4 v/v, containing 0.5% v/v isopropylamine), the free base was dissolved in ethyl acetate (50 mL) and the resultant solution was treated with HCl-saturated ethyl acetate (20 mL). Evaporation of the solvent in vacuo gave an oil, which was triturated in diethyl ether (150 mL) to afford the title compound as a solid (0.76 g, 44% yield). $^{1}$H-NMR (400 MHz, $CDCl_3$) δ 15.56 (br s, 1H, $^{+}$NH), 8.51 (s, 1H, Ar), 8.06 (s, 1H, Ar), 7.15–6.81 (m, 5H, Ar), 4.16 (t, 2H, $CH_2O$), 3.07 (t, 2H, $CH_2Ar$), 2.57 (s, 3H, $CH_3$), 2.20 (m, 2H, $CH_2$); $^{13}$C-NMR (100 MHz, $CDCl_3$, APT) δ 144.35 (+), 136.74 (+), 135.14 (+), 134.44 (+), 133.10 (+), 128.03 (−), 127.87 (−), 120.35 (−), 116.67 (−), 112.85 (−), 108.92 (−), 69.03 (+), 27.07 (+), 27.01 (+), 10.61 (−);

LRMS-FAB m/z: $MH^+$ 335 (100%); HRMS-FAB (m/z): $[M+H]^+$ calcd for $C_{17}H_{17}N_2OCl_2$: 335.07179. found: 335.07165.

Example 7

2-Methyl-8-[2-(Trifluoromethyl)Benzyloxy]imidazo [1,2-α]Pyridine Monohydrochloride Compound 7

Route B:

1) To sodium hydride (0.3 g, 80% oil dispersion) and 2-amino-3-hydroxypyridine (1.10 g, 10 mmol) was added anhydrous dimethylformamide (15 mL) and the resultant mixture was stirred at ambient temperature for 1 h under argon.

2) To the alkoxide (step 1) was quickly added a solution of 2-(trifluoromethyl)benzyl bromide (2.51 g, 10.5 mmol) in anhydrous dimethylformamide (15 mL) and the resultant mixture was stirred at ambient temperature for 16 h. The reaction mixture was poured into water (200 mL) and extracted with ethyl acetate (3×100 mL). The organic extracts were combined, back-washed with brine (4×50 mL), dried over anhydrous sodium sulfate and concentrated in vacuo to yield 2.64 g of the crude intermediate product (100% yield), which was used in the next step without further purification.

3) A mixture of 2-amino-3-[2-(trifluoromethyl)benzyloxy]pyridine (2.40 g, 8.9 mmol, step 2) and chloroacetone (2.0 mL, 25.0 mmol) in anhydrous methanol (30 mL) was refluxed for 4 days. The methanol was concentrated in vacuo to yield the crude title compound. The residue was partitioned between 2M aq sodium carbonate (150 mL) and dichloromethane (150 mL). The aqueous layer was extracted once more with dichloromethane (150 mL) and the organic extracts were combined, dried over anhydrous sodium sulfate and concentrated in vacuo to yield 2.34 g of the title compound as the free base. The free base was then dissolved in dichloromethane (10–15 mL) and the resultant solution was treated with ethereal hydrogen chloride. The resultant salt crystallized by trituration in diethyl ether and was then recrystallized from a mixture of ethanol-diethyl ether to yield 740 mg of the desired compound. $^1H$-NMR (300 MHz, $CDCl_3$) δ 8.50–6.90 (m, 8H, Ar), 5.45 (s, 2H, $OCH_2$), 2.65 (s, 3H, $CH_3$), 2.40 (br s, 1H, $NH^+$); $^{13}C$-NMR (75 MHz, $CDCl_3$, APT) δ 143.78 (+), 135.07 (+), 132.98 (+), 132.79 (−), 132.63 (+), 128.79 (−), 127.91 (−), 125.41 (−), 120.69 (−), 116.64 (−), 112.76 (−), 109.74 (−), 67.27 (+), 10.68 (−); LR (+LSIMS) m/z: $MH^+$ 307 (100%); Anal. calcd for $C_{16}H_{13}ON_2F_3$.HCl: C, 56.07%, H, 4.12%, N, 8.17%. found: C, 54.62%, H, 4.20%, N, 7.75%.

Example 8

8-[2,4-Dichlorobenzyloxy]-2-Methylimidazo[1,2-α] Pyridine Monohydrochloride

Compound 8

Route A:

1) A 1L two-necked round bottom flask containing molecular sieves (30 g, Type 4 Å) was vacuum flame-dried and cooled to room temperature. The flask was then charged with 2-amino-3-hydroxypyridine (11.2 g, 0.1 mol), chloroacetone (33.5 mL, 0.4 mol) and anhydrous methanol (400 mL) under argon. The resultant mixture was refluxed for 16 h, the molecular sieves were filtered off and the filtrate was concentrated in vacuo. The dark brown residue was dissolved in water (150 mL) and the resultant solution was extracted with diethyl ether (150 mL) and dichloromethane (2×50 mL). The dichloromethane extracts were combined and back-washed with water (20 mL). The aqueous layers were combined and adjusted to pH 10 with 40% aq NaOH, triggering precipitation of a solid. The precipitate was collected, washed successively with water (2×100 mL) and dichloromethane (100 mL), and dried over $P_2O_5$ in vacuo, giving 7.7 g (52% yield) of 8-hydroxy-2-methylimidazo[1,2-α]pyridine as a pale brown powder.

2) A mixture of 8-hydroxy-2-methylimidazo[1,2-α]pyridine (0.9 g, 6 mmol), 2,4-dichlorobenzyl chloride (0.88 mL, 6.3 mmol), tetrabutylammonium bromide (0.38 g, 0.12 mmol), 40% aq NaOH (10 mL), water (20 mL) and dichloromethane (30 mL) was stirred at ambient temperature for 4 days. The two layers of the reaction mixture were separated and the aqueous layer was extracted with dichloromethane (2×30 mL). The organic layers were combined, washed with 1M aq NaOH (30 mL), dried over anhydrous sodium sulfate and concentrated in vacuo to provide the crude title compound as the free base. Purification by dry column (150 mL funnel, silica gel 10–40μ, Sigma cat. S-6628) eluted with a mixture of ethyl acetate-hexanes (1:1.5 v/v, containing 0.5% v/v isopropylamine) provided the free base, which was dissolved in a mixture of diethyl ether-dichloromethane (2:1, v/v, 60 mL). On treatment of the solution with ethereal hydrogen chloride, the title compound was obtained as an off-white powder (1.28 g, 62% yield). $^1H$-NMR (300 MHz, $CD_3OD$) δ 8.35 (d, 1H, Ar), 7.98 (d, 1H, Ar), 7.74 (d, 1H, Ar), 7.58 (d, 1H, Ar), 7.51 (d, 1H, Ar), 7.43 (q, 1H, Ar), 7.36 (q, 1H, Ar), 5.49 (s, 2H, $CH_2$), 4.87 (br s, 1H, $^+NH$), 2.53 (s, 3H, $CH_3$); $^{13}C$-NMR (75 MHz, $CD_3OD$, APT) δ 144.95 (+), 136.68 (+), 136.00 (+), 135.22 (+), 135.02 (+), 132.97 (−), 130.50 (−), 128.77 (−), 122.20 (−), 118.51 (−), 114.50 (−), 112.12 (−), 69.81 (+), 10.35 (−); LRMS-FAB m/z: $MH^+$ 307 (100%); HRMS-FAB (m/z): $[M+H]^+$ calcd for $C_{15}H_{13}ON_2Cl_2$: 307.04049. found: 307.04077; Anal. calcd for $C_{15}H_{12}N_2OCl_2$.HCl: C, 52.43; H, 3.81; N, 8.15%. found: C, 52.29; H, 3.68; N, 8.04%.

Example 9

8-[(3-Cyclohexyl)Propoxy]-2-Methylimidazo[1,2-α] Pyridine Monohydrochloride

Compound 9

Route B:

1) To a cold (0° C.) solution of 3-cyclohexyl-1-propanol (1.72 g, 12 mmol) and triethylamine (1.46 g, 14.4 mmol) in dichloromethane (30 mL) was added dropwise neat methanesulfonyl chloride (1.68 g, 14.4 mmol) under argon. The resultant mixture was stirred at 0° C. for 40 min and then at ambient temperature for 2 h. Saturated aqueous sodium bicarbonate (12 mL) and water (12 mL) were added to the reaction mixture. The layers were separated and the aqueous layer was extracted with dichloromethane (2×24 mL). The organic extracts were combined, dried over anhydrous sodium sulfate and concentrated in vacuo to yield the desired mesylate, which was used in the next step without further purification.

2) To sodium hydride (0.36 g, 80% oil dispersion) and 2-amino-3-hydroxypyridine (1.35 g, 12 mmol) was added anhydrous dimethylformamide (50 mL) and the resultant mixture was stirred at ambient temperature for 1.5 h under argon.

3) To the alkoxide (step 2) was quickly added a solution of the mesylate (step 1) in anhydrous dimethylformamide (22 mL) and the resultant mixture was heated at 75° C. for 4 h. The reaction mixture was cooled to room temperature and then water (20 mL) was added. The mixture was partitioned between brine (300 mL) and ether (300 mL) and the aqueous layer was extracted with ethyl acetate (300 mL). The organic extracts were combined, dried over anhydrous sodium sulfate and concentrated in vacuo to yield the crude desired product. Purification by dry column (350 mL funnel, silica gel 10–40μ, Sigma cat. S-6628) eluted with mixtures ethyl acetate-hexanes (1:6 to 1:2.4 v/v, containing 0.5% v/v isopropylamine) yielded 2.08 g (74% yield) of 2-amino-3-[(3-cyclohexyl)propoxy]pyridine ($R_f$=0.18 in ethyl acetate-hexanes, 1:4 v/v, containing 0.5% v/v isopropylamine).

A mixture of 2-amino-3-[(3-cyclohexyl)propoxy]pyridine (1.93 g, 8.24 mmol, step 3), chloroacetone (3.21 g, 33 mmol) and molecular sieves (6.9 g, type 4Å, 8–12 mesh beads) in anhydrous methanol (80 mL) was refluxed for 91 h. The molecular sieves were filtered off and the filtrate was concentrated in vacuo and diluted with dichloromethane (40 mL). A mixture of saturated aqueous sodium bicarbonate (20 mL) and water (20 mL) was added, and the resultant layers were separated. The aqueous layer was extracted twice more with dichloromethane (2×24 mL). The organic extracts were combined, dried over anhydrous sodium sulfate and concentrated in vacuo to yield the crude desired product. Purification by dry column (150 mL funnel, silica gel 10–40μ, Sigma cat. S-6628) eluted with mixtures of ethyl acetate-hexanes (1:4 to 1:1.7 v/v, containing 0.5% v/v isopropylamine) yielded 0.71 g of the title compound as the free base. The free base was then dissolved in diethyl ether (30 mL) and the resultant solution was treated with ethereal hydrogen chloride. After concentration, the residual oil was dissolved in water and the solution was subjected to lyophilization, affording the hydrochloride salt of the title compound as a yellow solid (0.82 g, 32% yield). $^1$H-NMR (300 MHz, $CDCl_3$) δ 8.46 (d, 1H, Ar), 8.05 (s, 1H, Ar), 7.07 (q, 1H, Ar), 6.89 (d, 1H, Ar), 4.10 (t, 2H, $CH_2O$), 2.59 (s, 3H, $CH_3$), 1.9–0.7 (m, 15H, CH, $CH_2$); $^{13}$C-NMR (75 MHz, $CDCl_3$, APT) δ 144.68 (+),134.39 (+), 133.17 (+), 116.73 (−), 108.71 (−), 70.49(+), 37.06 (+), 33.01(+), 26.37(+), 26.12(+), 25.76(+), 10.57(−); LRMS-EI m/z: 272 (13%).

Example 10

2-Methyl-8-[5-Phenyl-1-Pentoxy]imidazo[1,2-α]Pyridine Monohydrochloride

Compound 10

Route A:

1) To a cold (0° C.) mixture of 5-phenyl-1-pentanol (6 mmol) and triethylamine (7.2 mmol, 1.0 mL) in dichloromethane (40 mL) was added dropwise neat methanesulfonyl chloride (7.2 mmol, 0.57 mL) within 3 min under argon. The mixture was stirred at 0° C. for 30 min and then at room temperature for 1 h. The reaction mixture was diluted with dichloromethane (20 mL) and the resultant solution was washed with water (2×30 mL). The organic layer was dried over anhydrous sodium sulfate and concentrated in vacuo to yield the mesylate (quantitative yield), which was used in the next step without further purification.

2) To 8-hydroxy-2-methylimidazo[1,2-α]pyridine (6 mmol, example 8, step 1) was added sodium hydride (6 mmol, 0.18 g, 80% oil dispersion) and anhydrous dimethylformamide (35 mL) under argon. The resultant suspension was stirred at room temperature for 1 h.

To the alkoxide (step 2) was added quickly the mesylate (step 1) in dimethylformamide (15 mL). The mixture was heated at 75° C. for 3 h and was then allowed to cool to room temperature before being poured into cold water (120 mL). After the aqueous layer was extracted with ethyl acetate (2×100 mL), the organic layers were combined, back-washed with brine (4×130 mL), dried over anhydrous sodium sulfate and concentrated in vacuo. The crude material was purified by column chromatography (silica gel, 10–40μ, Sigma cat. S-6628) eluted with mixtures of ethyl acetate-hexanes (1:2.3–1:1.7 v/v, containing 0.5% v/v isopropylamine). The resultant free base ($R_f$=0.3 in ethyl acetate-hexanes, 2:1 v/v, containing 0.5% v/v isopropylamine) was dissolved in diethyl ether (50 mL) and treated with ethereal hydrogen chloride. Evaporation of the solvent in vacuo yielded the title compound (1.37 g, 69% yield). $^1$H-NMR (300 MHz, $CDCl_3$) δ 8.37 (m, 1H, Ar), 7.96 (s, 1H, Ar), 7.21–6.98 (m, 6H, Ar), 6.85 (d, 1H, Ar), 4.10 (t, 2H, $CH_2O$), 2.58 (s, 3H, $CH_3$), 2.56 (t, 2H, $CH_2Ar$), 1.92 (m, 2H, $CH_2$), 1.56 (m, 4H, $CH_2CH_2$); $^{13}$C-NMR (75 MHz, $CDCl_3$, APT) δ 144.57 (+), 142.30 (+), 134.43 (+), 133.14 (+), 128.18 (−), 128.05 (−), 125.44 (−), 119.77 (−), 116.74 (−), 112.45 (−), 108.67 (−), 69.88 (+), 35.53 (+), 30.84 (+), 28.28 (+), 25.18 (+), 10.57 (−).

Example 11

8-[3-Benzyloxy-1-Propoxy]-2-Methylimidazo[1,2-α] Pyridine Monohydrochloride

Compound 11

Route A:

The title compound was obtained following a procedure similar to the one used in example 10, by using the mesylate of 3-benzyloxy-1propanol. Purification by dry column (150 mL funnel, silica gel 10–40μ, Sigma cat. S-6628) eluted with a mixture of ethyl acetate-hexanes (1:1.8, v/v) provided the free base ($R_f$=0.3 in ethyl acetate-hexanes, 2:1 v/v, containing 0.5% v/v isopropylamine), which was dissolved in diethyl ether (50 mL) and treated with ethereal hydrogen chloride. Evaporation of the solvent in vacuo yielded the title compound (1.55 g, 78% yield). $^1$H-NMR (300 MHz, $CDCl_3$) δ 8.28 (m, 1H, Ar), 7.96 (s, 1H, Ar), 7.24–7.05 (m, 6H, Ar), 6.90 (d, 1H, Ar), 4.45 (s, 2H, $ArCH_2O$), 4.26 (t, 2H, $CH_2O$ Ar), 3.79 (t, 2H, $CH_2O$), 2.58 (s, 3H, $CH_3$), 2.19 (m, 2H, $CH_2$); $^{13}$C-NMR (75 MHz, $CDCl_3$, APT) δ 144.67 (+),138.25 (+), 134.48 (+),133.19 (+), 128.07 (−), 127.61 (−), 127.29 (−), 119.56 (−), 116.94 (−), 112.48 (−), 108.76 (−), 72.82 (+), 66.92 (+), 65.99 (+), 28.98 (+), 10.57 (−).

Example 12

8-[3,3-Diphenyl-1-Propoxy]-2-Methylimidazo[1,2-α] Pyridine Monohydrochloride

Compound 12

Route A:

The title compound was obtained following a procedure similar to the one used in example 10, by using the mesylate of 3,3-diphenyl-1-propanol. Purification by dry column (150 mL funnel, silica gel 10–40μ, U Sigma cat. S-6628) eluted with a mixture of ethyl acetate-hexanes (1:3 v/v, containing 0.5% v/v isopropylamine) provided the free base. Dissolution of the free base in diethyl ether (50 mL) followed by treatment with ethereal hydrogen chloride gave the title compound as a solid (1.28 g, 56% yield). $^1$H-NMR (300 MHz, $CDCl_3$) δ 8.30 (d, 1H, Ar), 7.87 (s, 1H, Ar), 7.33 (s, 2H, Ar), 7.30 (s, 2H, Ar), 7.14 (s, 1H, Ar), 7.11 (s, 2H, Ar), 7.09 (s, 1H, Ar), 7.04 (s, 1H, Ar), 7.01 (s, 1H, Ar), 6.89 (t, 1H, Ar), 6.64 (d, 1H, Ar), 4.77 (t, 1H, CHAr), 4.02 (t, 2H, $CH_2O$), 2.64–2.59 (m, 5H, $CH_2$, $CH_3$); $^{13}$C-NMR (75 MHz, $CDCl_3$, APT) δ 144.49 (+), 143.83 (+), 134.60 (+), 132.99 (+), 128.29 (−), 127.97 (−), 126.08 (−), 119.80 (−), 116.55 (−), 112.38 (−), 108.50 (−), 67.82 (+), 45.93 (−), 34.08 (+), 10.63 (−); LRMS-FAB m/z: $MH^+$ 343 (100%); Anal. calcd for $C_{23}H_{22}N_2O.HCl$: C, 72.91; H, 6.12; N 7.39%. found: C, 72.81; H, 6.21; N, 7.44%.

Example 13

2-Methyl-8-[(1-Phenyl-Cyclopropyl)methoxy]imidazo[1,2-α]Pyridine Monohydrochloride Compound 13

Route A:

The title compound was obtained following a procedure similar to the one used in example 10, by using the mesylate of (1-phenylcyclopropyl)methanol. Purification by dry column (150 mL funnel, silica gel 10–40μ, Sigma cat. S-6628) eluted with a mixture of ethyl acetate-hexanes (1:3 v/v, containing 0.5% v/v isopropylamine) provided the free base. Dissolution of the free base in diethyl ether and treatment with ethereal hydrogen chloride yielded the title compound as a solid (0.52 g, 28% yield). $^1$H-NMR (300 MHz, $CDCl_3$) δ 8.22 (br s, 1H, Ar), 7.83 (br s, 1H, Ar), 7.65 (d, 1H, Ar), 7.31–7.08 (m, 3H, Ar), 6.97 (br s, 1H, Ar), 6.73 (br s, 1H, Ar), 4.25 (s, 2H, $CH_2O$), 2.67 (s, 3H, $CH_3$), 1.20 (s, 2H, $CH_2$), 1.01 (s, 2H, $CH_2$); $^{13}$C-NMR (75 MHz, $CDCl_3$, APT) δ 144.86 (+), 142.27 (+), 135.19 (+), 133.17 (+), 130.25 (−), 128.35 (−), 126.88 (−), 119.87 (−), 116.81 (−), 112.56 (−), 109.41 (−), 78.02 (+), 25.47 (+), 11.47 (+), 10.95 (−); LRMS-FAB m/z: $MH^+$ 279 (100%); Anal. calcd for $C_{18}H_{18}N_2O.HCl$: C, 68.67; H, 6.08; N, 8.90%. found: C, 68.41; H, 6.20; N, 8.95%.

Example 14

8-[3-(2,4-Dichlorophenyl)Propoxy]-2,7-Dimethylimidazo[1,2-α]Pyridine Monohydrochloride Compound 14

Route A:

1) To a cold (0° C.) solution of 3-(2,4-dichloroplienyl)-1-propanol (0.62 g, 3 mmol) and triethylamine (0.51 mL, 3.6 mmol) in dichloromethane (20 mL) was added dropwise neat methanesulfonyl chloride (0.29 mL, 3.6 mmol) under argon. The resultant mixture was stirred at 0° C. for 20 min and then at ambient temperature for 1 h. The reaction mixture was then diluted with dichloromethane (10 mL) and the resultant solution was washed with water (30 mL). The organic layer was dried over anhydrous sodium sulfate and concentrated in vacuo to yield the desired mesylate, which was used in the next step without further purification.

2) To sodium hydride (0.108 g, 80% oil dispersion) and 8-hydroxy-2,7-dimethylimidazo[1,2-α]pyridine (0.487 g, 3 mmol, Kaminski et al., *J. Med. Chem.* 1987, 30, 2031–2046) was added anhydrous dimethylformamide (20 mL) and the resultant mixture was stirred at ambient temperature for 45 min under argon.

3) To the alkoxide (step 2) was quickly added a solution of the mesylate (step 1) in anhydrous dimethylformamide (10 mL) and the resultant mixture was heated at 75° C. for 5 h. After the reaction mixture was allowed to cool to room temperature and then poured into ice water (60 mL), the resultant solution was extracted with ethyl acetate (2×60 mL). The organic extracts were combined, back-washed with brine (4×80 mL), dried over anhydrous sodium sulfate and concentrated in vacuo to yield the crude free base of the title compound as a dark brown oil. After purification by dry column (150 mL funnel, silica gel 10–40μ, Sigma cat. S-6628) eluted with a mixture of ethyl acetate-hexanes (1:3 v/v, containing 0.5% v/v isopropylamine), the free base was dissolved in diethyl ether (40 mL) and the resultant solution was treated with ethereal hydrogen chloride, affording the title compound as a solid (0.71 g, 61% yield). $^1$H-NMR (300 MHz, $CDCl_3$) δ 8.4–8.2 (m, 1H, Ar), 7.85–7.63 (m, 1H, Ar), 7.30–7.20 (m, 2H, Ar), 7.14–7.05 (m, 1H, Ar), 7.01 (s, 1H, Ar), 4.35 (t, 2H, $CH_2O$), 2.94 (t, 2H, $CH_2Ar$), 2.65 (s, 3H, $CH_3$), 2.39 (s, 3H, $CH_3$), 2.30 (m, 2H, $CH_2$); $^{13}$C-NMR (75 MHz, $CDCl_3$, APT) δ 141.72 (+), 137.71 (+), 135.93 (+), 135.12 (+), 134.40 (+), 133.98 (+), 132.20 (+), 131.31 (−), 128.99 (−), 127.08 (−), 122.31 (−), 120.14 (−), 111.80 (−), 74.56 (+), 29.73 (+), 29.32 (+), 15.72 (−), 10.87 (−); LRMS-FAB m/z: $M^+$ 349 (100%); Anal. calcd for $C_{18}H_{18}Cl_2N_2O.HCl$: C, 56.05; H, 4.96; N, 7.26%. found: C, 55.78; H, 5.13; N, 7.07%.

Example 15

8-[3-(2,4-Dichlorophenyl)Propoxy]-2-(Trifluoromethyl)imidazo[1,2-α]Pyridine Monohydrochloride Compound 15

Route B:

1) To a cold (0° C.) solution of 3-(2,4-dicltorophenyl)-1-propanol (4.98 g, 24.3 mmol) and triethylamine (4.1 mL, 29.3 mmol) in dichloromethane (50 mL) was added dropwise neat methanesulfonyl chloride (2.5 mL, 32.2 mmol) under argon. The resultant mixture was stirred at 0° C. for 30 min and then at ambient temperature for 1.5 h. To the reaction mixture was added water (25 mL) and saturated aq sodium bicarbonate (25 mL) and the resultant mixture was extracted with dichloromethane (3×50 mL). The organic extracts were combined, dried over anhydrous sodium sulfate and concentrated in vacuo to yield the desired mesylate, which was used in the next step without further purification.

2) To sodium hydride (0.71 g, 80% oil dispersion) and 2-amino-3-hydroxypyridine (2.61 g, 23.6 mmol) was added anhydrous dimethylformamide (80 mL) and the resultant mixture was stirred at ambient temperature for 30 min under argon.

3) To the alkoxide (step 2) was quickly added a solution of the mesylate (step 1) in anhydrous dimethylformamide (20 mL) and the resultant mixture was heated at 70° C. for 2 h. The cooled reaction mixture was poured into water (75 mL) and brine (250 mL) and extracted with diethyl ether (300 mL). The organic extract was dried over anhydrous sodium sulfate and concentrated in vacuo to yield 5.05 g (96% yield) of 2-amino-3-[3-(2,4-dichlorophenyl)propoxy]pyridine, which was used in the next step without further purification.

A mixture of 2-amino-3-[3-(2,4-dichlorophenyl)propoxy]pyridine (3.27 g, 11 mmol, step 3), 3-bromo-1,1,1-trifluoroacetone (8.4 mL, 44 mmol) and molecular sieves (10.5 g, type 4 Å, beads, 8–12 mesh) in anhydrous methanol (150 mL) was refluxed for 18 h. The molecular sieves were filtered off and the filtrate was concentrated in vacuo to yield the crude title compound. Purification by dry column (600 mL funnel, silica gel 10–40μ, Sigma cat. S-6628) eluted with a mixture of ethyl acetate-hexanes (1:9 v/v, containing 0.5% v/v isopropylamine) yielded 1.5 g of the free amine product. The compound was then dissolved in an anhydrous mixture of diethyl ether and dichloromethane and treated with ethereal hydrogen chloride to give 1.5 g (32% yield) of the title compound as an off-white powder. $^1$H-NMR (300 MHz, $CD_3OD$) δ 8.87 (d, 1H, Ar), 8.42 (d, 1H, Ar), 7.49–7.21 (m, 5H, Ar), 4.39 (t, 2H, $CH_2O$), 3.02 (t, 2H, $CH_2Ar$), 2.27 (qt, 2H, $CH_2$); $^{13}$C-NMR (75 MHz, $CD_3OD$, APT) δ 146.6 (+), 138.9 (+), 137.8 (+), 135.7 (+), 133.7 (+), 132.9 (−), 130.1 (−), 128.4 (−), 127.0 (+), 127.6 (+), 122.5 (−), 119.7 (−), 119.0 (+), 122.1 (+), 123.0 (+), 118.0 (−), 113.2 (−), 70.5 (+), 30.1 (+); LRMS-ES m/z: 389.2.

Example 16

Ethyl 8-[3-(2,4-Dichlorophenyl)Propoxy]-2-Methylimidazo[1,2-α]Pyridine-3-Carboxylate Monohydrochloride Compound 16

Route B:

A stirred mixture of 2-amino-3-[3-(2,4-dichlorophenyl)propoxy]pyridine (1.20 g, 4.04 mmol, example 15), ethyl 2-chloroacetoacetate (2.66 g, 16.1 mmol) and molecular sieves (4.0 g, type 4 Å, beads, 8–12 mesh) in anhydrous methanol (10 mL) was refluxed for 20 h under argon. The molecular sieves were filtered off and the filtrate was concentrated in vacuo to yield the crude material. Purification by dry column (300 mL funnel filled with 450 mL of silica gel 10–40μ, Sigma cat. S-6628) eluted with mixtures of ethyl acetate-hexanes (v/v: 1:8, 1:4, containing 0.5% v/v isopropylamine) yielded 0.540 g (33% yield) of the title compound as the free base ($R_f$=0.50 in ethyl acetate-hexanes, 1:4 v/v, containing 0.5% v/v isopropylamine). The free base (0.35 g) was dissolved in dichloromethane (10 mL) and treated with ethereal hydrogen chloride to form the corresponding hydrochloride salt. $^1$H-NMR (300 MHz, $CDCl_3$) δ 8.90 (d, 1H, Ar), 7.30 (s, 1H, Ar), 7.10 (m, 2 H, Ar), 6.80 (t, 1H, Ar), 6.60 (d, 1H, Ar), 4.40 (q, 2H, $OCH_2CH_3$), 4.10 (t, 2H, $OCH_2$), 2.90 (t, 2H, $CH_2$), 2.70 (s, 3H, $CH_3$), 2.20 (qt, 2H, $CH_2$), 1.40 (t, 3H, $CH_2CH_3$); $^{13}$C-NMR (75 MHz, $CDCl_3$, APT) δ 161.43 (+), 151.65 (+), 147.29 (+), 137.27 (+), 134.59 (+), 132.43 (+), 131.26 (+), 129.24 (−), 127.04 (−), 120.65 (−), 113.59 (+), 113.30 (−), 105.10 (−), 67.82 (+), 60.23 (+), 29.33 (+), 28.34 (+), 16.66 (−), 14.39 (−); LRMS-ES m/z: 407.1.

Example 17

2,7-Dimethyl-8-[(1-Phenyl-Cyclopropyl)methoxy]imidazo[1,2-α]Pyridine Monohydrochloride Compound 17

Route A:

To a cold (0° C.) solution of (1-phenyl-cyclopropyl)methanol (0.565 g, 3.81 mmol) and triethylamine (0.64 mL, 4.57 mmol) in dichloromethane (30 mL) was added dropwise neat methanesulfonyl chloride (0.36 mL, 4.57 mmol) under argon. The resultant mixture was stirred at 0° C. for 50 min and then at ambient temperature for 1 h. The reaction mixture was then diluted with dichloromethane (15 mL) and washed successively with saturated aq sodium bicarbonate (2×30 mL) and water (30 mL). The organic layer was dried over anhydrous sodium sulfate and concentrated in vacuo to yield the desired mesylate, which was used in the next step without further purification.

To sodium hydride (0.11 g, 80% oil dispersion) and 2,7-dimethyl-8-hydroxyimidazo[1,2-α]pyridine (0.552 g, 3.6 mmol, see example 14) was added anhydrous dimethylformamide (20 mL) and the resultant mixture was stirred at ambient temperature for 10 min under argon.

To the alkoxide (step 2) was quickly added a solution of the mesylate (step 1) in anhydrous dimethylformamide (10 mL) and the resultant mixture was heated at 60° C. for 16 h. After the reaction was allowed to cool to room temperature, it was poured into ice water (60 mL) and the resultant mixture was extracted with ethyl acetate (2×60 mL). The organic extracts were combined, back-washed with brine (4×80 mL), dried over anhydrous sodium sulfate and concentrated in vacuo to yield the crude free base of the title compound. Purification by dry column (150 mL funnel, silica gel 10–40μ, Sigma cat. S-6628) eluted with mixtures of ethyl acetate-hexanes (1:5.5–1:3 v/v, containing 0.5% v/v isopropylarnine) provided the free base ($R_f$=0.5, ethyl acetate-hexanes, 2:1 v/v, containing 0.5% v/v isopropylamine), which was dissolved in diethyl ether (20 mL) and treated with ethereal hydrogen chloride. The title compound was obtained as an off-white solid (0.17 g, 15% yield). $^1$H-NMR (300 MHz, $CDCl_3$) δ 15.25 (br s, 1H, $^+$NH), 8.41 (br s, 1H, Ar), 7.88 (br s, 1H, Ar), 7.37 (s, 1H, Ar), 7.35 (s, 1H, Ar), 7.25–7.08 (m, 3H, Ar), 6.86 (br s, 1H, Ar), 4.49 (s, 2H, $CH_2O$), 2.61 (s, 3H, $CH_3$), 1.76 (s, 3H, $CH_3$), 1.36 (s, 2H, $CH_2$), 0.89 (s, 2H, $CH_2$); $^{13}$C-NMR (75 MHz, $CDCl_3$, APT) δ 142.87 (+), 141.24 (+), 135.59 (+), 134.48 (+), 134.39 (+), 129.43 (−), 128.03 (−), 126.55 (−), 122.52 (−), 120.00 (−), 112.10 (−), 82.62 (+), 26.40 (+), 14.96 (−), 11.52 (+), 10.75 (−); LRMS-FAB m/z: $MH^+$ 293 (100%); Anal. calcd for $C_{19}H_{20}N_2O.HCl$: C, 69.40; H, 6.44; N, 8.52%. found: C, 68.77; H, 6.41; N, 8.33%.

Example 18

2,7-Dimethyl-8-[3-Phenylproprxy]imidazo[1,2-α]Pyridine Monohydrochloride

Compound 18

Route A:

To sodium hydride (0.11 g, 80% oil dispersion) and 2,7-dimethyl-8-hydroxy-imidazo[1,2-α]pyridine (0.552 g, 3.6 mmol, see example 14) was added anhydrous dimethylformamide (30 mL) and the resultant mixture was stirred at ambient temperature for 10 min under argon. Then 1-bromo-3-phenylpropane (0.58 mL, 3.81 mmol) was added and the resultant mixture was heated at 60° C. for 4 h. After the reaction mixture was allowed to cool to room temperature, it was poured into ice water (60 mL) and extracted with ethyl acetate (2×60 mL). The organic extracts were combined, back-washed with brine (4×80 mL), dried over anhydrous sodium sulfate and concentrated in vacuo to yield the crude free base of the title compound. Purification by dry column (150 mL funnel, silica gel 10–40μ, Sigma cat. S-6628) eluted with a mixture of ethyl acetate-hexanes (1:3 v/v, containing 0.5% v/v isopropylamine) provided the free base ($R_f$=0.43, ethyl acetate-hexanes, 2:1 v/v, containing 0.5% v/v isopropylamine), which was dissolved in diethyl ether (30 mL) and treated with ethereal hydrogen chloride. Evaporation of the solvent in vacuo afforded a residual oil, which was triturated in diethyl ether (150 mL) to yield the title compound as a solid (0.75 g, 70% yield). $^1$H-NMR (300 MHz, $CDCl_3$) δ 15.38 (br s, 1H, $^+$NH), 8.52 (s, 1H, Ar), 7.94 (s, 1H, Ar), 7.18–7.03 (m, 5H, Ar), 6.95 (d, 1H, Ar), 4.25 (t, 2H, $CH_2O$), 2.79 (t, 2H, $CH_2Ar$), 2.58 (s, 3H, $CH_3$), 2.35–2.23 (m, 5H, $CH_3$, $CH_2$); $^{13}$C-NMR (75 MHz, $CDCl_3$, APT) δ 141.33 (+), 141.23 (+), 135.79 (+), 134.39 (+), 133.96 (+), 128.18 (−), 125.74 (−), 122.93 (−), 119.87 (−), 112.20 (−), 74.43 (+), 31.79 (+), 31.28 (+), 15.51 (−), 10.65 (−); LRMS-FAB m/z: $MH^+$ 281 (100%); Anal. calcd for $C_{18}H_{20}N_2O$.HCl: C, 68.24; H, 6.68; N, 8.84%. found: C, 67.92; H, 6.75; N, 8.77%.

Example 19

3-Bromo-8-[3-(2,4-Dichlorophenyl)Propoxy]-2-Methylimidazo[1,2-α]Pyridine Monohydrochloride

Compound 19

A solution of 8-[3-(2,4-dichlorophenyl)propoxy]-2-methylimidazo[1,2-α]pyridine (1.07 g, 3 mmol, see example 1) and N-bromosuccinmide (0.592 g, 3.3 mmol) in ethanol (13 mL) was stirred at room temperature for 1 h. The solvent was evaporated in vacuo and water (20 mL) was added to the residue. After extraction with dichloromethane (3×20 mL), the organic extracts were combined, back-washed with brine (50 mL) and dried over anhydrous sodium sulfate. Concentration in vacuo and purification of the crude product by dry column (60 mL funnel, silica gel 10–40μ, Sigma cat. S-6628) eluted with a mixture of ethyl acetate-hexanes (1:3 v/v, containing 0.5% v/v isopropylamine) provided the free amine of the title compound. The free amine was dissolved in anhydrous diethyl ether and treated with ethereal hydrogen chloride to give 0.797 g (59% yield) of the title compound as an off-white powder. $^1$H-NMR (300 MHz, $CDCl_3$) δ 7.64 (d, 1H, Ar), 7.33 (d, 1H, Ar), 7.17–7.09 (m, 2H, Ar), 6.70 (t, 1H, Ar), 6.42 (d, 1H, Ar), 4.12 (t, 2H, $CH_2O$), 2.93 (t, 2H, $CH_2Ar$), 2.44 (s, 3H, $CH_3$), 2.23 (qt, 2H, $CH_2$); $^{13}$C-NMR (75 MHz, $CDCl_3$, APT) δ 147.6 (+), 141.0 (+), 139.4 (+), 137.3 (+), 134.6 (+), 132.4 (+), 131.3 (−), 129.2 (−), 127.0 (−), 116.6 (−), 112.3 (−), 101.7 (−), 93.8 (+), 67.7 (+), 29.3 (+), 28.3 (+), 13.5 (−);LRMS-EI m/z: 414 (53).

Example 20

8-[3-(2,4-Dichlorophenyl)Propoxy]-2-Isopropylimidazo[1,2-α]Pyridine Monohydrochloride

Compound 20

Route B:

A stirred mixture of 2-amino-3-[3-(2,4-dichlorophenyl) propoxy]pyridine (600 mg, 2.02 mmol, see example 1), 1-bromo-3-methyl-2-butanone (1.33 g, 8.06 mmol, M. Gaudry and A. Marquet, Organic Syntheses, Vol. 55, p. 24) and molecular sieves (2.0 g, type 4 Å, beads, 8–12 mesh) in anhydrous methanol (10 mL) was refluxed for 20 h under argon. The molecular sieves were filtered off and the filtrate was concentrated in vacuo to yield the crude title compound. The material was taken up in hexanes (50 mL) and upon standing a pale yellow solid formed. Decantation of the hexanes and dissolution of the residue in dichloromethane (15 mL) gave a solid, which was collected, dissolved in methanol (10 mL) and treated with ethereal hydrogen chloride. Concentration of the solution in vacuo and trituration of the residue in diethyl ether yielded 370 mg of the title compound. $^1$H-NMR (300 MHz, $CD_3OD$) δ 8.30 (d, 1H, Ar), 8.00 (s, 1H, Ar), 7.40–7.20 (m, 5 H, Ar), 4.40 (t, 2H, $CH_2O$), 3.25 (m, 1H, CH), 3.00 (t, $CH_2$), 2.30 (qt, 2H, $CH_2$), 1.4 (d, 6H, $CH_3$); $^{13}$C-NMR (75 MHz, $CD_3OD$, APT) δ 145.49 (+), 145.22 (+), 138.90 (+), 135.69 (+), 135.36 (+), 133.68 (+), 132.92 (−), 130.06 (−), 128.42 (−), 121.79 (−), 118.65 (−), 112.64 (−), 111.80 (−), 70.36 (+), 30.09 (+), 29.54 (+), 27.07 (−), 21.93 (−); LRMS-ES m/z: $M^+$ 363.1.

Example 21

{8-[3-(2,4-Dichlorophenyl)Propoxy]-2-Methylimidazo[1,2-α]pyridin-3-yl}Methanol Mmonohydrochloride

Compound 21

To a cold (−10° C.) suspension of lithium aluminum hydride (93 mg, 2.46 mmol) in anhydrous tetrahydrofuran (10 mL) was added portionwise a solution of ethyl 8-[3-(2,4-dichlorophenyl)propoxy]-2-methylimidazo[1,2-α]pyridine-3-carboxylate (500 mg, 1.23 mmol, see example 16) in anhydrous tetrahydrofuran (10 mL). The resultant mixture was stirred at −5° C. for 1 h and then saturated aq sodium sulfate (2 mL) was added slowly. The solution was then allowed to warm to room temperature at which it was stirred for 2 h. Filtration of the reaction mixture and concentration of the filtrate in vacuo yielded 410 mg of the title compound as a free base. The free base was dissolved in a mixture of dichloromethane-methanol (1:1, v/v) and converted to the hydrochloride salt by addition of ethereal hydrogen chloride to yield, after evaporation of the solvents and trituration in diethyl ether, 230 mg of the title compound. $^1$H-NMR (300 MHz, $CDCl_3$) δ 15.00 (br s, 1H, $NH^+$), 8.40 (d, 1H, Ar), 7.40–6.80 (m, 5H, Ar), 4.80 (s, 2H, $CH_2OH$), 4.10 (m, 2H, $CH_2O$), 3.00 (m, 2H, $CH_2$), 2.60 (s, 3H, $CH_3$), 2.10 (m, 2H, $CH_2$); $^{13}$C-NMR (75 MHz, $CDCl_3$) δ 143.98 (+), 137.31 (+), 134.24 (+), 132.12 (+), 132.09 (+), 132.01 (−), 131.42 (+), 129.92 (−), 128.71 (−), 128.11 (−), 126.94 (−), 68.79 (+), 51.28 (+), 29.07 (+), 28.30 (+), 9.80 (−); LRMS-ES m/z $M^+$ 365.2.

Example 22

3-Chloro-8-[3-(2,4-Dichlorophenyl)Propoxy]-2-Methyli[1,2-α]Pyridine Mmonohydrochloride

Compound 22

A solution of 8-[3-(2,4-dichlorophenyl)propoxy]-2-methylimidazo[1,2-α]pyridine (1.42 g, 4 mmol, see example 1) and N-chlorosuccinimide (0.816 g, 6 mmol) in ethanol (18 mL) was stirred at room temperature for 1 h. The organic solvent was evaporated in vacuo and to the residue was added water (20 mL). The reaction mixture was extracted with dichloromethane (3×20 mL), the organic extracts were combined, back-washed with brine (50 mL) and dried over anhydrous sodium sulfate. Removal of the solvent in vacuo and purification of the residue by dry column (60 mL funnel, silica gel 10–40μ, Sigma cat. S-6628) eluted with a mixture of ethyl acetate-hexanes (1:3 v/v, containing 0.5% v/v isopropylamine) provided the free amine of the title compound. The free base was then dissolved in anhydrous diethyl ether and treated with ethereal hydrogen chloride to give 0.397 g (24.4% yield) of the title compound as an off-white powder. $^1$H-NMR (300 MHz, $CDCl_3$) δ 7.61 (d, 1H, Ar), 7.33 (d, 1,H, Ar), 7.18–7.09 (m, 2H, Ar), 6.72 (t, 1H, Ar), 6.41 (d, 1H, Ar), 4.12 (t, 2H, $CH_2O$), 2.93 (t, 2H, $CH_2Ar$), 2.43 (s, 3H, $CH_3$), 2.24 (qt, 2H, $CH_2$); $^{13}$C-NMR (75 MHz, $CDCl_3$, APT) δ 147.6(+), 137.9 (+), 137.6 (+), 137.3 (+), 134.6 (+), 132.4 (+), 131.3 (–), 129.2 (–), 127.0 (–), 115.4 (–), 112.2 (–), 107.4 (+), 101.47 (–), 67.7 (+), 29.4 (+), 28.4 (+), 12.8 (–); LRMS-EI m/z $M^+$ 368 (89).

Example 23

8-[(1-Phenylcyclopropyl)Methoxy]-2-(Trifluoromethyl)imidazo[1,2-α]Pyridine Mmonohydrochloride

Compound 23

Route B:

1) To a cold (0° C.) solution of (1-phenylcyclopropyl) methanol (0.89 g, 6.0 mmol) and triethylamine (1.00 mL, 7.2 mmol) in dichloromethane (20 mL) was added dropwise neat methanesulfonyl chloride (0.56 mL, 7.2 mmol) under argon. The resultant mixture was stirred at 0° C. for 30 min and then at ambient temperature for 4.5 h. The reaction mixture was diluted with dichloromethane (30 mL) and washed with water (3×20 mL). The organic layer was dried over anhydrous magnesium sulfate and concentrated in vacuo to yield the desired mesylate, which was used immediately in the next step without further purification.

2) To a stirred solution of 2-amino-3-hydroxypyridine (0.66 g, 6.0 mmol) in anhydrous dimethylformamide (20 mL) was added sodium hydride (0.18 g, 6.0 mmol, 80% oil dispersion). The resultant mixture was stirred at ambient temperature for 1 h under argon.

3) To the alkoxide (step 2) was quickly added a solution of the mesylate (step 1) in anhydrous dimethylformamide (15 mL) and the resultant mixture was stirred at ambient temperature for 16 h under argon and then heated at 50° C. for 5.5 h. After the reaction mixture was allowed to cool to room temperature, it was poured into water (100 mL) and extracted with ethyl acetate (4×50 mL). The organic extracts were combined, washed with brine (4×50 mL), dried over anhydrous magnesium sulfate and concentrated in vacuo to yield the crude desired product. Purification by dry column (600 mL funnel filled with 450 mL silica gel 10–40μ, Sigma cat. S-6628) eluted with a mixture of ethyl acetate-hexanes (2:1 v/v, containing 0.5% v/v isopropylamine) yielded 0.80 g (55% yield) of 2-amino-3-[(1-phenylcyclopropyl)methoxy]pyridine ($R_f$=0.22 in ethyl acetate-hexanes, 1:1 v/v, containing 0.5% v/v isopropylamine).

A stirred mixture of 2-amino-3-[(1-phenylcyclopropyl) methoxy]pyridine (0.731 g, 3.04 mmol, step 3), 3-bromo-1,1,1-trifluoroacetone (1.3 mL, 13 mmol) and molecular sieves (4.0 g, type 4 Å, beads, 8–12 mesh) in anhydrous methanol (15 mL) was refluxed for 22.5 h under argon. The molecular sieves were filtered off and the filtrate was concentrated in vacuo to yield a brown oil which was dissolved in dichloromethane (100 mL) and washed with a 1:1 (v/v) mixture of saturated aq sodium bicarbonate and water (2×10 mL). The organic layer was dried over anhydrous magnesium sulfate and concentrated in vacuo to yield the crude desired product. Purification by dry column (600 mL funnel filled with 300 mL of silica gel 10–40μ, Sigma cat. S-6628) eluted with a mixture of ethyl acetate-hexanes (1:3 v/v, containing 0.5% v/v isopropylamine) yielded 1.00 g (99% yield) of 8-[(1-phenylcyclopropyl)methoxy]-2-(trifluoromethyl)imidazo[1,2-α]pyridine ($R_f$=0.33 in ethyl acetate-hexanes, 1:3 v/v, containing 0.5% v/v isopropylamine). A stirred solution of the free amine (0.950 g, 2.86 mmol) in dichloromethane (4 mL) and anhydrous diethyl ether (16 mL) was treated with ethereal hydrogen chloride to form the hydrochloride salt. After 20 min, the solvent was removed in vacuo, and the residue was triturated in anhydrous diethyl ether to give the title compound as a pale yellow solid (0.414 g, 39% yield). $^1$H-NMR (300 MHz, $CDCl_3$) δ 8.58 (d, 1H, Ar), 8.55 (s, 1H, Ar), 7.50 (m, 1H, Ar), 7.06 (m, 2H, Ar), 6.91 (m, 2H, Ar), 6.78 (m, 1H, Ar), 6.72 (d, 1H, Ar), 4.11 (s, 2H, $CH_2O$), 0.69 (m, 4H, $CH_2CH_2$); $^{13}$C-NMR (75 MHz, $CDCl_3$, APT) δ 146.50 (+), 141.44 (+), 137.01 (+), 129.76/129.21 (+), 127.90 (–), 125.98 (–), 121.69/118.12 (+), 120.97 (–), 116.31 (–), 114.85 (–), 107.82 (–), 76.35 (+), 23.03 (+), 13.75 (+); LRMS-FAB m/z: $MH^+$ 333 (100%); Anal. calcd for $C_{18}H_{15}N_2OF_3$.HCl: C, 58.63; H, 4.37; N, 7.60%. found: C, 56.80; H, 4.07; N, 7.03%.

Examples 24 & 25

8-[3-(2,4-Dichlorophenyl)Propoxy]-3-[(Methylamino)Methyl]-2-Methyl-imidazo[1,2-α]pyridine Dihydrochloride and 8-[3-(2,4-Dichlorophenyl)Propoxy]-3-[(Dimethylamino)methyl]-2-Methylimidazo[1,2-α]pyridine Dihydrochloride

Compounds 24 & 25

A mixture of 8-[3-(2,4-dichlorophenyl)propoxy]-2-methylimidazo[1,2-α]pyridine (703 mg, 2 mmol, see example 1), dimethylamine hydrochloride (700 mg, 8.48 mmol) and paraformaldehyde (256 mg, 8.48 mmol) in methanol (5 mL) was refluxed for 40 h. The reaction mixture was concentrated in vacuo and the residue was partitioned between dichloromethane (15 mL) and saturated aq sodium bicarbonate solution (5 mL) and water (5 mL). The layers were separated and the aqueous layer was extracted with dichloromethane (2×10 mL). The organic extracts were combined, dried over anhydrous sodium sulfate and concentrated in vacuo. Purification by dry column (60 mL funnel, silica gel 10–40μl, Sigma cat. S-6628) eluted with increasingly polar mixtures of ethyl acetate-hexanes (v/v: 1:1.4, 1.2:1, 2:1, 2.9:1, 5:1, containing 0.5% v/v isopropylamine) yielded 406 mg (52% yield) of 8-[3-(2,4-dichlorophenyl)propoxy]-3-[(methylamino)methyl]-2-methylimidazo[1,2-α]pyridine in the first fraction ($R_f$=0.20 in ethyl acetate-hexanes, 2:1 v/v, containing 0.5% v/v isopropylamine) and 221 mg (27% yield) of 8-[3-(2,4-dichlorophenyl)propoxy]-3-[(dimethylamino)methyl]-2-methylimidazo[1,2-α]pyridine in the second fraction ($R_f$=0.07 in ethyl acetate-hexanes, 2:1 v/v, containing 0.5% v/v isopropylamine).

Compound 24. 8-[3-(2,4-Dichlorophenyl)propoxy]-3-[(methylamino)methyl]-2-methylimidazo[1,2-α]pyridine (406 mg) was dissolved in a mixture of diethyl ether and dichloromethane and treated with ethereal hydrogen chloride. The solvent was evaporated in vacuo to yield 481 mg of the title compound 24 as a white solid. $^1$H-NMR (300 MHz, $CDCl_3$) δ 7.70 (d, 1H, Ar), 7.32 (d, 1H, Ar), 7.14 (m, 2H, Ar), 6.63 (t, 1H, Ar), 6.41 (d, 1H, Ar), 4.67 (s, 2H, $CH_2NH$), 4.11 (t, 2H, $CH_2O$), 3.26 (s, 3H, $CH_3NH$), 2.92 (t, 2H, $CH_2Ph$), 2.46 (s, 3H, $CH_3$), 2.22 (qt, 2H, $CH_2CH_2O$); $^{13}C$-NMR (75 MHz, $CDCl_3$, APT) δ 147.66 (+), 141.91 (+), 139.34 (+), 137,42 (+), 134.59 (+), 132.35 (+), 131.29 (−), 129.20 (−), 127.00 (−), 117.26 (+), 116.96 (−), 111.67 (−), 101.84 (−), 67.49 (+), 62.84 (+), 56.99 (−), 29.38 (+), 28.37 (+), 13.31 (−); LRMS-EI m/z: $M^+$ 378 (10%).

Compound 25. 8-[3-(2,4-Dichlorophenyl)propoxy]-3-[(dimethylamino)methyl]-2-methylimidazo[1,2-α]pyridine (221 mg) was dissolved in a mixture of ether-dichloromethane and treated with ethereal hydrogen chloride. The solvent was evaporated in vacuo to yield 260 mg of the title compound 25. $^1H$-NMR (300 MHz, $CDCl_3$) δ 7.77 (q, 1H, Ar), 7.32 (d, 1H, Ar), 7.16 (m, 2H, Ar), 6.60 (t, 1H, Ar), 6.38 (d, 1H, Ar), 4.11 (t, 2H, $CH_2O$), 3.58 (s, 2H, $CH_2N$), 2.93 (t, 2H, $CH_2$), 2.42 (s, 3H, $CH_3$), 2.25 (qt, 2H, $CH_2CH_2O$), 2.18 (s, 6H, $(CH_3)_2N$); $^{13}C$-NMR (75 MHz, $CDCl_3$, APT) δ 147.51 (+), 140.83 (+), 138.84 (+), 137.46 (+), 134.58 (+), 132.31 (+), 131.27 (−), 129.18 (−), 126.98 (−), 117.91 (+), 117.42 (−), 111.18 (−), 101.20 (−), 67.41 (+), 52.52 (+), 44.94 (−), 29.40 (+), 28.41 (+), 13.31 (−); LRMS-EI m/z: $MH^+$ 391(16%).

Example 26

3-Amino-8-[3-(2,4-Dichlorophenyl)Propoxy]-2-Methylimidazo[1,2-α]Pyridine Dihydrochloride

Compound 26

1) A mixture of 8-[3-(2,4-dichlorophenyl)propoxy]-2-methylimidazo[1,2-α]-pyridine (335 mg, 1 mmol, see example 1) and n-butyl nitrite (432 mg, 95%, 4 mmol) in anhydrous tetrahydrofuran (5 mL) was refluxed for 1.5 h. The reaction mixture was concentrated in vacuo to yield the desired nitroso intermediate, which was used in the next step without further purification.

2) To a cold (0° C.) mixture of the crude nitroso intermediate (step 1) in glacial acetic acid (5.5 mL) and water (2.75 mL) was added slowly powdered zinc (327 mg, 5 mmol). The resultant mixture was stirred at 0° C. for 75 min. The reaction mixture was concentrated in vacuo and the residue was partitioned between water (100 mL) and ether (100 mL). To adjust the aqueous layer to pH 12, 40% aq NaOH was added. The aqueous layer was extracted with diethyl ether (2×100 mL). The organic extracts were combined, dried over anhydrous sodium sulfate and concentrated in vacuo. Purification by dry column (60 mL funnel, silica gel 10–40μ, Sigma cat. S-6628) eluted with increasingly polar mixtures of ethyl acetate-hexanes (v/v: 1:3, 2:1, 2.9:1, 5:1, containing 0.5% v/v isopropylamine) yielded 232 mg of 3-amino-8-[3-(2,4-dichlorophenyl)propoxy]-2-methylimidazo[1,2-α]pyridine as free amine ($R_f$=0.16 in ethyl acetate containing 0.5% v/v isopropylamine). The purified product was dissolved in a mixture of diethyl ether and dichloromethane and the resultant solution was treated with ethereal hydrogen chloride. The solvents were evaporated in vacuo to yield 244 mg (58% yield, 2 steps) of the title compound. $^1H$-NMR (free amine, 300 MHz, $CDCl_3$) δ 7.58 (q, 1H, Ar), 7.32 (d, 1H, Ar), 7.12 (m, 2H, Ar), 6.59 (t, 1H, Ar), 6.29 (d, 1H, Ar), 4.09 (t, 2H, $CH_2O$), 2.96 (s, br, 2H, NH2), 2.91 (t, 2H, $CH_2$), 2.37 (s, 3H, $CH_3$), 2.21 (m, 2H, $CH_2CH_2O$); $^{13}C$-NMR (free amine, 75 MHz, $CDCl_3$, APT) δ 147.52 (+), 137.45 (+), 134.80 (+), 134.57 (+), 132.28 (+), 131.55 (+), 131.29 (−), 129.16 (−), 126.98 (−), 122.90 (+), 114.90 (−), 110.89 (−), 99.93 (−), 67.33 (+), 29.38 (+), 28.38 (+), 12.63 (−); LRMS-EI m/z: $M^+$ 349 (32).

Example 27

4-[3-(2,4-Dichlorophenyl)Propoxy]-6,7,8,9-tetrahydrobenzo[4,5]imidazo-[1,2-α]Pyrdine Mmonohydrochloride

Compound 27

Route B:

A stirred mixture of 2-amino-3-[3-(2,4-dichlorophenyl)propoxy]pyridine (500 mg, 1.68 mmol, see example 1), 2-chlorocyclohexanone (884 mg, 6.72 mmol), tetramethylammonium iodide (1.0 g, 5 mmol) and molecular sieves (2.0 g, type 4 Å, beads, 8–12 mesh) in anhydrous methanol (20 mL) was refluxed for 20 h under argon. The molecular sieves were filtered off and the filtrate was concentrated in vacuo. Purification by chromatography using as eluent mixtures of ethyl acetate-hexanes (1:8, 1:4, v/v, containing 5% v/v triethylamine) yielded 0.150 g of the title compound as a free base. The free base (0.150 g) was dissolved in ethyl acetate (10 mL) and treated with ethereal hydrogen chloride to form the hydrochloride salt. The solvents were evaporated in vacuo and to the residue was added ethyl acetate (3 mL) and methanol (1 mL). When the resultant solution was brought to reflux, more ethyl acetate (4 mL) was added, followed by slow addition of hexanes (8 mL). The solution, which became cloudy, was slowly cooled and the title compound was isolated as a solid (90 mg). $^1H$-NMR (300 MHz, $CD_3OD$) δ 8.15 (d, 1H, Ar), 7.50–7.20 (m, 5 H, Ar), 4.40 (t, 2H, $CH_2O$), 3.05 (t, 2H, $CH_2$), 2.90 (m, 4H, 2×$CH_2$), 2.25 (t, 2H, $CH_2$), 2.00 (m, 4H, 2×$CH_2$); $^{13}C$-NMR (75 MHz, $CD_3OD$, APT) δ 145.50 (+), 138.90 (+), 135.71 (+), 133.69 (+), 133.19 (+), 132.89 (−), 130.10 (−), 128.41 (−), 124.33 (+), 118.91 (−), 118.37 (−), 111.10 (−), 70.17 (+), 30.17 (+), 29.58 (+), 22.92 (+), 22.60 (+), 21.97 (+), 20.30 (+); LRMS-ES m/z: $M^+$ 375.0; Anal. calcd for $C_{20}H_{20}N_2OCl_2$.HCl: C, 58.34; H, 5.14; N, 6.80%. found: C, 57.36; H, 5.03; N, 6.38%.

Example 28

3-Bromo-2-methyl-8-[(1-Phenyl-Cyclopropyl)methoxy]imidazo[1,2-α]Pyridine Mmonohydrochloride

Compound 28

A solution of 2-methyl-8-[(1-phenyl-cyclopropyl)methoxy]imidazo[1,2-α]pyridine (0.556 g, 2 mmol, see example 13) and N-bromosuccinimide (0.400 g, 2.2 mmol) in ethanol (13 mL) was stirred at room temperature for 1 h. The organic solvent was evaporated in vacuo and to the residue was added water (20 mL). After extraction of the resultant mixture with dichloromethane (3×20 mL), the organic extracts were combined, back-washed with brine (50 mL) and dried over anhydrous sodium sulfate. The solvent was removed in vacuo and the crude product was purified by dry column (60 mL funnel, silica gel 10–40μ, Sigma cat. S-6628) eluted with a mixture of ethyl acetate-hexanes (1:9 v/v, containing 0.5% v/v isopropylamine) to provide the free amine of the title compound. The free base was then dissolved in anhydrous diethyl ether and treated with ethereal hydrogen chloride to yield 0.308 g (53.0% yield) of the title compound. $^1H$-NMR (300 MHz, $CDCl_3$) δ 7.63 (t, 1H, Ar), 7.44 (m, 2H, Ar), 7.28–7.14 (m, 3H, Ar), 6.64 (t, 1H, Ar), 6.35 (d, 1H, Ar), 4.31 (s, 2H, $CH_2O$), 2.44 (s, 3H, $CH_3$), 1.06 (m, 4H, $CH_2$); $^{13}C$-NMR (75 MHz, $CDCl_3$, APT) δ 147.9 (+), 142.8 (+), 140.9 (+), 139.5 (+), 128.8 (−), 128.3

(−), 126.5 (−), 116.7 (−), 112.2 (−), 103.0 (−), 93.7 (+), 76.6 (+),25.1 (+), 13.6 (−), 12.2 (+); LRMS-EI m/z: $M^+$ 356, 358 (53).

Example 29

7-[3-(2,4-Dichlorophenyl)Propoxy]-2,3-dihydro-1H-3b,8-diazocyclopenta[a]indene Mmonohydrochloride

Compound 29

Route B:

A stirred mixture of 2-amino-3-[3-(2,4-dichlorophenyl) propoxy]pyridine (509 mg, 1.70 mmol, see example 1), 2-chlorocyclopentanone (242 mg, 2.0 mmol), sodium carbonate (180 mg, 1.70 mmol) and molecular sieves (2.0 g, type 4 Å, beads, 8–12 mesh) in anhydrous methanol (10 mL) was refluxed for 20 h under argon. The molecular sieves were filtered off and the filtrate was concentrated in vacuo. Purification by chromatography eluted with mixtures of ethyl acetate-hexanes (1:8 v/v, containing 5% v/v triethylamine) yielded 40 mg of the title compound as a free base. The free base was then dissolved in dichloromethane (10 mL) and treated with ethereal hydrogen chloride to give the title compound as a solid (37 mg). $^1$H-NMR (300 MHz, $CDCl_3$) δ 7.45 (d, 1H, Ar), 7.30 (s, 1H, Ar), 7.20–7.05 (m, 2H, Ar), 6.60 (t, 2H, Ar), 6.35 (t, 1H, Ar), 4.10 (t, 2H, $CH_2O$), 3.00–2.80 (2×m, 6H, 3×$CH_2$), 2.60 (m, 2H, $CH_2$), 2.20 (m, 2H, $CH_2$); $^{13}$C-NMR (75 MHz, $CDCl_3$, APT) δ 151.91 (+), 148.01 (+), 143.58 (+), 137.47 (+), 134.60 (+), 132.28 (+), 131.41 (−), 129.17 (−), 128.17 (+), 126.97 (−), 116.80 (−), 111.20 (−), 100.8 (−), 67.24 (+), 29.41 (+), 28.45 (+), 27.73 (+), 25.01 (+), 22.14 (+); LRMS-ES m/z: $M^+$ 361.0.

Example 30

Ethyl 2-Methyl-8-[(1-Phenyl-Cyclopropyl)Methoxy]imidazo[1,2-α]Pyridine-3-Carboxylate Mmonohydrochloride

Compound 30

Route B:

A stirred mixture of 2-amino-3-[(1-phenylcyclopropyl) methoxy]pyridine (2.82 g, 11.7 mmol, see example 23), ethyl 2-chloroacetoacetate (6.5 mL, 47 mmol) and molecular sieves (15.1 g, type 4 Å, beads, 8–12 mesh) in anhydrous methanol (55 mL) was refluxed for 39 h under argon. The molecular sieves were filtered off and the filtrate was concentrated in vacuo to give an oil which was dissolved in ethyl acetate (200 mL) and then washed successively with a 1:1 (v/v) mixture of saturated aq sodium bicarbonate and water (2×25 mL), and water (20 mL). The organic layer was dried over anhydrous magnesium sulfate and concentrated in vacuo to yield the crude product. Purification by dry column (600 mL funnel with 450 mL of silica gel 10–40μ, Sigma cat. S-6628) eluted with a mixture of ethyl acetate-hexanes (1:3 v/v, containing 0.5% v/v isopropylarnine) afforded 0.352 g (8.6% yield) of ethyl 2-methyl-8-[(1-phenylcyclopropyl) methoxy]imidazo[1,2-α]pyridine-3-carboxylate ($R_f$=0.30 in ethyl acetate-hexanes, 1:3 v/v, containing 0.5% v/v isopropylamine). A stirred solution of ethyl 2-methyl-8-[(1-phenylcyclopropyl)methoxy]imidazo[1,2-α]pyridine-3-carboxylate (0.190 g, 0.542 mmol) in a mixture of dichloromethane (3.5 mL) and anhydrous diethyl ether (3 mL) was treated with ethereal hydrogen chloride to form the hydrochloride salt. Concentration of the solution in vacuo gave a residue which was triturated in anhydrous diethyl ether to afford the title compound as an off-white solid (0.168 g, 80% yield). $^1$H-NMR (300 MHz, $CDCl_3$) δ 16.91 (br s, 1H, $^+$NH), 9.05 (d, 1H, Ar), 7.65 (d, 2H, Ar), 7.18 (m, 4H, Ar), 6.92 (d, 1H, Ar), 4.45 (q, 2H, $CH_3CH_2$), 4.32 (s, 2H, $CH_2O$), 3.03 (s, 3H, $CH_3$), 1.42 (t, 3H, $CH_3CH_2$), 1.15 (m, 4H, $CH_2CH_2$); $^{13}$C-NMR (75 MHz, $CDCl_3$, APT) δ 159.49 (+), 145.10 (+), 143.90 (+), 142.24 (+), 133.68 (+), 130.21 (−), 128.26 (−), 126.78 (−), 120.27 (−), 118.13 (−), 113.77 (+), 112.02 (−), 78.61 (+), 62.09 (+), 25.48 (+), 14.14 (−), 12.56 (−), 11.51 (+); LRMS-FAB m/z: $MH^+$ 351 (100%); Anal. calcd for $C_{21}H_{22}N_2O_3$.HCl: C, 65.20; H, 5.99; N, 7.24%. found: C, 64.87; H, 5.96; N, 7.20%.

Example 31

{2-Methyl-8-[(1-Phenylcyclopropyl)Methoxy]imidazo[1,2-α]Pyridin-3-yl}-Methanol Monohydrochloride

Compound 31

To a cold (0°), stirred solution of ethyl 2-methyl-8-[(1-phenylcyclopropyl)methoxy]imidazo[1,2-α]pyridine-3-carboxylate (0.629 g, 1.83 mmol, see example 30) in anhydrous tetrahydrofuran (12 mL) under argon was added lithium aluminum hydride (0.104 g, 2.74 mmol). The reaction mixture was stirred for 1 h at 0° C., then quenched with water (25 mL) and extracted successively with ethyl acetate (75 mL) and dichloromethane (3×30 mL). The organic extracts were combined, dried over anhydrous sodium sulfate and concentrated in vacuo to yield 0.485 g (86% yield) of {2-methyl-8-[(1-phenylcyclopropyl)methoxy]imidazo[1,2-α]pyridin-3-yl}methanol free base as a pale yellow solid. A stirred solution of the free amine (0.479 g, 1.55 mmol) in anhydrous methanol (27 mL) was treated with ethereal hydrogen chloride to form the hydrochloride salt. After the solvent was removed in vacuo, the residue was triturated in anhydrous diethyl ether to yield a gummy solid. Recrystallization of this material from a mixture of diethyl ether and methanol yielded 0.509 g (95% yield) of the title compound as an off-white solid. $^1$H-NMR (300 MHz, $CDCl_3$) δ 14.92 (s, 1H, $^+$NH), 8.41 (s, 1H, Ar), 7.57 (m, 2H, Ar), 7.21 (m, 2H, Ar), 7.10 (m, 1H, Ar), 6.96 (m, 1H, Ar), 6.70 (m, 1H, Ar), 4.86 (s, 2H, HOC<u>H</u>$_2$), 4.21 (s, 2H, $CH_2O$), 2.59 (s, 3H, $CH_3$), 1.06 (m, 4H, $CH_2CH_2$); $^{13}$C-NMR (75 MHz, $CDCl_3$, APT) δ 144.21 (+), 142.21 (+), 132.30(+), 131.66(+), 129.87 (−), 128.32(−), 126.81 (−), 123.23 (+), 119.12(−), 116.61 (−), 109.86 (−), 77.85 (+), 51.30 (+), 25.34 (+), 11.59 (+), 9.90 (−); LRMS-FAB m/z: $MH^+$ 309 (100%); Anal. calcd for $C_{19}H_{20}N_2O_2$.HCl: C, 66.18; H, 6.14; N, 8.12%. found: C, 64.67; H, 6.36; N, 7.64%.

Example 32

2,5-Dimethyl-8-(3-Phenylpropoxy)imidazo[1,2-α]Pyridine Monohydrochloride

Compound 32

Route A:

To sodium hydride (0.13 g, 80% oil dispersion) and 2,5-dimethyl-8-hydroxy-imidazo[1,2-α]pyridine (0.649 g, 4 mmol, Kaminski et al., *J. Med. Chem.* 1987, 30, 2031–2046) was added anhydrous dimethylformamide (30 mL) and the resultant mixture was stirred at ambient temperature for 10 min under argon. Then 1-bromo-3-phenylpropane (0.68 mL, 4.4 mmol) was added and the resultant mixture was heated at 75° C. for 3 h. After the reaction mixture was allowed to cool to room temperature, it was poured into ice water (60 mL) and extracted with ethyl acetate (2×60 mL). The organic extracts were combined, back-washed with brine (4×80 mL), dried over anhydrous sodium sulfate and concentrated in vacuo to yield the crude free base of the title compound. After purification by dry column (150 mL funnel, silica gel 10–40μ,Sigma cat. S-6628) eluted with mixtures of ethyl acetate-hexanes (1:5–1:3 v/v, containing 0.5% v/v isopropylamine), the free base ($R_f$=0.2 in ethyl acetate-hexanes, 2:1 v/v, containing 0.5% v/v isopropylamine) was dissolved in diethyl ether (30 mL) and treated with ethereal hydrogen chloride. Concentration of this solution in vacuo and trituration of the residual oil in diethyl ether (150 mL) afforded the title compound as a solid (1.12 g, 88% yield). $^1$H-NMR (300 MHz, $CD_3OD$) δ 7.91 (s, 1H, Ar), 7.28–7.19 (m, 5H, Ar), 7.14 (d, 2H, Ar), 4.29 (t, 2H, $CH_2O$), 2.87 (t, 2H, $CH_2Ar$), 2.67 (s, 3H, $CH_3$), 2.59 (s, 3H, $CH_3$), 2.24 (m, 2H, $CH_2$); $^{13}$C-NMR (75 MHz, $CD_3OD$, APT) δ 143.57 (+), 142.45 (+), 134.99 (+), 130.71 (+), 129.52 (−), 129.44 (−), 127.02 (−), 117.43 (−), 112.12 (−), 70.39 (+), 32.89 (+), 31.59 (+), 17.53 (31 ), 10.72 (−); LRMS-FAB m/z: $MH^+$ 281 (100%); Anal. calcd for $C_{18}H_{20}N_2O.HCl.1.5H_2O$: C, 62.88; H, 7.04; N, 8.15%. found: C, 62.79; H, 6.58; N, 8.03%.

Example 33

2,5-Dimethyl-8-[(1-Phenyl-Cyclopropyl)methoxy]imidazo[1,2-α]Pyridine Monohydrochloride

Compound 33

Route A:

1) To a cold (0° C.) solution of (1-phenyl-cyclopropyl) methanol (1.187 g, 8 mmol) and triethylamine (1.35 mL, 9.6 mmol) in dichloromethane (40 mL) was added dropwise neat methanesulfonyl chloride (0.76 mL, 9.6 mmol) under argon. The resultant mixture was stirred at 0° C. for 30 min and then at ambient temperature for 2.5 h. The reaction mixture was then diluted with dichloromethane (20 mL) and washed with water (60 mL). The organic layer was dried over anhydrous sodium sulfate and concentrated in vacuo to yield the desired mesylate, which was used in the next step without further purification.

2) To sodium hydride (0.23 g, 80% oil dispersion) and 2,5-dimethyl-8-hydroxy-imidazo[1,2-α]pyridine (1.14 g, 7 mmol, Kaminski et al., *J. Med. Chem.* 1987, 30, 2031–2046) was added anhydrous dimethylformamide (30 mL) and the resultant mixture was stirred at ambient temperature for 10 min under argon.

3) To the alkoxide (step 2) was quickly added a solution of the mesylate (step 1) in anhydrous dimethylformamide (10 mL) and the resultant mixture was heated at 75° C. for 15 h. After the reaction mixture was allowed to cool to room temperature, it was poured into a 5:1 (v/v) mixture of ice water and brine (120 mL) and extracted with ethyl acetate (2×100 mL). The organic extracts were combined, back-washed with brine (3×100 mL), dried over anhydrous sodium sulfate and concentrated in vacuo to give a slurry. Trituration of the slurry in ethyl acetate (20 mL) and filtration afforded unreacted 2,5-dimethyl-8-hydroxy-imidazo[1,2-α]pyridine) (0.17 g). Concentration of the filtrate in vacuo yielded the crude free base of the title compound. After purification by dry column (150 mL funnel, silica gel 10–40μ, Sigma cat. S-6628) eluted with a mixture of ethyl acetate-hexanes (1:2.5 v/v, containing 0.5% v/v isopropylamine), the free base of the title compound ($R_f$=0.22, ethyl acetate-hexanes, 2:1 v/v, containing 0.5% v/v isopropylamine) was dissolved in diethyl ether (40 mL) and treated with ethereal hydrogen chloride, giving the title compound as a solid (0.88 g, 33% yield). $^1$H-NMR (300 MHz, $CDCl_3$) δ 16.13 (s, 1H, $^+$NH), 7.63 (d, 2H, Ar), 7.38 (s, 1H, Ar), 7.28–7.17 (m, 2H, Ar), 7.11 (t, 1H, Ar), 6.80 (d, 1H, Ar), 6.69 (d, 1H, Ar), 4.21 (s, 2H, $CH_2O$), 2.71 (s, 3H, $CH_3$), 2.55 (s, 3H, $CH_3$), 1.19 (t, 2H, $CH_2$), 0.99 (t, 2H, $CH_2$); $^{13}$C-NMR (75 MHz, $CDCl_3$, APT) δ 143.11 (+), 142.38 (+), 135.59 (+), 133.29 (+), 130.21 (−), 128.23 (−), 127.77 (+), 126.68 (−), 115.71 (−), 110.20 (−), 109.20 (−), 77.89 (+), 65.69(+), 25.48 (+), 17.59 (−),15.13 (−),11.32 (+), 10.94 (−); LRMS-FAB m/z: $MH^+$ 293 (100%); Anal. calcd for $C_{19}H_{20}N_2O.HCl$: C, 69.40; H, 6.44; N, 8.52%. found: C, 68.74; H, 6.35; N, 8.32%.

Example 34

8-[3-(2,4-Dichlorophenyl)Propoxy]-2,5-Dimethylimidazo[1,2-α]pyridine Monohydrochloride

Compound 34

Route A:

1) To a cold (0° C.) solution of 3-(2,4-dichlorophenyl)-1-propanol (0.62 g, 3 mmol) and triethylamine (0.51 mL, 3.6 mmol) in dichloromethane (20 mL) was added dropwise neat methanesulfonyl chloride (0.29 mL, 3.6 mmol) under argon. The resultant mixture was stirred at 0° C. for 30 min and then at ambient temperature for 1 h. The reaction mixture was then diluted with dichloromethane (10 mL) and washed with water (30 mL). The organic layer was dried over anhydrous sodium sulfate and concentrated in vacuo to yield the desired mesylate, which was used in the next step without further purification.

2) To sodium hydride (0.10 g, 3.3 mmol, 80% oil dispersion) and 8-hydroxy-2,5-dimethylimidazo[1,2-α]pyridine (0.487 g, 3 mmol, Kaminski et al., *J. Med. Chem.* 1987, 30, 2031–2046) was added anhydrous dimethylformamide (20 mL) and the resultant mixture was stirred at ambient temperature for 10 min under argon.

3) To the alkoxide (step 2) was quickly added a solution of the mesylate (step 1) in anhydrous dimethylformamide (10 mL) and the resultant mixture was heated at 75° C. for 15 h. After the reaction mixture was allowed to cool to room temperature, it was poured into ice water (60 mL) and extracted with ethyl acetate (2×60 mL). The organic extracts were combined, back-washed with brine (4×80 mL), dried over anhydrous sodium sulfate and concentrated in vacuo to yield the crude free base of the title compound. After purification by dry column (150 mL funnel, silica gel 10–40μ, Sigma cat. S-6628) eluted with a mixture of ethyl acetate-hexanes (1:3 v/v, containing 0.5% v/v isopropylamine), the free base ($R_f$=0.25 in ethyl acetate-hexanes, 2:1 v/v, containing 0.5% v/v isopropylarnine) was dissolved in diethyl ether (40 mL) and treated with ethereal hydrogen chloride. The title compound was isolated as a white powder (0.78 g, 67% yield). $^1$H-NMR (300 MHz, $CDCl_3$) δ 16.55 (s, 1H, $^+$NH), 7.63 (d, 1H, Ar), 7.35 (s, 1H, Ar), 7.25 (d, 1H, Ar), 7.10 (q, 1H, Ar), 6.91 (d, 1H, Ar), 6.85 (d, 1H, Ar), 4.14 (t, 2H, $CH_2O$), 3.18 (t, 2H, $CH_2Ar$), 2.74 (s, 3H, $CH_3$), 2.60 (s, 3H, $CH_3$), 2.23 (m, 2H, $CH_2$; $^{13}$C-NMR (75 MHz, $CDCl_3$, APT) δ 143.32 (+), 137.66 (+), 135.68 (+), 134.32 (+), 133.47 (+), 132.84 (−), 132.08 (+), 128.70 (−), 127.47 (+), 127.21 (−), 115.80 (−), 108.93 (−), 108.88 (−), 68.82 (+), 29.28 (+), 28.50 (+), 17.51 (−), 10.87 (−); LRMS-FAB m/z: $M^+$ 349 (100%); Anal. calcd for $C_{18}H_{18}Cl_2N_2O.HCl$: C, 56.29; H, 4.99; N, 7.54%. found: C, 55.98; H, 4.95; N, 7.13%.

Example 35

Ethyl 8-[3-(2,4-Dichlorophenyl)Propoxy]-2-(Trifluoromethyl)imidazo[1,2-α]-Pyridine-3-Carboxylate Monohydrochloride Compound 35

Route B:

A stirred mixture of 2-amino-3-[3-(2,4-dichlorophenyl) propoxy]pyridine (1.50 g, 5.05 mmol, see example 1), ethyl 2-bromo-4,4,4-trifluoro-3-oxobutanoate (2.0 g, 7.6 mmol, E. Cherbuliez et al., *Helvetica Chimica Acta,* 1965, 48 (6), 1423–1427) and molecular sieves (2.0 g, type 4 Å, beads, 8–12 mesh) in anhydrous ethanol (10 mL) was refluxed for 20 h under argon. An additional aliquot of ethyl 2-bromo-4,4,4-trifluoro-3-oxobutanoate (2.0 g, 7.6 mmol) was added and the reaction mixture was refluxed for another 20 h. The molecular sieves were filtered off and the filtrate was concentrated in vacuo. Purification by column chromatography using as eluent a mixture of ethyl acetate-hexanes (1:8 v/v, containing 5% v/v triethylamine) yielded 2.10 g (90% yield) of the title compound as a free base. The free base was converted to the hydrochloride salt by treatment with ethereal hydrogen chloride to provide the title compound. $^1$H-NMR (300 MHz, $CDCl_3$) δ 9.00 (d, 1h, Ar), 7.30 (s, 1H, Ar), 7.15 (m, 2H, Ar), 6.95 (t, 1H, Ar), 6.70 (d, 1H, Ar), 4.40 (q, 2H, $OCH_2CH_3$), 4.2 (t, 2H, $CH_2O$), 2.95 (t, 2H, $CH_2$), 2.25 (qt, 2H, $CH_2$), 1.40 (t, 3H, $OCH_2CH_3$); $^{13}$C-NMR (75 MHz, $CDCl_3$, APT) δ 159.32 (+), 148.64 (+), 139.93 (+), 137.15 (+), 134.58 (+), 132.52 (+), 131.35 (−), 129.28 (−), 127.12 (−), 120.86 (+, q, 264Hz, $CF_3$), 120.48 (−), 115.91 (−), 106.02 (−), 68.24 (+), 61.46 (+), 29.30 (+), 28.78 (+), 13.85 (−); LRMS-ES m/z: $M^+$ 461.2.

Example 36

{8-[3-(2,4-Dichlorophenyl)Propoxy]-2-(Trifluoromethyl)imidazo[1,2-α]Pyridine-3-yl}Methanol Monohydrochloride Compound 36

To a stirred solution of ethyl 8-[3-(2,4-dichlorophenyl) propoxy]-2-(trifluoro-methyl)imidazo[1,2-α]pyridine-3-carboxylate (0.223 g, 0.483 mmol, see example 35) in anhydrous diethyl ether (20 mL) was added dropwise borane-methyl sulfide complex (2.0 mL, 20 mmol). The reaction mixture was stirred at ambient temperature for 42 h under argon and then heated at reflux for 3.5 h. Excess borane was subsequently hydrolyzed by dropwise addition of 5M aq sodium hydroxide (4 mL) to the cold (0° C.) reaction mixture. The resultant solution was stirred for 30 min and water (50 mL) was added. After successive extraction of the solution with diethyl ether (2×30 mL) and dichloromethane (30 mL), the organic extracts were combined, dried over anhydrous sodium sulfate and concentrated in vacuo to yield the crude desired product as a white solid. Purification by chromatography with a mixture of ethyl acetate-hexanes (1:1 v/v, containing 0.5% v/v isopropylamine) yielded 94.3 mg (47% yield) of {8-[3-(2,4-dichlorophenyl)propoxy]-2-(trifluoromethyl)imidazo[1,2-α]pyridin-3-yl}methanol as a pale yellow solid ($R_f$=0.41 in ethyl acetate-hexanes, 1:1 v/v, containing 0.5% v/v isopropylamine). A stirred suspension of {8-[3-(2,4-dichlorophenyl) propoxy]-2-(trifluoromethyl)imidazo[1,2-α]pyridin-3-yl}methanol (0.142 g, 0.339 mmol) in anhydrous methanol (5 mL) was treated with ethereal hydrogen chloride to form the hydrochloride salt. Concentration of the solution in vacuo and trituration of the residue in anhydrous diethyl ether afforded the title compound as an off-white solid (0.144 g, 93% yield). $^1$H-NMR (400 MHz, $CDCl_3/CD_3OD$) δ 8.46 (d, 1H, Ar), 7.39–7.45 (m, 2H, Ar), 7.35 (d, 1H, Ar), 7.27 (d, 1H, Ar), 7.19 (dd, 1H, Ar), 5.09 (s, 2H, $CH_2OH$), 4.36 (t, 2H, $CH_2O$), 2.99 (t, 2H, $CH_2Ar$), 2.26 (m, 2H, $CH_2CH_2CH_2$); $^{13}$C-NMR (100 MHz, $CDCl_3/CD_3OD$, APT) δ 146.38 (+), 138.09 (+), 136.58 (+), 135.35 (+), 133.50 (+), 132.24 (−), 129.94 (−), 128.28 (+), 128.06 (−), 124.01 (+), 122.05/119.36 (+), 120.49 (−), 119.12 (−), 112.57 (−), 70.26 (+), 52.25 (+), 29.76 (+), 29.10 (+); LRMS-ES m/z: $M^+$ 419.2 (100%); Anal. calcd for $C_{18}H_{15}N_2O_2Cl_2F_3.HCl$: C, 47.44; H, 3.54; N, 6.15%. found: C, 47.04; H, 3.54; N, 6.02%.

Example 37

Sodium 8-[3-(2,4-Dichlorophenyl)Propoxy]-2-Methylimidazo[1,2-α]Pyridine-3-Carboxylate Compound 37

A mixture of ethyl 8-[3-(2,4-dichlorophenyl)propoxy]-2-methylimidazo[1,2-α]pyridine-3-carboxylate (500 mg, 1.23 mmol, see example 16) and 1M aq NaOH (5.6 mL, 5.6 mmol) in a 1:1 (v/v) mixture of methanol and water (40 mL) was refluxed for 2 h. The reaction mixture was allowed to cool to room temperature and adjusted to pH 7.0 with 1M aq HCl (10 mL), giving a solid (335 mg, 76% yield). The solid was then dissolved in a 1:1 (v/v) mixture of methanol and dichloromethane (30 mL) and to the resultant solution was added NaOH (37 mg). The mixture was stirred for 30 min and concentrated to dryness to yield 371 mg of the title compound. $^1$H-NMR (300 MHz, $D_2O$) δ 8.35 (d, 1H, Ar), 6.50 (m, 2H, Ar), 6.40 (d, 1H, Ar), 6.10 (t, 1H, Ar), 5.75 (d, 1H, Ar), 3.3 (m, 2H, $CH_2O$), 2.85 (s, 3H, $CH_3$), 2.20 (t, 2H, $CH_2$), 1.4 (m, 2H, $CH_2$); $^{13}$C-NMR (75 MHz, $D_2O$, APT) δ 168.95 (+), 148.19 (+), 147.18 (+), 139.70 (+), 138.48 (+), 135.06 (+), 132.83 (+), 132.33 (−), 129.52 (−), 127.87 (−), 121.71 (−), 119.99 (+), 113.35 (+), 104.84 (+), 68.22 (+), 29.81 (+), 29.12 (+), 15.68 (−); LRMS-ES m/z: $M^+$ 379.2.

Example 38

2-Isopropyl-8-[(1-Phenyl-Cyclopropyl)Methoxy]imidazo[1,2-α]Pyridine Monohydrochloride Compound 38

A stirred mixture of 2-amino-3-[(1-phenylcyclopropyl) methoxy]pyridine (0.84 g, 3.50 mmol, see example 23), 1-bromo-3-methyl-2-butanone (0.69 g, 4.2 mmol) and molecular sieves (4.2 g, type 4 Å, beads, 8–12 mesh) in anhydrous ethanol (10 mL) was refluxed for 24 h under argon. The molecular sieves were filtered off and the filtrate was concentrated in vacuo. The residue was dissolved in a 1:1 (v/v) mixture of saturated aq sodium bicarbonate and water (20 mL) and then extracted with ethyl acetate (3×40 mL). The organic extracts were combined, washed with water (2×5 mL), dried over anhydrous magnesium sulfate and concentrated in vacuo to yield the crude product. Purification by dry column (600 mL funnel filled with 300 mL of silica gel 10–40μ, Sigma cat. S-6628) eluted with a mixture of ethyl acetate-hexanes (1:3 v/v, containing 0.5% v/v isopropylamine) yielded 0.814 g (76% yield) of 2-isopropyl-8-[(1-phenyl-cyclopropyl)methoxy]imidazo[1,2-α]pyridine as a free base ($R_f$=0.60 in ethyl acetate-hexanes, 1:1 v/v, containing 0.5% v/v isopropylamine). A stirred solution of the free amine (0.755 g, 2.46 mmol) in anhydrous diethyl ether (10 mL) was treated with ethereal hydrogen chloride (50 mL) to form the hydrochloride salt. After 1 h, the solvent was decanted and the title compound was isolated as a solid (0.844 g, quantitative). $^1$H-NMR (300 MHz, $CDCl_3$) δ 15.59 (br s, 1H, $^+$NH), 8.36 (m, 1H, Ar), 7.85 (d, 1H, Ar), 7.63 (d, 2H, Ar), 7.24 (m, 2H, Ar), 7.13 (m, 1H, Ar), 7.01 (t, 1H, Ar), 6.74 (d, 1H, Ar), 4.29 (s, 2H, $CH_20$), 3.64 (m, 1H, CH), 1.40 (d, 6H, $2CH_3$), 1.12 (m, 4H, $CH_2CH_2$); $^{13}$C-NMR (75 MHz, $CDCl_3$, APT) δ 145.64 (+), 144.89 (+), 142.33 (+), 133.36 (+), 130.04 (−), 128.27 (−), 126.78 (−), 120.09 (−), 116.68 (−), 110.31 (−), 109.82 (−), 77.99 (+), 25.51 (−), 25.45 (+), 21.99 (−), 11.45 (+); LRMS-ES m/z: $MH^+$ 307.3.

Example 39

3-Chloro-2-Methyl-8-[(1-Phenyl-Cyclopropyl)Methoxy]imidazo[1,2-α]Pyridine Monohydrochloride Compound 39

A solution of 2-methyl-8-[(1-phenyl-cyclopropyl)methoxy]imidazo[1,2-α]pyridine (1.02 g, 3.6 mmol, see example 13) and N-chlorosuccinimide (0.530 g, 4 mmol) in ethanol (13 mL) was stirred at room temperature for 1 h. The organic solvent was evaporated in vacuo and to the residue was added water (20 mL). The resultant mixture was extracted with dichloromethane (3×20 mL), and the organic extracts were combined, back-washed with brine (50 mL) and dried over anhydrous sodium sulfate. The solvent was removed in vacuo and the crude product was purified by dry column (60 mL funnel, silica gel 10–40μ, Sigma cat. S-6628) eluted with a mixture of ethyl acetate-hexanes (1:9 v/v, containing 0.5% v/v isopropylamine) to give the free amine of the title product. The free base was then dissolved in anhydrous diethyl ether and treated with ethereal hydrogen chloride to give 0.245 g (20% yield) of the title compound as an off-white powder. $^1$H-NMR (300 MHz, $CD_3OD$) δ 7.59 (t, 1H, Ar), 7.43 (m, 2H, Ar), 7.24–7.08 (m, 3H, Ar), 6.73 (t, 1H, Ar), 6.51 (d, 1H, Ar), 4.20 (s, 2H, $CH_2O$), 2.32 (s, 3H, $CH_3$), 1.05 (m, 4H, $CH_2$); $^{13}$C-NMR (75 MHz, $CD_3OD$, APT) δ 148.7 (+), 144.2 (+), 138.7 (+), 138.1 (+), 129.7 (−), 129.2 (−), 127.3 (−), 116.5 (−), 114.3 (−), 108.4 (+), 104.1 (−), 77.5 (+), 25.8 (+), 13.0 (+), 12.3 (−); LRMS-EI m/z: $M^+$ 312 (46).

Example 40

3-(Dimethylamino)Methyl-2-Methyl-8-[(1-Phenyl-Cyclopropyl)methoxy]-imidazo[1,2-α]Pyridine Dihydrochloride Compound 40

A solution of 2-methyl-8-[(1-phenyl-cyclopropyl)methoxy]imidazo[1,2-α]pyridine (1.00 g, 3.6 mmol, see example 13), dimethylamine hydrochloride (0.408 g, 5 mmol), and paraformaldehyde (0.15 g, 5 mmol) in methanol (12 mL) was refluxed for 1.5 h. Concentration of the solution gave a residue which was dissolved in a mixture of water (8 mL) and saturated aq sodium bicarbonate (8 mL). The resultant solution was extracted with dichloromethane (3×20 mL), the organic extracts were combined, dried over anhydrous sodium sulfate, and concentrated in vacuo. Purification of the crude product by dry column (60 mL funnel, silica gel 10–40μ, Sigma cat. S-6628) eluted with a mixture of ethyl acetate-hexanes (2.90:1 v/v, containing 0.5% v/v isopropylamine) gave the title compound as a free base. The free base was then dissolved in anhydrous diethyl ether and treated with ethereal hydrogen chloride to afford 0.7 g (58% yield) of the title compound. $^1$H-NMR (300 MHz, $CDCl_3$) δ 7.72 (m, 1H, Ar), 7.42–7.09 (m, 5H, Ar), 6.50 (t, 1H, Ar), 6.28 (d, 1H, Ar), 4.27 (s, 2H, $CH_2O$), 3.53 (s, 2H, $CH_2N$), 2.39 (s, 3H, $CH_3$), 2.15 (s, 6H, $CH_3$), 1.02 (m, 4H, $CH_2$); $^{13}$C-NMR (75 MHz, $CDCl_3$, APT) δ 147.8 (+), 143.0 (+), 140.8 (+), 138.9 (+), 128.7 (−), 128.2 (−), 126.3 (−), 117.7 (+), 117.4 (−), 111.1 (−), 102.6 (−), 76.0 (+), 52.5 (+), 44.9 (−), 25.0 (+), 13.4 (−), 12.2 (+); LRMS-ES m/z: $M^+$ 336.4.

Example 41

3-Acetamido-8-[3-(2,4-Dichlorophenyl)Propoxy]-2-Methylimidazo[1,2-α]Pyridine Monohydrochloride Compound 41

A solution of 3-amino-8-[3-(2,4-dichlorophenyl)propoxy]-2-methylimidazo[1,2-α]pyridine (0.245 g, 0.7 mmol, see example 26) and acetyl chloride (0.09 mL, 1 mmol) in dichloromethane (8 mL) was stirred at room temperature for 2 h. To the mixture was added water (5 mL) and saturated aq sodium bicarbonate (5 mL) and the layers were separated. After the aqueous layer was extracted with dichloromethane (3×10 mL), the organic extracts were combined, dried over anhydrous sodium sulfate, and concentrated in vacuo. The residue was purified by dry column (60 mL funnel, silica gel 10–40μ, Sigma cat. S-6628) eluted with a mixture of ethyl, acetate-hexanes (2:1 v/v, containing 0.5% v/v isopropylamine) to provide the title compound as a free base. The free base was then dissolved in anhydrous diethyl ether and treated with ethereal hydrogen chloride to yield 0.11 g (40% yield) of the title compound. $^1$H-NMR (300 MHz, $CD_3OD$) δ 10.31 (s, 1H, NH), 8.07 (m, 1H, Ar), 7.40–7.22 (m, 5H, Ar), 4.36 (t, 2H, $CH_2O$), 3.02 (t, 2H, $CH_2Ar$), 2.46 (s, 3H, $CH_3$), 2.31 (s, 3H, $CH_3$), 2.25 (qt, 2H, $CH_2$); $^{13}$C-NMR (75 MHz, $CD_3OD$, APT) δ 173.9 (+), 145.4 (+), 138.8 (+), 135.7 (+), 133.7 (+), 132.9 (−), 132.7 (+), 130.1 (−), 129.8 (+), 128.4 (−), 120.0 (+), 118.6 (−), 118.5 (−), 112.0 (−), 70.3 (+), 30.1 (+), 29.6 (+), 22.6 (−), 9.3 (−); LRMS-ES m/z: $M^+$ 392.3.

Example 42

8-[3-(2,4-Dichlorophenyl)Propoxy]imidazo[1,2-α]Pyridine Monohydrochloride

Compound 42

A mixture containing bromoacetaldehyde diethyl acetal (332 mg, 1.69 mmol), water (10 mL) and concentrated aq HCl (0.33 mL) was stirred at room temperature for 2.5 h. The mixture was then heated at 100° C. for 20 min, the mixture, which become homogenous during the course of the reaction, was allowed to cool to room temperature. Sodium bicarbonate (184 mg, 1.65 mmol) and 2-amino-3-[3-(2,4-dichlorophenyl)propoxy]pyridine (400 mg, 1.35 mmol, see example 1) were added and the resultant mixture was stirred at room temperature for 20 h. The reaction mixture was heated at 65° C. for 30 min to ensure consumption of starting materials. After the reaction mixture had cooled to room temperature, water (20 mL) and ethyl acetate (20 mL) were added and the layers were separated. The aqueous layer was extracted twice more with ethyl acetate (2×20 mL), and the organic extracts were combined and dried over anhydrous sodium sulfate. Concentrated of the solution in vacuo yielded the crude title compound as a free base. After purification by dry column eluted with a mixture of ethyl acetate-hexanes (2:1 v/v, containing 0.5% isopropylamine), the free base was converted into the hydrochloride salt by treatment with ethereal hydrogen chloride. $^{1}$H-NMR (300 MHz, $CDCl_3$) δ 8.45 (d, 1H, Ar), 8.30 (s, 1H, Ar), 7.80 (s, 1H, Ar), 7.40 (d, 1H, Ar), 7.10–6.90 (m, 4H, Ar), 4.10 (m, 2H, $CH_2O$), 3.00 (t, 2H, $CH_2$), 2.15 (m, 2H, $CH_2$); $^{13}$C-NMR (75 MHz, $CDCl_3$, APT) δ 144.88 (+), 137.28 (+), 134.27 (+), 133.30 (+), 132.16 (−), 132.13 (+), 128.76 (−), 127.02 (−), 122.57 (−), 120.50 (−), 117.25 (−), 115.74 (−), 109.18 (−), 68.92 (+), 29.09 (+), 28.37(+); LRMS-ES m/z: $M^+$ 321.2.

Example 43

3-Amino-2-Methyl-8-[(1-Phenyl-Cyclopropyl)Methoxy]imidazo[1,2-α]Pyridine Monohydrochloride

Compound 43

Route B:

To a cold (0° C.) solution of sodium hydrogen sulfite (17.8 g, 171 mmol) in water (105 mL) was added acetaldehyde (16.7 mL, 299 mmol), and the resultant mixture was stirred at ambient temperature for 30 min. 2-Amino-3-[(1-phenylcyclopropyl)methoxy]pyridine (4.10 g, 17.1 mmol, see example 23) was added, and the reaction mixture was heated to 90° C. 1,4-Dioxane (85 mL) was added to obtain a clear solution and the stirred mixture was heated at 90° C. for 2 h. A solution of sodium cyanide (9.80 g, 200 mmol) in water (50 mL) was added, and the reaction mixture was then refluxed for 25.5 h. 5M Aqueous sodium hydroxide (75 mL) was added, and the mixture was allowed to cool to ambient temperature before being poured into water (500 mL). Following extraction of the aqueous layer with ethyl acetate (4×400 mL), the organic extracts were combined, washed with brine (2×150 mL), dried over anhydrous sodium sulfate and concentrated in vacuo to yield the crude product as a free base. Purification by dry column (600 mL funnel filled with 400 mL of silica gel 10–40μ, Sigma cat. S-6628) eluted with ethyl acetate gave 1.77 g (35% yield) of the title compound as a free base (Rf=0.14 in ethyl acetate). A stirred solution of the free base (0.569 g, 1.94 mmol) in anhydrous dichloromethane (8 mL) was treated with ethereal hydrogen chloride to form the hydrochloride salt. After 1 h, the solvent was decanted and the resultant solid was triturated in anhydrous diethyl ether (50 mL). Decantation of the solvent provided the title compound as a solid (0.653 g, 100% yield). $^{1}$H-NMR (300 MHz, $CD_3OD$) δ 8.06 (m, 1H, Ar), 7.42 (m, 2H, Ar), 7.14–7.28 (m, 5H, Ar), 4.44 (s, 2H, $CH_2O$), 3.30 (m, 2H, $NH_2$), 2.43 (s, 3H, $CH_3$), 1.12 (m, 4H, $CH_2CH_2$); $^{13}$C-NMR (75 MHz, $CD_3OD$, APT) δ 145.28 (+), 143.76 (+), 130.35 (+), 129.38 (−), 129.30 (−), 129.06 (+), 127.54 (−), 118.82 (+), 117.42 (−), 117.33 (−), 109.94 (−), 78.65 (+), 25.58 (+), 13.49 (+), 8.79 (−); LRMS-ES m/z: $MH^+$ 294.3; Anal. calcd for $C_{18}H_{19}N_3O.HCl$: C, 65.55; H, 6.11; N, 12.74%. found: C, 58.85; H, 6.08; N, 11.33%.

Example 44

8-(1-Indolepropoxy)-2-(Trifluoromethyl)imidazo[1,2-α]Pyridine Monohydrochloride

Compound 44

Route A:

1) To sodium hydride (0.9 g, 30 mmol, 80% oil dispersion) and indole (2.81 g, 24 mmoles) was added anhydrous dimethylformamide (50 mL). The resultant mixture was stirred at room temperature under argon for 1 h. Then neat 1,3-dibromopropane (7.3 mL, 72 mmol) was added and the reaction mixture was stirred at room temperature for 20 h. The reaction mixture was poured into water (120 mL) and the resultant slurry was extracted with diethyl ether (3×100 mL). After the organic extracts were combined and concentrated in vacuo, the crude material was purified by dry column chromatography (350 mL funnel filled with Silica 10–40μ, Sigma cat. S-6628) using as eluent a mixture of ethyl acetate and hexanes (1:49 v/v, containing 0.2% v/v isopropylamine) to yield 1.43 g of N-(3-bromopropyl)indole.

2) A mixture of 2-amino-3-hydroxypyridine (2.18 g, 19.4 mmol), bromo-1,1,1-trifluoroacetone (9.1 g, 42.6 mmol), and molecular sieves (6.3 g, 8–12 mesh beads) in anhydrous methanol (50 mL) was refluxed for 24 h. After the molecular sieves were filtered off and the solvent was evaporated in vacuo, the residue was dissolved in water (150 mL) and the resultant mixture was extracted with diethyl ether (2×150 mL). The combined organic extracts were dried over anhydrous sodium sulphate and the solvent was evaporated in vacuo to provide the crude 8-hydroxy-2-(trifluoromethyl)imidazo[1,2-α]pyridine. Purification by column chromatography using as eluent a mixture of ethyl acetate and isopropylamine (98:2 v/v) yielded 0.7 g of pure 8-hydroxy-2-(trifluoromethyl)imidazo[1,2-α]pyridine.

3) To anhydrous sodium carbonate (0.45 g, 4.2 mmol) was added 8-hydroxy-2-(trifluoromethyl)imidazo[1,2-α]pyridine (0.42 g, 2.06 mmol, from step 2) and anhydrous dimethylformamide (40 mL). The resultant mixture was stirred for 20 min and then a solution of N-(3-bromopropyl)indole (0.58 g, 2.43 mmol, from step 1) in anhydrous dimethylformamide (10 mL) was added. The reaction mixture was stirred at room temperature for 20 h, poured into water (150 mL) and the resultant mixture was extracted with ethyl acetate (3×100 mL). The combined organic extracts were back-washed with brine (100 mL), dried over anhydrous sodium sulphate and concentrated in vacuo to provide the crude title compound. Purification by column chromatography using as eluent mixtures of ethyl acetate and hexanes (1:4, 1:1, 2: 1, v/v, containing 0.5% v/v isopropylamine) yielded 130 mg of pure free base ($R_f$=0.83 in ethyl acetate-hexanes, 2:1 v/v, containing 0.5% v/v isopropylamine) of the title compound. The free base was converted into its hydrochloride salt by standard procedure. $^{1}$H-NMR (300 MHz, $CD_3OD$) δ 8.77 (d, 1H, Ar), 8.31 (d, 1H, Ar), 7.45–6.88 (m, 8H, Ar), 4.47 (t, 2H, $OCH_2$), 4.17 (t, 2H, $CH_2N$), 2.43 (qt, 2H, $CH_2$); $^{13}$C-NMR (75 MHz, $CD_3OD$, APT) δ 146.4 (+), 137.7 (+), 137.4 (+), 129.9 (+), 129.0 (−), 127.8 (+), 127.3 (+), 122.3 (−), 122.2 (−), 121.6 (−), 120.1 (−), 119.1 (−), 117.8 (−), 112.7 (−), 110.3 (−), 103.3 (+), 103.1 (+), 68.5 (+), 43.4 (+), 30.4 (+); MS (ES) m/z 360.6.

Example 45

ASSESSMENT OF ANTIARRHYTHMIC EFFICACY

Antiarrhythmic efficacy may be assessed by investigating the effect of a compound on the incidence of cardiac arrhythmias in anesthetized rats subjected to coronary artery occlusion. Rats weighing 200–300 gms are subjected to preparative surgery and assigned to groups in a random block design. In each case, the animal is anesthetized with pentobarbital during surgical preparation. The left carotid artery is cannulated for measurement of mean arterial blood pressure and withdrawal of blood samples. The left jugular vein is also cannulated for injection of drugs. The thoracic cavity is opened and a polyethylene occluder loosely placed around the left anterior descending coronary artery. The thoracic cavity is then closed. An ECG is recorded by insertion of electrodes placed along the anatomical axis of the heart. In a random and double-blind manner, an infusion of vehicle or the compound to be tested is given about 15 min post-surgery. After 5 minutes infusion, the occluder is pulled so as to produce a coronary artery occlusion. ECG, arrhythmias, blood pressure, heart rate and mortality are monitored for 15 minutes after occlusion. Arrhythmias are recorded as ventricular tachycardia (VT) and ventricular fibrillation (VF) and scored according to Curtis, M. J. and Walker, M. J. A., *Cardiovasc. Res.* 22:656 (1988) (see Table 1).

TABLE 1

| Score | Description |
|---|---|
| 0 | 0–49 VPBs |
| 1 | 50–499 VPBs |
| 2 | >499 VPBs and/or 1 episode of spontaneously reverting VT or VF |
| 3 | >1 episode of VT or VF or both (>60 s total combined duration) |
| 4 | VT or VF or both (60–119 s total combined duration) |
| 5 | VT or VF or both (>119 s total combined duration) |
| 6 | fatal VF starting at >15 min after occlusion |
| 7 | fatal VF starting at between 4 min and 14 min 59 s after occlusion |
| 8 | fatal VF starting at between 1 min and 3 min 59 s after occlusion |
| 9 | fatal VF starting <1 min after occlusion |

Where:
VPB = ventricular premature beats
VT = ventricular tachycardia
VP = ventricular fibrillation Rats are excluded from the study if they did not exhibit pre-occlusion serum oncentrations within the range of 2.9–3.9 mM. Occlusion is associated with R-wave height and "S-T" segment elevation; and an occluded zone (measured after death by cardiogreen dye perfusion) in the range of 25%–50% of total left-ventricular weight.

Results of the test compounds may be expressed as values of a given infusion rate in micromol/kg/min. ($ED_{50}$AA) which will reduce the arrhythmia score in treated animals to 50% of that shown by animals treated only with the vehicle in which the test compound(s) is dissolved. For example, Compound 3 shows an $ED_{50}$AA value of 5.

Example 46

MEASUREMENT OF CARDIOVASCULAR AND BEHAVIORAL EFFECTS

Preparative surgery is performed in Sprague Dawley rats weighing 200–300 gm and anaesthetized with 65 mg/kg (i.p.) pentobarbital. The femoral artery and vein are cannulated using polyethylene (PE)-10 tubing. Prior to surgery, this PE-10 tubing had been annealed to a wider gauge (PE-50) tubing for externalization. The cannulated PE-10/PE-50 tubing is passed through a trocar and exteriorised together with three (lead II) limb ECG leads (see below). The trocar is threaded under the skin of the back and out through a small incision at the mid-scapular region. A ground ECG electrode is inserted subcutaneously using a 20 gauge needle with the lead wire threaded through it. To place the other ECG electrodes, a small incision is made in the anterior chest region over the heart and ECG leads are inserted into the subcutaneous muscle layer in the region of the heart using a 20 guage needle. Other ECG leads are inserted into the subcutaneous muscle layer in the region near the base of the neck and shoulder (right side). The animal is returned to a clean recovery-cage with free access to food and water. The treatment and observational period for each animal commenced after a 24-hour recovery period.

A 15 min observational period is recorded followed by the intravenous infusion regime of the test compound at an initial dose of 2.0 μmol/kg/min (at 1 ml/hr). This rate is doubled every 5 minutes until one of the following effects is observed:

a) partial or complete convulsions b) severe arrhythmias c) bradycardia below 120 beats/min d) hypotension below 50 mmHg e) the dose exceeds 32 times the initial starting dose (i.e. 64 μmol/kg/min).

Blood pressure (BP), heart rate (HR) and ECG variables are continuously recorded while behavioral responses are also monitored and the total accumulative drug dose and drug infusion rate at which the response (such as convulsion, piloerection, ataxia, restlessness, compulsive chewing, lip-smacking, wet dog shake etc.) occurred are recorded.

Blood Samples

Estimates of plasma concentrations of the test compound are determined by removing a 0.5 ml blood sample at the end of the experiment. Blood samples are centrifuged for 5 min at 4600×g and the plasma decanted. Brain tissue samples are also extracted and kept frozen (−20° C.) along with the plasma samples for chemical analysis.

Data Analysis

Electrocardiograph (ECG) parameters: PR, QRS, $QT_1$ (peak of T-wave), $QT_2$ (midpoint of T-wave deflection) and hemodynamic parameters: BP and HR are analyzed using the automated analysis function in LabView (National Instruments) with a customized autoanalysis software (Nortran Pharmaceuticals). The infused dose producing 25% from control ($D_{25}$) for all recorded ECG variables is determined.

Table 2 describes the results of the tests as $D_{25}$ (micromol/kg) which are the doses required to produce a 25% increase in the ECG parameter measured (ne=not estimated). The increases in P-R interval and QRS interval indicate cardiac sodium channel blockade while the increase in Q-T interval indicates cardiac potassium channel blockade.

TABLE 2

| Compound | PR | QRS | QT |
|---|---|---|---|
| 1 | 14 | 12 | 8 |
| 2 | 24 | ne | 16 |
| 3 | 21 | ne | 16 |

Example 47

ELECTROPHYSIOLOGICAL TEST (IN VIVO)

This experiment determines the potency of the test compound for its effects on haemodynamic and electrophysiological parameters under non-ischemic conditions.

Methods

Surgical Preparation

Male Sprague-Dawley rats weighing between 250–350 g are used. They are randomly selected from a single group and anesthetized with pentobarbital (65 mg/kg, ip.) with additional anesthetic given if necessary.

The trachea is cannulated and the rat is artificially ventilated at a stroke volume of 10 ml/kg, 60 strokes/minute. The right external jugular vein and the left carotid artery are cannulated for intravenous injections of compounds and blood pressure (BP) recording, respectively.

Needle electrodes are subcutaneously inserted along the suspected anatomical axis (right atrium to apex) of the heart for ECG measurement. The superior electrode is placed at the level of the right clavicle about 0.5 cm from the midline, while the inferior electrode is placed on the left side of the thorax, 0.5 cm from the midline and at the level of the ninth rib.

Two Teflon-coated silver electrodes are inserted through the chest wall using 27G needles as guides and implanted in the epicardium of left ventricle (4–5 mm apart). Square pulse stimulation is provided by a stimulator controlled by a computer. In-house programmed software is used to determine the following: threshold current (iT) for induction of extra systoles, maximum following frequency (MFF), effective refractory period (ERP) and ventricular flutter threshold (VTt). Briefly, iT is measured as the minimal current (in μA) of a square wave stimulus required to capture and pace the heart at a frequency of 7.5 Hz and a pulse width of 0.5 msec; ERP is the minimum delay (in msec) for a second stimulus required to cause an extra systole with the heart entrained at a frequency of 7.5 Hz (1.5×iT and 0.2 msec pulse width), MFF is the maximum stimulation frequency (in Hz) at which the heart is unable to follow stimulation (1.5×iT and 0.2 msec pulse width); VTt is the minimum pulse current (in μA) to evoke a sustained episode of VT (0.2 msec pulse width and 50 Hz) (Howard, P. G. and Walker, M. J. A., *Proc. West. Pharmacol. Soc.* 33:123–127 (1990)).

Blood pressure (BP) and electrocardiographic (ECG) parameters are recorded and analyzed using LabView (National Instruments) with a customized autoanalysis software (Nortran Pharmaceuticals Inc.) to calculate mean BP (mmHg, ⅔ diastolic+⅓ systolic blood pressure), HR (bpm, 60/R-R interval); PR (msec, the interval from the beginning of the P-wave to the peak of the R-wave), QRS (msec, the interval from the beginning of the R-wave due to lack of Q wave in rat ECG, to the peak of the S-wave), QT (msec, the interval from the beginning of the R-wave to the peak of the T-wave).

Experimental Protocol

The initial infusion dose is chosen based on a previous toxicology study of the test compound in conscious rats. This is an infusion dose that did not produce a 10% change from pre-drug levels in haemodynamic or ECG parameters.

The animal is left to stabilize prior to the infusion treatment according to a predetermined random and blind table. The initial infusion treatment is started at a rate of 0.5 ml/hr/300 g (i.e., 0.5 μmol/kg/min). Each infusion dose is doubled (in rate) every 5 minutes. All experiments are terminated at 32 ml/hr/300 g (i.e., 32 μmol/kg/min). Electrical stimulation protocols are initiated during the last two minutes of each infusion level.

Data Analyses

Responses to test compounds are calculated as percent changes from pre-infusion values; this normalization is used to reduce individual variation. The mean values of BP and ECG parameters at immediately before the electrical stimulation period (i.e., 3 min post-infusion) are used to construct cumulative dose-response curves. Data points are fit using lines of best fit with minimum residual sum of squares (least squares; SlideWrite program; Advanced Graphics Software, Inc.). $D_{25}$'s (infused dose that produced 25% change from pre-infusion value) are interpolated from individual cumulative dose-response curves and used as indicators for determining the potency of compounds of the present invention.

Example 48

CANINE VAGAL-AF MODEL

General Methods

Mongrel dogs of either sex weighing 15–49 kg are anesthetized with morphine (2 mg/kg im initially, followed by 0.5 mg/kg IV every 2 h) and α-chloralose (120 mg/kg IV followed by an infusion of 29.25 mg/kg/h; St.-Georges et al., 1997). Dogs are ventilated mechanically with room air supplemented with oxygen via an endotracheal tube at 20 to 25 breaths/minute with a tidal volume obtained from a nomogram. Arterial blood gases are measured and kept in the physiological range ($SAO_2$>90%, pH 7.30–7.45). Catheters are inserted into the femoral artery for blood pressure recording and blood gas measurement, and into both femoral veins for drug administration and venous sampling. Catheters are kept patent with heparinized 0.9% saline solution. Body temperature is maintained at 37–40° C. with a heating blanket.

The heart is exposed via a medial thoracotomy and a pericardial cradle is created. Three bipolar stainless steel, Teflon™-coated electrodes are inserted into the right atria for recording and stimulation, and one is inserted into the left atrial appendage for recording. A programmable stimulator (Digital Cardiovascular Instruments, Berkeley, Calif.) is used to stimulate the right atrium with 2 ms, twice diastolic threshold pulses. Two stainless steel, Teflon™-coated electrodes are inserted into the left ventricle, one for recording and the other for stimulation. A ventricular demand pacemaker (GBM 5880, Medtronics, Minneapolis, Minn.) is used to stimulate the ventricles at 90 beats/minute when (particular during vagal-AF) the ventricular rate became excessively slow. A P23 ID transducer, electrophysiological amplifier (Bloom Associates, Flying Hills, Pa.) and paper recorder (Astromed MT-95000, Toronto, ON, Canada) are used to record ECG leads II and III, atrial and ventricular electrograms, blood pressure and stimulation artefacts. The vagi are isolated in the neck, doubly-ligated and divided, and electrodes inserted in each nerve (see below). To block changes in β-adrenergic effects on the heart, nadolol is administered as an initial dose of 0.5 mg/kg iv, followed by 0.25 mg/kg IV every two hours.

Atrial Fibrillation Model

Drug effects to terminate sustained AF maintained during continuous vagal nerve stimulation are assessed. Unipolar hook electrodes (stainless steel insulated with Teflon™, coated except for the distal 1–2 cm) are inserted via a 21 gauge needle within and parallel to the shaft of each nerve.

In most experiments, unipolar stimuli are applied with a stimulator (model DS-9F, Grass Instruments, Quincy, Mass.) set to deliver 0.1 ms square-wave pulses at 10 Hz and a voltage 60% of that required to produce asystole. In some experiments, bipolar stimulation is used. The voltage required to produce asystole ranged between 3–20 volts. Under control conditions, a short burst of rapid atrial pacing (10 Hz, four times diastolic threshold) is delivered to induce AF which is ordinarily sustained for more than 20 minutes. The vagal stimulation voltage is adjusted under control conditions, and then readjusted after each treatment to maintain the same bradycardic effect. AF is defined as rapid (>500 minute under control conditions), irregular atrial rhythm with varying electrogram morphology.

Measurement of Electrophvsiological Variables and Vagal Response

Diastolic threshold current is determined at a basic cycle length of 300 ms by increasing the current 0.1 mA incrementally until stable capture is obtained. For subsequent protocols current is set to twice diastolic threshold. Atrial and ventricular ERP is measured with the extrastimulus method, over a range of S1S2 intervals at a basic cycle length of 300 ms. A premature extrastimulus S2 is introduced every 15 basic stimuli. The S1S2 interval is increased in 5 ms increments until capture occurred, with the longest S1S2 interval consistently failing to produce a propagated response defining ERP. Diastolic threshold and ERP are determined in duplicate and averaged to give a single value. These values are generally within 5 ms. The interval between the stimulus artefact and the peak of the local electrogram is measured as an index of conduction velocity. AF cycle length (AFCL) is measured during vagal-AF by counting the number of cycles (number of beats −1) over a 2-second interval at each of the atrial recording sites. The three AFCLs measurements are averaged to obtain an overall mean AFCL for each experimental condition.

The stimulus voltage-heart rate relationship for vagal nerve stimulation is determined under control conditions in most experiments. The vagal nerves are stimulated as described above with various voltages to determine the voltage which caused asystole (defined as a sinus pause greater than 3 seconds). The response to vagal nerve stimulation is confirmed under each experimental condition and the voltage adjusted to maintain the heart rate response to vagal nerve stimulation constant. In cases in which is is not possible to produce asystole, vagal nerve stimulation is adjusted to a voltage which allowed two 20-minute episodes of vagal-AF to be maintained under control conditions (see below).

Experimental Protocols

One of the experimental groups studied is summarized in Table 3. Each dog received only one drug at doses indicated in Table 3. The first series of experiments are dose ranging studies, followed by blinded study in which 1–3 doses are given. All drugs are administered IV via an infusion pump, with drug solutions prepared freshly in plastic containers on the day of the experiment. Vagal stimulation parameters are defined under control conditions as described above, and maintenance of AF during 20 minutes of vagal nerve stimulation under control conditions is verified. After the termination of AF, the diastolic threshold and ERP of the atrium and ventricle are determined. Subsequently, these variables are reassessed in the atrium under vagal nerve stimulation. Electrophysiological testing usually took 15–20 minutes. The heart rate response to vagal nerve stimulation is confirmed and the vagal-AF/electrophysiological testing protocol is repeated. A pre-drug blood sample is obtained and vagal-AF reinstituted. Five minutes later, one of the treatments is administered at doses shown in Table 3. The total dose is infused over 5 minutes and a blood sample obtained immediately thereafter. No maintenance infusion is given. If AF terminated within 15 minutes, the electrophysiological measurements obtained under control conditions are repeated and a blood sample is obtained. If AF is not terminated by the first dose (within 15 minutes), a blood sample is obtained and vagal stimulation is discontinued to allow a return to sinus rhythm. The electrophysiological measurements are repeated and a third and final blood sample for this dose is obtained. AF is reinitiated and the vagal-AF/drug infusion/electrophysiological testing protocol is repeated until AF is terminated by the drug.

Statistical Analysis

Group data are expressed as the mean ±SEM. Statistical analysis is carried out for effective doses for AFCL, and ERP using a t-test with a Bonferroini correction for multiple comparisons. Drug effects on blood pressure, heart rate, diastolic threshold and ECG intervals are assessed at the median dose for termination of AF. Two tailed tests are used and a $p<0.05$ is taken to indicate statistical significance.

TABLE 3

EXPERIMENTAL GROUPS AND DOSES OF DRUGS

| Drug | Dose range tested (μmol/kg) | Effective doses for terminating AF (μmol/kg) | Mean dose required for termination of AF (μmol/kg) | Median dose required for termination of AF (μmol/kg) |
|---|---|---|---|---|
| Flecainide | 1.25–10 | 4–2.5; 1–10 | 4 ± 2 | 2.5 |

A single drug was administered to each dog over the dose range specified until AF was terminated. The number of dogs in which AF was terminated at each dose is shown (number of dogs-dose, in μmol/kg). The mean ±SEM as well as the median dose required to terminate AF is shown. Each dog received only one drug.

Compounds of the present invention may be evaluated by this method. The effectiveness of flecainide as a control in the present study was comparable to that previously reported.

Example 49

Canine Sterile Pericarditis Model

This model has been used to characterize the mechanisms of AF and atrial flutter (AFL). Waldo and colleagues have found that AF depends on reentry and that the site of termination is usually an area of slowed conduction. This canine model is prepared by dusting the exposed atria with talcum powder followed by "burst" pacing the atria over a period of days after recovery. AF is inducible two days after surgery, however, by the fourth day after surgical preparation; sustainable atrial flutter is the predominant inducible rhythm. The inducibility of AF at day 2 is somewhat variable, such that only 50% of dogs may have sustained AF (generally <60 minutes) for a requisite of 30 minutes. However, the sustainable atrial flutter that evolves by the fourth day is inducible in most preparations. Atrial flutter is more readily "mapped" for purposes of determining drug mechanisms. Inducibility of AF subsides after the fourth day post-surgery, similar to the AF that often develops following cardiac surgery that the sterile pericarditis model mimics.

There may be an inflammatory component involved in the etiology of post-surgery AF that would provide a degree of selectivity to an ischaemia or acid selective drug. Similarly, while coronary artery bypass graft (CABG) surgery is performed to alleviate ventricular ischaemia, such patients may also be at risk for mild atrial ischaemia due to coronary artery disease (CAD). While atrial infarcts are rare, there has been an association between AV nodal artery stenosis and risk for AF following CABG surgery. Surgical disruption of the autonomic innervation of the atria may also play a role in AF following CABG.

Methods

Studies are carried out in a canine model of sterile percarditis to determine the potency and efficacy of compounds of the present invention in terminating atrial fibrillation/flutter. Atrial flutter or fibrillation was induced 2 to 4 days after creation of sterile pericarditis in adult mongrel dogs weighing 19 kg to 25 kg. In all instances, the atrial fibrillation or flutter lasted longer than 10 minutes.

Creation of the Sterile Pericarditis Atrial Fibrillation/Flutter Model

The canine sterile pericarditis model is created as previously described. At the time of surgery, a pair of stainless steel wire electrodes coated with FEP polymer except for the tip (O Flexon, Davis and Geck) are sutured on the right atrial appendage, Bachman's bundle and the posteroinferior left atrium close to the proximal portion of the coronary sinus. The distance between each electrode of each pair is approximately 5 mm. These wire electrodes are brought out through the chest wall and exteriorized posteriorly in the interscapular region for subsequent use. At the completion of surgery, the dogs are given antibiotics and analgesics and then are allowed to recover. Postoperative care included administration of antibiotics and analgesics.

In all dogs, beginning on postoperative day 2, induction of stable atrial fibrillation/flutter is attempted in the conscious, non-sedated state to confirm the inducibility and the stability of atrial fibrillation/flutter and to test the efficacy of the drugs. Atrial pacing is performed through the electrodes sutured during the initial surgery. On postoperative day 4, when stable atrial flutter is induced, the open-chest study is performed.

For the open-chest study, each dog is anesthetized with pentobarbital (30 mg/kg IV) and mechanically ventilated with 100% oxygen by use of a Boyle model 50 anesthesia machine (Harris-Lake, Inc.). The body temperature of each dog is kept within the normal physiological range throughout the study with a heating pad. With the dog anesthetized, but before the chest is opened, radiofrequency ablation of the His bundle is performed to create complete atrioventricular (AV) block by standard electrode catheter techniques. This is done to minimize the superimposition of atrial and ventricular complexes during subsequent recordings of unipolar atrial electrograms after induction of atrial flutter. After complete AV block is created, an effective ventricular rate is maintained by pacing of the ventricles at a rate of 60 to 80 beats per minute with a Medtronic 5375 Pulse Generator (Medtronic Inc.) to deliver stimuli via the electrodes sutured to the right ventricle during the initial surgery.

Determination of Stimulus Thresholds and Refractorv Periods During Pacing

For the induction of AF/AFL, one of two previously described methods is used: (1) introduction of one or two premature atrial beats after a train of 8 paced atrial beats at a cycle length of 400 ms, 300 ms, 200 ms, or 150 ms, or (2) rapid atrial Pacing for Periods of 1 to 10 seconds at rates incrementally faster by 10 to 50 beats per minute than the spontaneous sinus rate until atrial flutter is induced or there is a loss of 1:1 atrial capture. Atrial pacing is performed from either the right atrial appendage electrodes or the posteroinferior left atrial electrodes. All pacing is performed using stimuli of twice threshold for each basic drive train with a modified Medtronic 5325 programmable, battery-poared stimulator with a pulse width of 1.8 ms.

After the induction of stable atrial fibrillation/flutter (lasting longer than 10 minutes), the atrial fibrillation/flutter cycle length is measured and the initial mapping and analysis are performed to determine the location of the atrial fibrillation/flutter reentrant circuit. Atrial flutter is defined as a rapid atrial rhythm (rate, >240 beats per minute) characterized by a constant beat-to-beat cycle length, polarity, morphology, and amplitude of the recorded bipolar electrograms.

Drug Efficacy Testing Protocol

1. Effective refractory periods (ERPs) are measured from three sites: right atrial appendage (RAA), posterior left atrium (PLA), and Bachman's Bundle (BB), at two basic cycle lengths 200 and 400 ms.

2. Pace induce A-Fib or AFL. This is attempted for one hour. If no arrhythmia is induced, no further study is done on that day.

3. If induced, AF must have been sustained for 10 minutes. Then a waiting period is allowed for spontaneous termination or 20 minutes, whichever came first.

4. AF is then reinduced and 5 minutes is allowed before starting drug infusion.

5. Drug is then infused in a bolus over 5 minutes.

6. If AF terminated with the first dose then a blood sample is taken and ERP measurements are repeated.

7. Five minutes is allowed for the drug to terminate. If there is no termination then the second dose is given over 5 minutes.

8. After termination and ERPs are measured, a second attempt to reinduce AF is tried for a period of ten minutes.

9. If reinduced and sustained for 10 minutes, a blood sample is taken and the study repeated from #3 above.

10. If no reinduction, then the study is over.

Compounds of the present invention may be evaluated by this method.

Example 50

Assessment of Pain Blockage

CD-1 mice (20–30 g) are restrained in an appropriate holder. A tourniquet is placed at the base of the tail and a solution of the test compound (50 μl, 5 mg/ml) is injected into the lateral tail vein. The tourniquet is removed 10 min after the injection. Suitable dilutions of compound solution are used to obtain an $ED_{50}$ for pain blockade at various times after injection. Pain responses are assessed by pin prick at regular intervals up to 4 hours post injection and the duration of pain blockage is recorded for three animals for each test compound solution. Compounds of the present invention may be evaluated according to the method described. For example, the $ED_{50}$ value for Compound 1 is determined to be 0.073 mg/tail.

Example 51

IN VITRO ASSESSMENT OF INHIBITION ACTIVITY OF ION CHANNEL MODULATING COMPOUNDS ON DIFFERENT CARDIAC IONIC CURRENTS

Cell culture:

The relevant cloned ion channels (e.g. cardiac hH1, Kv1.4, Kv1.5, Kv4.2, Kv2.1, HERG etc.) are studied by transient transfection into HEK cells using the mammalian expression vector pCDNA3. Transfections for each channel type are carried out separately to allow individual study of the ion channel of interest. Cells expressing channel protein are detected by cotransfecting cells with the vector pHook-1 (Invitrogen, San Diego, Calif., USA). This plasmid encoded the production of an antibody to the hapten phOX, which when expressed is displayed on the cell surface. Equal concentrations of individual channel and pHook DNA are incubated with 10× concentration of lipofectAce in Modified Eagle's Medium (MEM, Canadian Life Technologies) and incubated with parent HEK cells plated on 25 mm culture dishes. After 3–4 hours the solution is replaced with a standard culture medium plus 20% fetal bovine serum and 1% antimycotic. Transfected cells are maintained at 37C in an air/5% CO2 incubator in 25 mm Petri dishes plated on glass coverslips for 24–48 hours to allow channel expression to occur. 20 min prior to experiments, cells are treated with beads coated with phOX. After 15 min, excess beads are ished off with cell culture medium and cells which had beads stuck to them are used for electrophysiological tests.

Solutions:

For whole-cell recording the control pipette filling solution contained (in mM): KCl, 130; EGTA, 5; MgCl2, 1; HEPES, 10; Na2ATP, 4; GTP, 0.1; and is adjusted to pH 7.2 with KOH. The control bath solution contained (in mM): NaCl, 135; KCI, 5; sodium acetate, 2.8; MgCl2, 1; HEPES, 10; CaCl2, 1; and is adjusted to pH 7.4 with NaOH. The test ion channel modulating compound is dissolved to 10 mM stock solutions in water and used at concentrations between 0.5 and 100 μM.

Electrophysiological procedures:

Coverslips containing cells are removed from the incubator before experiments and placed in a superfusion chamber (volume 250 μl) containing the control bath solution at 22C to 23C. All recordings are made via the variations of the patch-clamp technique, using an Axopatch 200A amplifier (Axon Instruments, CA). Patch electrodes are pulled from thin-walled borosilicate glass (World Precision Instruments; FL) on a horizontal micropipette puller, fire-polished, and filled with appropriate solutions. Electrodes had resistances of 1.0–2.5 μohm when filled with control filling solution. Analog capacity compensation is used in all whole cell measurements. In some experiments, leak subtraction is applied to data. Membrane potentials have not been corrected for any junctional potentials that arose between the pipette and bath solution. Data are filtered at 5 to 10 kHz before digitization and stored on a microcomputer for later analysis using the pClamp6 software (Axon Instruments, Foster City, Calif.). Due to the high level of expression of channel cDNA's in HEK cells, there is no need for signal averaging. The average cell capacitance is quite small, and the absence of ionic current at negative membrane potentials allowed faithful leak subtraction of data.

Data analysis:

The concentration-response curves for changes in peak and steady-state current produced by the test compound are computer-fitted to the Hill equation:

$$f=1-1/[1+(IC_{50}/D])^n] \quad [1]$$

where f is the fractional current (f=Idrug/Icontrol) at drug concentration [D]; $IC_{50}$ is the concentration producing half-maximal inhibition and n is the Hill coefficient.

Compounds of the present invention may be evaluated by this method. The results show that compounds of the present invention tested have different degree of effectiveness in blocking various ion channels. Block is determined from the decrease in peak hH1 $Na^+$ current, or in steady-state Kv1.5 and integrated Kv4.2 current in the presence of drug. To record $Na^+$ current, cells are depolarized from the holding potential of −100 mV to a voltage of −30 mV for 10 ms to fully open and inactivate the channel. To record Kv1.5 and Kv4.2 current, cells are depolarized from the holding potential of −80 mV to a voltage of +60 mV for 200 ms to fully open the channel. Currents are recorded in the steady-state at a range of drug concentrations during stimulation every 4 s. Reduction in peak current $Na^+$ channel), steady-state current (Kv1.5 channel) or integrated current (Kv4.2) at the test potential of −30 mV ($Na^+$ channel) or +60 mV (Kv1.5 and Kv4.2 channel) is normalized to control current, then plotted against the concentration of test compound. Data are averaged from 4–6 cells. Solid lines are fit to the data using a Hill equation. The $IC_{50}$ values for some of the compounds of the present invention on various ion channels studied are summarized in the following table:

| Cpd# | Na (μM) | Kv1.5 (μM) | Kv4.2 (μM) | HERG (μM) |
|---|---|---|---|---|
| 1 | 8 | 0.3 | 2 | 0.1 |
| 2 | 34 | 4 | 7 | 0.06 |
| 3 | 94 | 6 | 13 | 0.6 |
| 4 | 1 | 0.1 | 0.8 | 0.02 |
| 5 | 239 | 170 | 71 | 0.9 |
| 6 | 0.3 | 0.8 | 0.9 | 0.3 |
| 7 | 15 | 5 | 10 | 0.8 |
| 8 | 1212 | 0.8 | 11 | 0.4 |
| 9 | 14 | 1 | 3 | 0.05 |
| 10 | 12 | 0.8 | 1 | 0.1 |
| 11 | 152 | 11 | 14 | 0.08 |
| 12 | 3 | 0.6 | 1 | 0.004 |
| 13 | 8 | 0.7 | 3 | 0.4 |
| 14 | — | 0.7 | — | — |
| 15 | 8 | 0.1 | 0.6 | 1 |
| 17 | — | 4 | — | 1 |
| 18 | — | 3 | — | 1 |
| 19 | — | 0.3 | — | 0.4 |
| 20 | — | 0.2 | — | 0.1 |
| 21 | — | 2 | — | 0.06 |
| 22 | — | 0.4 | — | 1 |
| 23 | — | 3 | — | 9 |
| 24 | — | 2 | — | 0.2 |
| 25 | — | 8 | — | 0.1 |
| 26 | — | 0.8 | — | 0.2 |
| 27 | — | 0.6 | — | 0.1 |
| 28 | — | 0.8 | — | 2 |
| 29 | — | 0.7 | — | 0.08 |
| 30 | — | 1 | — | 2 |
| 31 | — | 4 | — | 3 |
| 32 | — | 4 | — | 0.3 |
| 33 | — | 3 | — | 0.9 |
| 34 | — | 1 | — | 0.04 |
| 37 | — | 18 | — | 4 |
| 38 | — | 0.4 | — | 1 |
| 39 | — | 0.7 | — | 3 |
| 40 | — | 23 | — | 1 |

-continued

| Cpd# | Na (μM) | Kv1.5 (μM) | Kv4.2 (μM) | HERG (μM) |
|---|---|---|---|---|
| 41 | — | 5 | — | 0.6 |
| 43 | — | 1.6 | — | 0.7 |

The activity of other compounds of the present invention to block various ionic currents of interest may be similarly studied.

Example 52

Assessment of Proarrhythmia (Torsade de Pointes) Risk of Ion Channel Modulating Compounds in Primates Methods General Surgical Preparation:

All studies are carried out in male *Macaca fascicularis* weighing between 4 and 5.5 kg. Animals are fasted over night and pre-medicated with ketamine (10 mg/kg im). Both saphenous veins are cannulated and a saline drip instituted to keep the lines patent. Halothane anaesthesia (1.5% in oxygen) is administered via a face mask. Lidocaine spray (10% spray) is used to facilitate intubation. After achieving a sufficient depth of anaesthesia, animals are intubated with a 4 or 5 French endotrachial tube. After intubation halothane is administered via the endotracheal tube and the concentration is reduced to 0.75–1%. Artificial respiration is not used and all animals continue to breathe spontaneously throughout the experiment. Blood gas concentrations and blood pH are measured using a blood gas analyser (AVO OPTII). The femoral artery is cannulated to record blood pressure.

Blood pressure and a modified lead II EGG are recorded using a MACLAB 4S recording system paired with a Macintosh PowerBook (2400c/180). A sampling rate of 1 kHz is used for both signals and all data is archived to a Jazz disc for subsequent analysis.

Vagal Nerve Stimulation:

Either of the vagi is isolated by blunt dissection and a pair of electrodes inserted into the nerve trunk. The proximal end of the nerve is crushed using a vascular clamp and the nerve is stimulated using square wave pulses at a frequency of 20 Hz with a 1 ms pulse width delivered from the MACLAB stimulator. The voltage (range 2–10V) is adjusted to give the desired bradycardic response. The target bradycardic response is a reduction in heart rate by half. In cases where a sufficient bradycardic response could not be obtained, 10 μg/kg neostigmine iv is administered. This dose of neostigmine is also given after administration of the test drug in cases where the test drug has vagolytic actions.

Test Compounds:

A near maximum tolerated bolus dose of the test compound, infused (iv) over 1 minute, is used to assess the risk of torsade de pointes caused by each test compound. The actual doses vary slightly depending on the animals' weight. Clofilium, 30 μmol/kg, is used as a positive comparison (control) for these studies. The expectation is that a high dose of drug would result in a high incidence of arrhythmias. The test compounds are dissolved in saline immediately before administration.

Experimental Protocol:

Each animal receives a single dose of a given drug iv. Before starting the experiment, two 30 second episodes of vagal nerve stimulation are recorded. A five minute rest period is allowed between episodes and before starting the experiment. The test solution is administered as an iv bolus at a rate of 5 ml/minute for 1 minute using an infusion pump (total volume 5 ml). ECG and blood pressure responses are monitored continuously for 60 minutes and the occurrence of arrhythmias is noted. The vagal nerve is stimulated for 30 seconds at the following times after injection of the drug: 30 seconds, 2, 5, 10, 15, 20, 25, 30 and 60 minutes.

Blood samples (1 ml total volume) are taken from each treated animal at the following times after drug administration: 30 seconds, 5, 10, 20, 30 and 60 minutes as well as 3, 6, 24 and 48 hours. Blood samples taken up to 60 minutes after drug administration are arterial while those taken after this time are venous. Samples are centrifuged, the plasma decanted and frozen. Samples are kept frozen before analysis of plasma concentration of the drug and potassium.

Statistics:

The effect of drugs on blood pressure, heart rate and ECG intervals are described as the mean±SEM for a group size of "n."

Compounds of the present invention may be evaluated by this method.

All publications and patent applications mentioned in this specification are herein incorporated by reference to the same extent as if each individual publication or patent application is specifically and individually incorporated by reference.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for treating a disease or condition caused by defective or inadequate function of an ion channel in a human, wherein the method comprises administering to a human in need thereof, an effective amount of a compound of formula (I), or a pharmaceutically acceptable salt, ester, amide, complex, chelate, solvate, stereoisomer, stereoisomeric mixture, geometric isomer, crystalline or amorphous form, thereof:

(I)

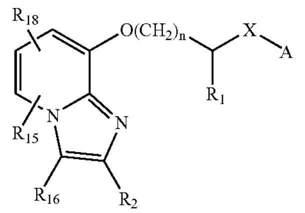

wherein, independently at each occurrence, n is selected from 0, 1, 2 and 3; X is selected from a direct bond, —C($R_3$)=CH—, and —C($R_4$, $R_5$)—Y—;

Y is selected from a direct bond, O, S, and $C_1$–$C_4$alkylene;

$R_2$, $R_{15}$, $R_{16}$ and $R_{18}$ are independently selected from bromine, chlorine, fluorine, carboxy, hydrogen, hydroxy, hydroxymethyl, methanesulfonamido, nitro, sulfamyl, cyano, $CHF_2$, $CH_2F$, $CF_3$, $C_2$–$C_7$alkanoyloxy, $C_1$–$C_6$alkyl, $C_3$–$C_8$cycloalkyl, phenyl, naphthyl, benzyl, $C_1$–$C_6$alkoxy, $C_2$–$C_7$alkoxycarbonyl, $C_1$–$C_6$thioalkyl, $CH_2N(R_{13}$, $R_{14}$) and $N(R_{13}, R_{14})$ where $R_{13}$ and $R_{14}$ are independently selected from hydrogen, acetyl, methanesulfonyl, and $C_1$–$C_6$alkyl, or $R_2$ and $R_{16}$, when taken together with the carbon to which they are attached, may form a $C_4$–$C_7$cycloalkyl;

$R_3$ is selected from hydrogen, $C_1$–$C_6$alkyl, $C_3$–$C_8$cycloalkyl, phenyl, naphthyl, and benzyl;

$R_1$, $R_4$ and $R_5$ are independently selected from hydrogen, $C_1$–$C_6$alkyl, phenyl, naphthyl, and benzyl, or $R_4$ and $R_5$, when taken together with the carbon to which they are attached, may form a spiro $C_3$–$C_5$cycloalkyl;

A is selected from $C_5$–$C_{12}$alkyl, a $C_3$–$C_{13}$carbocyclic ring, and ring systems selected from formulae (II), (III), (IV), (V), (VI) and (VII):

(II)

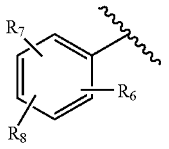

where $R_6$, $R_7$ and $R_8$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, phenyl, naphthyl, and $N(R_{13},R_{14})$ where $R_{13}$ and $R_{14}$ are independently selected from hydrogen, acetyl, methanesulfonyl, and $C_1$–$C_6$alkyl;

(III)

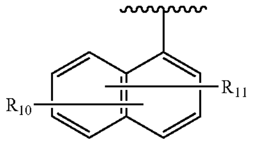

and (IV)

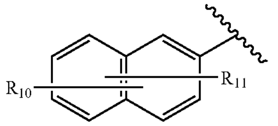

where $R_{10}$ and $R_{11}$ are independently selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, phenyl, naphthyl, and $N(R_{13},R_{14})$ where $R_{13}$ and $R_{14}$ are independently selected from hydrogen, acetyl, methanesulfonyl, and $C_1$–$C_6$alkyl;

(V)

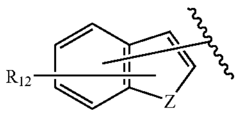

where $R_{12}$ is selected from bromine, chlorine, fluorine, carboxy, hydrogen, hydroxy, hydroxymethyl, methanesulfonamido, nitro, sulfamyl, trifluoromethyl, $C_2$–$C_7$alkanoyloxy, $C_1$–$C_6$alkyl, $C_1$–$C_6$alkoxy, $C_2$–$C_7$alkoxycarbonyl, $C_1$–$C_6$thioalkyl, cyano, phenyl, naphthyl, and $N(R_{13},R_{14})$ where $R_{13}$ and $R_{14}$ are independently selected from hydrogen, acetyl, methanesulfonyl, and $C_1$–$C_6$alkyl; and Z is selected from CH, $CH_2$, O, N and S, where Z is directly bonded to "X" as shown in formula (I) when Z is CH, or Z is directly bonded to $R_9$ or "X" as shown in formula (I) when Z is N, and $R_9$ is selected from hydrogen, $C_1$–$C_6$alkyl, $C_3$–$C_8$cycloalkyl, phenyl, naphthyl, and benzyl;

(VI)

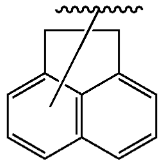

(VII)

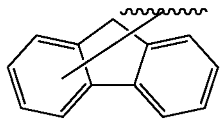

wherein the disease or condition is selected from the group consisting of arrhythmia, atrial or supraventricular arrhythmia, ventricular arrhythmia, atrial fibrillation, ventricular fibrillation, atrial flutter and ventricular flutter.

2. The method of claim 1, wherein n is 2.

3. The method of claim 1 wherein the compound of formula (I), or a pharmaceutically acceptable salt, ester, amide, complex, chelate, solvate, stereoisomer, stereoisomeric mixture, geometric isomer, crystalline or amorphous form, thereof; is a compound of formula (I) wherein X is —$C(R_4,R_5)$—Y—, and $R_4$ and $R_5$, when taken together with the carbon to which they are attached form a spiro $C_3$–$C_5$ cycloalkyl.

4. The method of claim 3 wherein the compound of formula (I) is a compound of formula (I) wherein Y is a direct bond.

5. The method of claim 4 wherein the compound of formula (I) is a compound of formula (I) wherein $R_4$ and $R_5$, when taken together with the carbon to which they are attached form a spiro $C_3$cycloalkyl.

6. The method of claim 1 wherein the compound of formula (I) is a compound of formula (I), or a pharmaceutically acceptable salt, ester, amide, complex, chelate, solvate, stereoisomer, stereoisomeric mixture, geometric isomer, crystalline or amorphous form, thereof; wherein A is selected from formula (V); and Z is N or S.

7. The method of claim 6 wherein a compound of formula (I) is a compound of formula (I) wherein X is a direct bond or —$C(R_4,R_5)$—Y—.

8. The method of claim 1 wherein said ion channel is a potassium channel.

9. The method of claim 8 wherein said potassium channel is a voltage-activated potassium channel.

10. The method of claim 9 wherein said voltage-activated potassium channel is responsible for Kv1.3, Kv1.5 or HERG currents.

11. The method of claim 1 wherein said ion channel is responsible for one or more cardiac early repolarizing currents comprising ionic currents which activate rapidly after membrane depolarization and which effect repolarization of the cell.

12. The method of claim 11 wherein said early repolarizing currents comprise the cardiac transient outward potassium current ($I_{to}$) and/or the ultrarapid delayed rectifier current ($I_{Kur}$).

13. The method of claim 12 wherein the cardiac transient outward potassium current ($I_{to}$) and/or the ultrarapid delayed rectifier current ($I_{Kur}$) comprise at least one of the Kv4.2, Kv4.3, Kv2.1, Kv1.4 and Kv1.5 currents.

14. The method of claim 1 wherein said ion channel is a cardiac potassium channel responsible for Kv1.5 currents.

15. The method of claim 1 wherein said ion channel is responsible for one or more neuronal early repolarizing currents comprising ionic currents which activate rapidly after membrane depolarization and which effect repolarization of the cell.

16. The method of claim 15 wherein the early repolarizing currents comprise the neuronal transient outward potassium current ($I_A$) and/or the ultrarapid delayed rectifier current ($I_{Kur}$).

17. The method of claim 16 wherein the neuronal transient outward potassium current ($I_A$) and/or the ultrarapid delayed rectifier current ($I_{Kur}$) comprise at least one of the Kv4.2, Kv4.3, Kv2.1, Kv1.4 and Kv1.5 currents.

18. The method of claim 1 wherein said ion channel is a neuronal potassium channel responsible for Kv1.5 currents.

19. The method of claim 1 wherein said ion channel is a sodium channel.

20. The method of claims 19 wherein said sodium channel is a voltage-activated sodium channel.

21. The method of claims 20 wherein said voltage-activated sodium channel is one of the $Na_v1$, $Na_v2$ or $Na_v3$ series.

22. The method of claims 21 wherein said sodium channel is a ligand-activated sodium channel.

23. The method of claim 19 wherein said sodium channel is a cardiac sodium channel.

24. The method of claim 19 wherein said sodium channel is a neuronal sodium channel.

25. The method of claim 19 wherein said sodium channel is a skeletal muscle sodium channel.

26. The method of claim 19 wherein said sodium channel is a central nervous system sodium channel.

27. The method of claim 19 wherein said sodium channel is a peripheral nervous system sodium channel.

28. The method of claim 1, wherein the condition is selected from the group consisting of atrial or supraventricular arrhythmia, atrial fibrillation, ventricular fibrillation, atrial and ventricular flutter.

29. The method of claim 28, wherein the condition is selected from the group consisting of atrial fibrillation and atrial flutter.

* * * * *

UNITED STATES PATENT AND TRADEMARK OFFICE

CERTIFICATE OF CORRECTION

PATENT NO. : 7,105,534 B2
APPLICATION NO. : 10/297988
DATED : September 12, 2006
INVENTOR(S) : Gregory N. Beatch et al.

It is certified that error appears in the above-identified patent and that said Letters Patent is hereby corrected as shown below:

<u>Column 67</u>
Line 30, "$C_1$-$C_6$thioalkyl, phenyl," should read as -- $C_1$-$C_6$thioalkyl, cyano, phenyl, --.
Line 52, "$C_1$-$C_6$thioalkyl, phenyl," should read as -- $C_1$-$C_6$thioalkyl, cyano, phenyl, --.

Signed and Sealed this

Twelfth Day of August, 2008

JON W. DUDAS
*Director of the United States Patent and Trademark Office*